United States Patent
Liu et al.

(10) Patent No.: US 10,946,106 B2
(45) Date of Patent: Mar. 16, 2021

(54) TUMOR-SPECIFIC PAYLOAD DELIVERY AND IMMUNE ACTIVATION USING A HUMAN ANTIBODY TARGETING A HIGHLY SPECIFIC TUMOR CELL SURFACE ANTIGEN

(71) Applicant: The Regents of the University of California, Oakland, CA (US)

(72) Inventors: Bin Liu, San Francisco, CA (US); Scott Bidlingmaier, San Francisco, CA (US); Yang Su, South San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 239 days.

(21) Appl. No.: 15/779,490

(22) PCT Filed: Nov. 29, 2016

(86) PCT No.: PCT/US2016/064033
§ 371 (c)(1),
(2) Date: May 25, 2018

(87) PCT Pub. No.: WO2017/095823
PCT Pub. Date: Jun. 8, 2017

(65) Prior Publication Data
US 2018/0369409 A1    Dec. 27, 2018

Related U.S. Application Data

(60) Provisional application No. 62/261,112, filed on Nov. 30, 2015.

(51) Int. Cl.
| | | |
|---|---|---|
| *C07K 16/40* | (2006.01) |
| *A61K 47/68* | (2017.01) |
| *G01N 33/574* | (2006.01) |
| *C12N 9/16* | (2006.01) |
| *A61P 35/00* | (2006.01) |
| *A61K 35/17* | (2015.01) |
| *C07K 16/28* | (2006.01) |
| *A61K 35/00* | (2006.01) |
| *A61K 39/00* | (2006.01) |

(52) U.S. Cl.
CPC ......... *A61K 47/6871* (2017.08); *A61K 35/17* (2013.01); *A61K 47/6803* (2017.08); *A61K 47/6811* (2017.08); *A61P 35/00* (2018.01); *C07K 16/2809* (2013.01); *C07K 16/40* (2013.01); *C12N 9/16* (2013.01); *C12Y 301/03001* (2013.01); *G01N 33/57407* (2013.01); *G01N 33/57492* (2013.01); *A61K 35/00* (2013.01); *A61K 2039/505* (2013.01); *A61K 2039/572* (2013.01); *C07K 2317/31* (2013.01); *C07K 2317/56* (2013.01); *C07K 2317/565* (2013.01); *C07K 2317/622* (2013.01); *C07K 2317/72* (2013.01); *C07K 2317/732* (2013.01); *C07K 2317/92* (2013.01); *C07K 2319/30* (2013.01)

(58) Field of Classification Search
CPC ....................... A61K 47/6871; A61K 47/6811; A61K 35/17; A61K 47/6803; C07K 16/2809; C07K 16/40
See application file for complete search history.

(56) References Cited

U.S. PATENT DOCUMENTS

2014/0120085 A1    5/2014    Tureci et al.

FOREIGN PATENT DOCUMENTS

| EP | 0429242 A2 | 5/1991 |
| WO | WO 91/07500 A1 | 5/1991 |
| WO | WO 2014/146487 A1 | 9/2014 |

OTHER PUBLICATIONS

Mabs 6: 86-94 , 2004 (see WO search result) (Year: 2004).*
Google search result for anti-ALPP polyclonal antibodies from year: 2020, 2014 (Year: 2020).*
PCT International Search Report and Written Opinion dated Mar. 13, 2017 issued in PCT/US2016/064033.
PCT International Preliminary Report dated Jun. 5, 2018 issued in PCT/US2016/064033.
EP Supplementary Partial Search Report dated Sep. 16, 2019 issued in EP 16871367.5.
Freeman, et al. (2001) "Isolation of antibody to human placental alkaline phosphatase (PLAP) from extracts of human placentae.", *American Journal of Reproductive Immunology*, 46(2): 149-160.
Jain, et al. (2007) "A phage antibody to the active site of human placental alkaline phosphatase with higher affinity to the enzyme-substrate complex" *Molecular Immunology* 44(1): 369-376.
Kala, et al. (2002) "Phage Displayed Antibodies to Heat Stable Alkaline Phosphatase: Framework Region as a Determinant of Specificity" *J. Biochem* 132(4): 535-541.
Nouri, et al. (2000) "A new highly specific monoclonal antibody against placental alkaline phosphatase: A potential marker for the early detection of testis tumour" *BJU International*, 86(7): 894-900.
Paiva, et al. (1983) "Immunohistochemical localization of placental-like alkaline phosphatase in testis and germ-cell tumors using monoclonal antibodies" *The American Journal of Pathology*, 111(2): 156-165.
Ravenni, et al. (2014) "A human monoclonal antibody specific to placental alkaline phosphatase, a marker of ovarian cancer" *MABS* 6(1): 86-94.

(Continued)

*Primary Examiner* — Lei Yao
(74) *Attorney, Agent, or Firm* — Tom Hunter; Weaver Austin Villeneuve & Sampson LLP

(57) ABSTRACT

This invention provides antibodies directed against a highly specific and previously unrecognized marker for cancerous cells. In certain embodiments an isolated antibody or fragment thereof that specifically binds human placentally expressed ALPP and/or ALPPL2, but not ALPL and ALPI that are expressed outside the placenta is provided as well as immunoconjugates comprising such antibodies.

11 Claims, 9 Drawing Sheets
Specification includes a Sequence Listing.

(56) References Cited

OTHER PUBLICATIONS

Saini, et al. (2005) "Targeting the active site of the placental isozyme of alkaline phosphatase by phage-displayed scFv antibodies selected by a specific uncompetitive inhibitor" *BMC Biotechnology*, 5:33 (13 pages).
Sheikholvaezin, et al. (2007) "Tumor Radioimmunolocalization in Nude Mice by Mono- and Divalent- Single-Chain Fv Antiplacental Alkaline Phosphatase Antibodies" *Cancer Biotherapy & Radiopharmaceuticals*, 22(1): 64-72.
EP Office Action dated Jul. 22, 2020 issued in EP 16871367.5.
Su, Yang et al. (2020) "ALPPL2 is a highly specific and targetable tumor cell surface antigen" *bioRxiv*, 43 pages; DOI: 10.1101/2020.01.07.898122; Retrieved from the Internet: URL:https://www.biorxiv.org/content/10.1101/2020.01.07.898122v1.full.pdf.

\* cited by examiner

UniProtKB - P05187 ALPP

```
         10          20          30          40          50
MLGPCMLLLL  LLLGLRLQLS  LGIIPVEEEN  PDFWNREAAE  ALGAAKKLQP
         60          70          80          90         100
AQTAAKNLII  FLGDGMGVST  VTAARILKGQ  KKDKLGPEIP  LAMDRFPYVA
        110         120         130         140         150
LSKTYNVDKH  VPDSGATATA  YLCGVKGNFQ  TIGLSAAARF  NQCNTTRGNE
        160         170         180         190         200
VISVMNRAKK  AGKSVGVVTT  TRVQHASPAG  TYAHTVNRNW  YSDADVPASA
        210         220         230         240         250
RQEGCQDIAT  QLISNMDIDV  ILGGGRKYMF  RMGTPDPEYP  DDYSQGGTRL
        260         270         280         290         300
DGKNLVQEWL  AKRQGARYVW  NRTELMQASL  DPSVTHLMGL  FEPGDMKYEI
        310         320         330         340         350
HRDSTLDPSL  MEMTEAALRL  LSRNPRGFFL  FVEGGRIDHG  HHESRAYRAL
        360         370         380         390         400
TETIMFDDAI  ERAGQLTSEE  DTLSLVTADH  SHVFSFGGYP  LRGSSIFGLA
        410         420         430         440         450
PGKARDRKAY  TVLLYGNGPG  YVLKDGARPD  VTESESGSPE  YRQQSAVPLD
        460         470         480         490         500
EETHAGEDVA  VFARGPQAHL  VHGVQEQTFI  AHVMAFAACL  EPYTACDLAP
        510         520         530
PAGTTDAAHP  GRSVVPALLP  LLAGTLLLLE  TATAP
```

UniProtKB - P10696 ALPPL2

```
         10          20          30          40          50
MQGPWVLLLL  GLRLQLSLGI  IPVEEENPDF  WNRQAAEALG  AAKKLQPAQT
         60          70          80          90         100
AAKNLIIFLG  DGMGVSTVTA  ARILKGQKKD  KLGPETFLAM  DRFPYVALSK
        110         120         130         140         150
TYSVDKHVPD  SGATATAYLC  GVKGNFQTIG  LSAAARFNQC  NTTRGNEVIS
        160         170         180         190         200
VMNRAKKAGK  SVGVVTTTRV  QHASPAGAYA  HTVNRNWYSD  ADVPASARQE
        210         220         230         240         250
GCQDIATQLI  SNMDIDVILG  GRKYMFPMG   TPDPEYPDDY  SQGGTRLDGK
        260         270         280         290         300
NLVQEWLAKH  QGARYVWNRT  ELLQASLDPS  VTHLMGLFEP  GDMKYEIHRD
        310         320         330         340         350
STLDPSLMEM  TEAALLLLSR  NPRGFFLFVE  GGRIDHGHHE  SRAYRALTET
        360         370         380         390         400
IMFDDAIERA  GQLTSEEDTL  SLVTADHSHV  FSFGGYPLRG  SSIFGLAPGK
        410         420         430         440         450
ARDRKAYTVL  LYGNGPGYVL  KDGARPDVTE  SESGSPEYRQ  QSAVPLDGET
        460         470         480         490         500
HAGEDVAVFA  RGPQAHLVHG  VQEQTFIAHV  MAFAACLEPY  TACDLAPRAG
        510         520         530
TTDAAHPGPS  VVPALLPLLA  GTLLLLGTAT  AP
```

*Fig. 1*

TUMOR-SPECIFIC PAYLOAD DELIVERY AND IMMUNE ACTIVATION USING A HUMAN ANTIBODY TARGETING A HIGHLY SPECIFIC TUMOR CELL SURFACE ANTIGEN

CROSS-REFERENCE TO RELATED APPLICATIONS

This application is a U.S. 371 National Phase of PCT/US2016/064033, filed on Nov. 29, 2016, which claims benefit of and priority to U.S. Ser. No. 62/261,112, filed Nov. 30, 2015, both of which are incorporated herein by reference in their entirety for all purposes.

STATEMENT OF GOVERNMENTAL SUPPORT

This invention was made with government support under Grant Nos. R01 CA129491, R01 CA118919, and R01 CA171315 awarded by the National Institutes of Health. The Government has certain rights in this invention.

INCORPORATION BY REFERENCE OF SEQUENCE LISTING PROVIDED AS A TEXT FILE

A Sequence Listing is provided herewith as a text file, "UCSF-P038US_ST25.txt" created on Sep. 4, 2018 and having a size of 103,204 bytes. The contents of the text file are incorporated by reference herein in their entirety.

BACKGROUND

Cancer therapy is progressing along several promising platforms, including antibody drug conjugates (ADCs) and immunotherapy. For the ADC field, the challenge is to achieve durable responses. For immunotherapy, while the response can be durable, only a small fraction of the treated patients respond, and the approach works for only a few types of cancer (Rizvi et al. (2015) Lancet Oncol., 16: 257-265; Topalian et al. (2012) N. E. J. M. 366: 2443-2454). Besides developing biomarkers to predict responder vs. non responder, a major challenge for the immunotherapy field is to increase response rates and expand applicability to a broader range of indications.

To achieve a durable response with ADCs, the field is trending towards arming antibodies with supertoxic drugs that kill both dividing and resting tumor cells (e.g., PBD and other DNA chelators) and are orders of magnitude more potent than microtubule inhibitors such as auristatin derivatives (Jeffrey et al. (2013) Bioconjug. Chem., 24: 1256-1263; Kung et al. (2013) Blood 122: 1455-1463; Saunders et al. (2015) Sci. Transl. Med. 7: 302ra136). This approach may be necessary to compensate for the relative inefficiency of drug delivery through conjugation to an antibody, especially in solid tumors. Promising clinical trial results with durable responses have been reported using ADCs armed with these supertoxins in both hematological malignancies (CD33-PBD in AML) (Stein et al. (2014) Interim Analysis of a Phase 1 Trial of SGN-CD33A in Patients with CD33-Positive Acute Myeloid Leukemia (AML). 56th ASH annual meeting Session 616) and solid tumors (DLL3-PBD in neuroendocrine small cell lung cancer) (Pietanza et al. (2015) Eur. J. Canc. 51(3): S712). A prerequisite for successful adaptation of this approach in other tumors is the identification of a highly specific, highly expressed tumor antigen, so that any on-target toxicity will be kept at a minimum level.

There are many ways to improve current immunotherapy, including better understanding of responder versus non responder, analysis of T cell repertoire diversification or clonality development in the context of response and toxicity, and combination treatments such as checkpoint inhibitor combo (CTLA-4+PD1), checkpoint inhibitor plus chemo, and vaccine plus checkpoint inhibitor. Yet another approach to harness the power of the host immune system against cancer is based on site-specific recruitment and activation of T cells. For example, a bispecific antibody can be constructed by combining anti-tumor and anti-T cell (e.g., CD3) antibody fragments using either the BiTE (Bispecific T Cell Engager) (Harrington et al. (2015) PloS One 10: e0135945; Klinger et al. (2012) Blood, 119: 6226-6233; Molhoj et al. (2007) Mol. Immunol. 44: 1935-1943) or DART (Dual-Affinity Retargeting) platforms (Chichili et al. (2015) Sci. Transl. Med. 7: 289ra282; Moore et al. (2011) Blood, 117: 4542-4551). While promising, application of this approach requires the identification of a highly specific tumor cell surface antigen to minimize on-target toxicities and expand the therapeutic window.

SUMMARY

Various embodiments contemplated herein may include, but need not be limited to, one or more of the following:

Various embodiments contemplated herein may include, but need not be limited to, one or more of the following:

Embodiment 1

An isolated antibody or fragment thereof that specifically binds human placentally expressed ALPP and/or ALPPL2, but not ALPL and ALPI that are expressed outside the placenta.

Embodiment 2

The antibody of embodiment 1, wherein said antibody is an antibody that specifically binds cells that express or ALPPL2 and/or ALPP, wherein said antibody specifically binds an epitope bound by one or more antibodies selected from the group consisting of M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF.

Embodiment 3

The antibody according to any one of embodiments 1-2, wherein said antibody preferentially binds the cell surface form of ALPPL2 as compared to the shed/solution form of ALPPL2.

Embodiment 4

The antibody according to any one of embodiments 1-3, wherein said antibody binds a cell expressing ALPPL2 with an affinity of better than about 5 nM, or better than about 3 nM, or about 2 nM or better.

Embodiment 5

The antibody according to any one of embodiments 1-3, wherein said antibody binds a cell expressing ALPPL2 with an affinity of better than about 50 pM, or with an affinity of better than about 40 pM, or with an affinity better than about 30 pM, or with an apparent affinity of about 28 pM in its IgG1 form.

Embodiment 6

The antibody according to any one of embodiments 2-5, wherein said cells that express ALPP and/or ALPPL2 are cancer cells.

Embodiment 7

The antibody according to any one of embodiments 2-6, wherein said cells that express or overexpress are cells of a cancer selected from the group consisting of mesothelioma, testicular cancer, endometrial cancer, and subsets of ovarian, pancreatic, and non small cell lung cancers.

Embodiment 8

The antibody of embodiment 7, wherein said antibody binds cells of a cell line selected from the group consisting of M28, VAMT-1, CAPAN-1, and H1651 cells.

Embodiment 9

The antibody according to any one of embodiments 1-8, wherein said antibody comprises at least one heavy chain variable region (VH) and at least one light chain variable region (VL), wherein said heavy chain variable region contains VH CDR1, and/or VH CDR2, and/or VH CDR3 of an antibody selected from the group consisting of M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF.

Embodiment 10

The antibody according to any one of embodiments 1-8, wherein said antibody comprises at least one heavy chain variable region (VH) and at least one light chain variable region (VL), wherein said light chain variable region contains VL CDR1, and/or VL CDR2, and/or VL CDR3 of an antibody selected from the group consisting of M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF.

Embodiment 11

The antibody according to any one of embodiments 1-8, wherein said antibody comprises at least one heavy chain variable region (VH) and at least one light chain variable region (VL), wherein said heavy chain variable region is a heavy chain variable region of an antibody selected from the group consisting of M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF.

Embodiment 12

The antibody of embodiment 11, wherein said antibody contains at least one heavy chain variable region of an M25ADLF antibody.

Embodiment 13

The antibody of embodiment 11, wherein said antibody contains at least one heavy chain variable region of an M25ADLFEG antibody.

Embodiment 14

The antibody of embodiment 11, wherein said antibody contains at least one heavy chain variable region of an M25ADLFDS antibody.

Embodiment 15

The antibody of embodiment 11, wherein said antibody contains at least one heavy chain variable region of an M25FYIA antibody.

Embodiment 16

The antibody of embodiment 11, wherein said antibody contains at least one heavy chain variable region of an M25FYIAEG antibody.

Embodiment 17

The antibody of embodiment 11, wherein said antibody contains at least one heavy chain variable region of an M25FYIADS antibody.

Embodiment 18

The antibody of embodiment 11, wherein said antibody contains at least one heavy chain variable region of an M25 antibody.

Embodiment 19

The antibody of embodiment 11, wherein said antibody contains at least one heavy chain variable region of an M25EG antibody.

Embodiment 20

The antibody of embodiment 11, wherein said antibody contains at least one heavy chain variable region of an M25DS antibody.

Embodiment 21

The antibody of embodiment 11, wherein said antibody contains at least one heavy chain variable region of an M25AELF antibody.

Embodiment 22

The antibody of embodiment 11, wherein said antibody contains at least one heavy chain variable region of an M25AELFEG antibody.

Embodiment 23

The antibody of embodiment 11, wherein said antibody contains at least one heavy chain variable region of an M25AELFDS antibody.

Embodiment 24

The antibody of embodiment 11, wherein said antibody contains at least one heavy chain variable region of an M25ADL99P antibody.

Embodiment 25

The antibody of embodiment 11, wherein said antibody contains at least one heavy chain variable region of an M25ADL99G antibody.

Embodiment 26

The antibody of embodiment 11, wherein said antibody contains at least one heavy chain variable region of an M25ADS95R antibody.

Embodiment 27

The antibody of embodiment 11, wherein said antibody contains at least one heavy chain variable region of an M25ADD28G antibody.

Embodiment 28

The antibody of embodiment 11, wherein said antibody contains at least one heavy chain variable region of an M25ADS91G antibody.

Embodiment 29

The antibody of embodiment 11, wherein said antibody contains at least one heavy chain variable region of an M25ADY93H antibody.

Embodiment 30

The antibody of embodiment 11, wherein said antibody contains at least one heavy chain variable region of an M25ADYHSRLF antibody.

Embodiment 31

The antibody of embodiment 11, wherein said antibody contains at least one heavy chain variable region of an M25GRITSGFYGDwtLC antibody.

Embodiment 32

The antibody of embodiment 11, wherein said antibody contains at least one heavy chain variable region of an M25FSITSGFYGDwtLC antibody.

Embodiment 33

The antibody of embodiment 11, wherein said antibody contains at least one heavy chain variable region of an M253018IA antibody.

Embodiment 34

The antibody of embodiment 11, wherein said antibody contains at least one heavy chain variable region of an M253018LF antibody.

Embodiment 35

The antibody of embodiment 11, wherein said antibody contains at least one heavy chain variable region of an M25AD antibody.

Embodiment 36

The antibody of embodiment 11, wherein said antibody contains at least one heavy chain variable region of an M25ADX antibody.

Embodiment 37

The antibody of embodiment 11, wherein said antibody contains at least one heavy chain variable region of an ALPPL2rd3_1 antibody.

Embodiment 38

The antibody of embodiment 11, wherein said antibody contains at least one heavy chain variable region of an ALPPL2rd3_2 antibody.

Embodiment 39

The antibody of embodiment 11, wherein said antibody contains at least one heavy chain variable region of an M25AGIA antibody.

Embodiment 40

The antibody of embodiment 11, wherein said antibody contains at least one heavy chain variable region of an M25AGLF antibody.

Embodiment 41

The antibody of embodiment 11, wherein said antibody contains at least one heavy chain variable region of an M25ASIA antibody.

Embodiment 42

The antibody of embodiment 11, wherein said antibody contains at least one heavy chain variable region of an M25ASLF antibody.

Embodiment 43

The antibody of embodiment 11, wherein said antibody contains at least one heavy chain variable region of an M25ASwt antibody.

Embodiment 44

The antibody of embodiment 11, wherein said antibody contains at least one heavy chain variable region of an M25AVIA antibody.

Embodiment 45

The antibody of embodiment 11, wherein said antibody contains at least one heavy chain variable region of an M25AVLF antibody.

Embodiment 46

The antibody of embodiment 11, wherein said antibody contains at least one heavy chain variable region of an M25ALIA antibody.

Embodiment 47

The antibody of embodiment 11, wherein said antibody contains at least one heavy chain variable region of an M25ALLF antibody.

Embodiment 48

The antibody of embodiment 11, wherein said antibody contains at least one heavy chain variable region of an M25wtIA antibody.

Embodiment 49

The antibody of embodiment 11, wherein said antibody contains at least one heavy chain variable region of an M25wtLF antibody.

Embodiment 50

The antibody according to any one of embodiments 1-8, wherein said antibody comprises at least one heavy chain variable region (VH) and at least one light chain variable region (VL), wherein said light chain variable region is a light chain variable region of an antibody selected from the group consisting of M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF.

Embodiment 51

The antibody of embodiment 50, wherein said antibody contains at least one light chain variable region of an M25ADLF antibody.

Embodiment 52

The antibody of embodiment 50, wherein said antibody contains at least one light chain variable region of an M25ADLFEG antibody.

Embodiment 53

The antibody of embodiment 50, wherein said antibody contains at least one light chain variable region of an M25ADLFDS antibody.

Embodiment 54

The antibody of embodiment 50, wherein said antibody contains at least one light chain variable region of an M25FYIA antibody.

Embodiment 55

The antibody of embodiment 50, wherein said antibody contains at least one light chain variable region of an M25FYIAEG antibody.

Embodiment 56

The antibody of embodiment 50, wherein said antibody contains at least one light chain variable region of an M25FYIADS antibody.

Embodiment 57

The antibody of embodiment 50, wherein said antibody contains at least one light chain variable region of an M25 antibody.

Embodiment 58

The antibody of embodiment 50, wherein said antibody contains at least one light chain variable region of an M25EG antibody.

Embodiment 59

The antibody of embodiment 50, wherein said antibody contains at least one light chain variable region of an M25DS antibody.

Embodiment 60

The antibody of embodiment 50, wherein said antibody contains at least one light chain variable region of an M25AELF antibody.

Embodiment 61

The antibody of embodiment 50, wherein said antibody contains at least one light chain variable region of an M25AELFEG antibody.

Embodiment 62

The antibody of embodiment 50, wherein said antibody contains at least one light chain variable region of an M25AELFDS antibody.

Embodiment 63

The antibody of embodiment 50, wherein said antibody contains at least one light chain variable region of an M25ADL99P antibody.

Embodiment 64

The antibody of embodiment 50, wherein said antibody contains at least one light chain variable region of an M25ADL99G antibody.

Embodiment 65

The antibody of embodiment 50, wherein said antibody contains at least one light chain variable region of an M25ADS95R antibody.

Embodiment 66

The antibody of embodiment 50, wherein said antibody contains at least one light chain variable region of an M25ADD28G antibody.

Embodiment 67

The antibody of embodiment 50, wherein said antibody contains at least one light chain variable region of an M25ADS91G antibody.

Embodiment 68

The antibody of embodiment 50, wherein said antibody contains at least one light chain variable region of an M25ADY93H antibody.

Embodiment 69

The antibody of embodiment 50, wherein said antibody contains at least one light chain variable region of an M25ADYHSRLF antibody.

Embodiment 70

The antibody of embodiment 50, wherein said antibody contains at least one light chain variable region of an M25GRITSGFYGDwtLC antibody.

Embodiment 71

The antibody of embodiment 50, wherein said antibody contains at least one light chain variable region of an M25FSITSGFYGDwtLC antibody.

Embodiment 72

The antibody of embodiment 50, wherein said antibody contains at least one light chain variable region of an M253018IA antibody.

Embodiment 73

The antibody of embodiment 50, wherein said antibody contains at least one light chain variable region of an M253018LF antibody.

Embodiment 74

The antibody of embodiment 50, wherein said antibody contains at least one light chain variable region of an M25AD antibody.

Embodiment 75

The antibody of embodiment 50, wherein said antibody contains at least one light chain variable region of an M25ADX antibody.

Embodiment 76

The antibody of embodiment 50, wherein said antibody contains at least one light chain variable region of an ALPPL2rd3_1 antibody.

Embodiment 77

The antibody of embodiment 50, wherein said antibody contains at least one light chain variable region of an ALPPL2rd3_2 antibody.

Embodiment 78

The antibody of embodiment 50, wherein said antibody contains at least one light chain variable region of an M25AGIA antibody.

Embodiment 79

The antibody of embodiment 50, wherein said antibody contains at least one light chain variable region of an M25AGLF antibody.

Embodiment 80

The antibody of embodiment 50, wherein said antibody contains at least one light chain variable region of an M25ASIA antibody.

Embodiment 81

The antibody of embodiment 50, wherein said antibody contains at least one light chain variable region of an M25ASLF antibody.

Embodiment 82

The antibody of embodiment 50, wherein said antibody contains at least one light chain variable region of an M25ASwt antibody.

Embodiment 83

The antibody of embodiment 50, wherein said antibody contains at least one light chain variable region of an M25AVIA antibody.

Embodiment 84

The antibody of embodiment 50, wherein said antibody contains at least one light chain variable region of an M25AVLF antibody.

Embodiment 85

The antibody of embodiment 50, wherein said antibody contains at least one light chain variable region of an M25ALIA antibody.

Embodiment 86

The antibody of embodiment 50, wherein said antibody contains at least one light chain variable region of an M25ALLF antibody.

Embodiment 87

The antibody of embodiment 50, wherein said antibody contains at least one light chain variable region of an M25wtIA antibody.

Embodiment 88

The antibody of embodiment 50, wherein said antibody contains at least one light chain variable region of an M25wtLF antibody.

Embodiment 89

The antibody according to any one of embodiments 1-8, wherein said antibody comprises a heavy chain variable region (VH) of an M25ADLF antibody and a light chain variable region (VL) of an M25ADLF antibody.

Embodiment 90

The antibody according to any one of embodiments 1-8, wherein said antibody comprises a heavy chain variable region (VH) of an M25ADLFEG antibody and a light chain variable region (VL) of an M25ADLFEG antibody.

Embodiment 91

The antibody according to any one of embodiments 1-8, wherein said antibody comprises a heavy chain variable region (VH) of an M25ADLFDS antibody and a light chain variable region (VL) of an M25ADLFDS antibody.

Embodiment 92

The antibody according to any one of embodiments 1-8, wherein said antibody comprises a heavy chain variable region (VH) of an M25FYIA antibody and a light chain variable region (VL) of an M25FYIA antibody.

Embodiment 93

The antibody according to any one of embodiments 1-8, wherein said antibody comprises a heavy chain variable region (VH) of an M25FYIAEG antibody and a light chain variable region (VL) of an M25FYIAEG antibody.

Embodiment 94

The antibody according to any one of embodiments 1-8, wherein said antibody comprises a heavy chain variable region (VH) of an M25FYIADS antibody and a light chain variable region (VL) of an M25FYIADS antibody.

Embodiment 95

The antibody according to any one of embodiments 1-8, wherein said antibody comprises a heavy chain variable region (VH) of an M25 antibody and a light chain variable region (VL) of an M25 antibody.

Embodiment 96

The antibody according to any one of embodiments 1-8, wherein said antibody comprises a heavy chain variable region (VH) of an M25EG antibody and a light chain variable region (VL) of an M25EG antibody.

Embodiment 97

The antibody according to any one of embodiments 1-8, wherein said antibody comprises a heavy chain variable region (VH) of an M25DS antibody and a light chain variable region (VL) of an M25DS antibody.

Embodiment 98

The antibody according to any one of embodiments 1-8, wherein said antibody comprises a heavy chain variable region (VH) of an M25AELF antibody and a light chain variable region (VL) of an M25AELF antibody.

Embodiment 99

The antibody according to any one of embodiments 1-8, wherein said antibody comprises a heavy chain variable region (VH) of an M25AELFEG antibody and a light chain variable region (VL) of an M25AELFEG antibody.

Embodiment 100

The antibody according to any one of embodiments 1-8, wherein said antibody comprises a heavy chain variable region (VH) of an M25AELFDS antibody and a light chain variable region (VL) of an M25AELFDS antibody.

Embodiment 101

The antibody according to any one of embodiments 1-8, wherein said antibody comprises a heavy chain variable region (VH) of an M25ADL99P antibody and a light chain variable region (VL) of an M25ADL99P antibody.

Embodiment 102

The antibody according to any one of embodiments 1-8, wherein said antibody comprises a heavy chain variable region (VH) of an M25ADL99G antibody and a light chain variable region (VL) of an M25ADL99G antibody.

Embodiment 103

The antibody according to any one of embodiments 1-8, wherein said antibody comprises a heavy chain variable

13 region (VH) of an M25ADS95R antibody and a light chain variable region (VL) of an M25ADS95R antibody.

Embodiment 104

The antibody according to any one of embodiments 1-8, wherein said antibody comprises a heavy chain variable region (VH) of an M25ADD28G antibody and a light chain variable region (VL) of an M25ADD28G antibody.

Embodiment 105

The antibody according to any one of embodiments 1-8, wherein said antibody comprises a heavy chain variable region (VH) of an M25ADS91G antibody and a light chain variable region (VL) of an M25ADS91G antibody.

Embodiment 106

The antibody according to any one of embodiments 1-8, wherein said antibody comprises a heavy chain variable region (VH) of an M25ADY93H antibody and a light chain variable region (VL) of an M25ADY93H antibody.

Embodiment 107

The antibody according to any one of embodiments 1-8, wherein said antibody comprises a heavy chain variable region (VH) of an M25ADYHSRLF antibody and a light chain variable region (VL) of an M25ADYHSRLF antibody.

Embodiment 108

The antibody according to any one of embodiments 1-8, wherein said antibody comprises a heavy chain variable region (VH) of an M25GRITSGFYGDwtLC antibody and a light chain variable region (VL) of an M25GRITSGFYGDwtLC antibody.

Embodiment 109

The antibody according to any one of embodiments 1-8, wherein said antibody comprises a heavy chain variable region (VH) of an M25FSITSGFYGDwtLC antibody and a light chain variable region (VL) of an M25FSITSGFYGDwtLC antibody.

Embodiment 110

The antibody according to any one of embodiments 1-8, wherein said antibody comprises a heavy chain variable region (VH) of an M253018IA antibody and a light chain variable region (VL) of an M253018IA antibody.

Embodiment 111

The antibody according to any one of embodiments 1-8, wherein said antibody comprises a heavy chain variable region (VH) of an M253018LF antibody and a light chain variable region (VL) of an M253018LF antibody.

Embodiment 112

The antibody according to any one of embodiments 1-8, wherein said antibody comprises a heavy chain variable region (VH) of an M25AD antibody and a light chain variable region (VL) of an M25AD antibody.

14

Embodiment 113

The antibody according to any one of embodiments 1-8, wherein said antibody comprises a heavy chain variable region (VH) of an M25ADX antibody and a light chain variable region (VL) of an M25ADX antibody.

Embodiment 114

The antibody according to any one of embodiments 1-8, wherein said antibody comprises a heavy chain variable region (VH) of an ALPPL2rd3_1 antibody and a light chain variable region (VL) of an ALPPL2rd3_1 antibody.

Embodiment 115

The antibody according to any one of embodiments 1-8, wherein said antibody comprises a heavy chain variable region (VH) of an ALPPL2rd3_2 antibody and a light chain variable region (VL) of an ALPPL2rd3_2 antibody.

Embodiment 116

The antibody according to any one of embodiments 1-8, wherein said antibody comprises a heavy chain variable region (VH) of an M25AGIA antibody and a light chain variable region (VL) of an M25AGIA antibody.

Embodiment 117

The antibody according to any one of embodiments 1-8, wherein said antibody comprises a heavy chain variable region (VH) of an M25AGLF antibody and a light chain variable region (VL) of an M25AGLF antibody.

Embodiment 118

The antibody according to any one of embodiments 1-8, wherein said antibody comprises a heavy chain variable region (VH) of an M25ASIA antibody and a light chain variable region (VL) of an M25ASIA antibody.

Embodiment 119

The antibody according to any one of embodiments 1-8, wherein said antibody comprises a heavy chain variable region (VH) of an M25ASLF antibody and a light chain variable region (VL) of an M25ASLF antibody.

Embodiment 120

The antibody according to any one of embodiments 1-8, wherein said antibody comprises a heavy chain variable region (VH) of an M25ASwt antibody and a light chain variable region (VL) of an M25ASwt antibody.

Embodiment 121

The antibody according to any one of embodiments 1-8, wherein said antibody comprises a heavy chain variable region (VH) of an M25AVIA antibody and a light chain variable region (VL) of an M25AVIA antibody.

Embodiment 122

The antibody according to any one of embodiments 1-8, wherein said antibody comprises a heavy chain variable region (VH) of an M25AVLF antibody and a light chain variable region (VL) of an M25AVLF antibody.

Embodiment 123

The antibody according to any one of embodiments 1-8, wherein said antibody comprises a heavy chain variable region (VH) of an M25ALIA antibody and a light chain variable region (VL) of an M25ALIA antibody.

Embodiment 124

The antibody according to any one of embodiments 1-8, wherein said antibody comprises a heavy chain variable region (VH) of an M25ALLF antibody and a light chain variable region (VL) of an M25ALLF antibody.

Embodiment 125

The antibody according to any one of embodiments 1-8, wherein said antibody comprises a heavy chain variable region (VH) of an M25wtIA antibody and a light chain variable region (VL) of an M25wtIA antibody.

Embodiment 126

The antibody according to any one of embodiments 1-8, wherein said antibody comprises a heavy chain variable region (VH) of an M25wtLF antibody and a light chain variable region (VL) of an M25wtLF antibody.

Embodiment 127

The antibody according to any one of embodiments 1-126, wherein said antibody is a substantially intact immunoglobulin.

Embodiment 128

The antibody of embodiment 127, wherein said antibody comprises an IgA, IgE, or IgG.

Embodiment 129

The antibody of embodiment 127, wherein said antibody comprises an IgG.

Embodiment 130

The antibody of embodiment 127, wherein said antibody comprises an IgG1.

Embodiment 131

The antibody according to any one of embodiments 1-126, wherein said antibody is an antibody fragment that specifically binds cells that express ALPP and/or ALPPL2.

Embodiment 132

The antibody of embodiment 131, wherein said antibody is an antibody fragment selected from the group consisting of Fv, Fab, (Fab')$_2$, (Fab')$_3$, IgG$\Delta$CH2, and a minibody.

Embodiment 133

The antibody according to any one of embodiments 1-126, wherein said antibody is a single chain antibody.

Embodiment 134

The of embodiment 133 wherein said antibody is a human scFv.

Embodiment 135

The antibody of embodiment 134, wherein said heavy chain variable region is joined to said light chain variable region by a linker comprising or consisting of the amino acid sequence (Gly$_4$Ser)$_3$ (SEQ ID NO:82).

Embodiment 136

An immunoconjugate comprising an antibody according to any one of embodiments 1-135 attached to an effector wherein said effector is selected from the group consisting of a second antibody, a detectable label, a cytotoxin or cytostatic agent, a liposome containing a drug, a radionuclide, a drug, a prodrug, an immune modulator, a viral particle, a cytokine, a second antibody, and a chelate.

Embodiment 137

The immunoconjugate of embodiment 136, wherein said antibody is attached to a cytotoxic and/or cytostatic drug.

Embodiment 138

The immunoconjugate of embodiment 136, wherein said antibody is attached directly or through a linker to one or more of the following: said drug a lipid or liposome containing said drug; a polymeric drug carrier comprising said drug; and a nanoparticle drug carrier comprising said drug.

Embodiment 139

The immunoconjugate according to any one of embodiments 137-138, wherein said drug is an anti-cancer drug.

Embodiment 140

The immunoconjugate according to any one of embodiments 137-138, wherein said drug is selected from the group consisting of a microtubule inhibitor, a DNA-damaging agents, and a polymerase inhibitor.

Embodiment 141

The immunoconjugate of embodiment 140, wherein the drug comprises a tubulin inhibitor.

Embodiment 142

The immunoconjugate of embodiment 141, wherein the drug comprises a drug selected from the group consisting of an auristatin, Dolastatin-10, synthetic derivatives of the natural product Dolastatin-10, and maytansine or a maytansine derivative.

Embodiment 143

The immunoconjugate of embodiment 141, wherein the drug comprises a drug selected from the group consisting Monomethylauristatin F (MMAF), Auristatin E (AE), Monomethylauristatin E (MMAE), vcMMAE, and vcMMAF.

Embodiment 144

The immunoconjugate of embodiment 141, wherein the drug comprises a maytansine selected from the group consisting of Mertansine (DM1), DM3, and DM4.

Embodiment 145

The immunoconjugate of embodiment 140, wherein the drug comprises a DNA-damaging agent.

Embodiment 146

The immunoconjugate of embodiment 145, wherein the drug comprises a drug selected from the group consisting of a calicheamicin, a duocarmycin, and a pyrrolobenzodiazepines.

Embodiment 147

The immunoconjugate of embodiment 146, wherein the drug comprises a calicheamicin or a calicheamicin analog.

Embodiment 148

The immunoconjugate of embodiment 146, wherein the drug comprises a duocarmycin.

Embodiment 149

The immunoconjugate of embodiment 148, wherein the drug comprises a duocarmycin, selected from the group consisting of duocarmycin A, duocarmycin B 1, duocarmycin B2, duocarmycin C1, duocarmycin C2, duocarmycin D, duocarmycin SA, Cyclopropylbenzoindole duocarmycin (CC-1065), Centanamycin, Rachelmycin, Adozelesin, Bizelesin, and Carzelesin.

Embodiment 150

The immunoconjugate of embodiment 146, wherein the drug comprises a pyrrolobenzodiazepine or a pyrrolobenzodiazepine dimer.

Embodiment 151

The immunoconjugate of embodiment 150, wherein the drug comprise a drug selected from the group consisting of Anthramycin (and dimers thereof), Mazethramycin (and dimers thereof), Tomaymycin (and dimers thereof), Prothracarcin (and dimers thereof), Chicamycin (and dimers thereof), Neothramycin A (and dimers thereof), Neothramycin B (and dimers thereof), DC-81 (and dimers thereof), Sibiromycin (and dimers thereof), Porothramycin A (and dimers thereof), Porothramycin B (and dimers thereof), Sibanomycin (and dimers thereof), Abbeymycin (and dimers thereof), SG2000, and SG2285.

Embodiment 152

The immunoconjugate according to any one of embodiments 137-138, wherein said drug is selected from the group consisting of auristatin, dolastatin, colchicine, combretastatin, and mTOR/PI3K inhibitors.

Embodiment 153

The immunoconjugate according to any one of embodiments 137-138, wherein said drug is selected from the group consisting of flourouracil (5-FU), capecitabine, 5-trifluoromethyl-2'-deoxyuridine, methotrexate sodium, raltitrexed, pemetrexed, cytosine Arabinoside, 6-mercaptopurine, azathioprine, 6-thioguanine (6-TG), pentostatin, fludarabine phosphate, cladribine, floxuridine (5-fluoro-2), ribonucleotide reductase inhibitor (RNR), cyclophosphamide, neosar, ifosfamide, thiotepa, 1,3-bis(2-chloroethyl)-1-nitosourea (BCNU), 1,-(2-chloroethyl)-3-cyclohexyl-lnitrosourea, methyl (CCNU), hexamethylmelamine, busulfan, procarbazine HCL, dacarbazine (DTIC), chlorambucil, melphalan, cisplatin, carboplatin, oxaliplatin, bendamustine, carmustine, chloromethine, dacarbazine (DTIC), fotemustine, lomustine, mannosulfan, nedaplatin, nimustine, prednimustine, ranimustine, satraplatin, semustine, streptozocin, temozolomide, treosulfan, triaziquone, triethylene melamine, thioTEPA, triplatin tetranitrate, trofosfamide, uramustine, doxorubicin, daunorubicin citrate, mitoxantrone, actinomycin D, etoposide, topotecan HCL, teniposide (VM-26), irinotecan HCL (CPT-11), camptothecin, belotecan, rubitecan, vincristine, vinblastine sulfate, vinorelbine tartrate, vindesine sulphate, paclitaxel, docetaxel, nanoparticle paclitaxel, abraxane, ixabepilone, larotaxel, ortataxel, tesetaxel, vinflunine, retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol. In certain embodiments the anti-cancer compound is selected from the group consisting of abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, and zoledronic acid.

Embodiment 154

The immunoconjugate of embodiment 136, wherein said antibody is attached to a cytotoxin.

Embodiment 155

The immunoconjugate of embodiment 154, wherein said antibody is attached to a cytotoxin selected from the group consisting of a Diphtheria toxin, a Pseudomonas exotoxin, a ricin, an abrin, saporin, and a thymidine kinase.

Embodiment 156

The immunoconjugate of embodiment 136, wherein said antibody is attached to an immunmodulator.

Embodiment 157

The immunoconjugate of embodiment 156, wherein said immunomodulator comprises a second antibody.

Embodiment 158

The immunoconjugate of embodiment 157, wherein said second antibody comprise an anti-CD3 antibody.

Embodiment 159

The immunoconjugate of embodiment 156, wherein said immunomodulator is an immunomodulatory is one that blocks immune checkpoints.

Embodiment 160

The immunoconjugate of embodiment 159, wherein said immuinomodulator effector an antibody that is selected from

19 the group consisting of an anti-CTLA4 antibody, an anti-PDL1 antibody, an anti-PDL2 antibody, an anti-ICOS antibody, and an anti-BTLA antibody.

Embodiment 161

The immunoconjugate of embodiment 160, wherein said antibody is an antibody that comprise the VH and VL domains of an antibody selected from the group consisting of ipilimumab, nivolumab, and pembrolizumab.

Embodiment 162

The immunoconjugate of embodiment 160, wherein said antibody is an antibody selected from the group consisting of ipilimumab, nivolumab, and pembrolizumab.

Embodiment 163

The immunoconjugate of embodiment 136, wherein said antibody is attached to a chelate comprising an isotope selected from the group consisting $^{99}$Tc, $^{99}$Tc, $^{97}$Ru, $^{95}$Ru, $^{94}$Tc, $^{90}$Y, $^{90}$Y, $^{89}$Zr, $^{86}$Y, $^{77}$Br, $^{77}$As, $^{76}$Br, $^{75}$Se, $^{72}$As, $^{68}$Ga, $^{68}$Ga, $^{67}$Ga, $^{67}$Ga, $^{67}$Cu, $^{67}$Cu, $^{64}$Cu, $^{62}$Cu, $^{62}$Cu, $^{59}$Cu, $^{58}$Co, $^{57}$Co, $^{52}$Mn, $^{52}$Fe, $^{51}$Cr, $^{47}$Sc, $^{3}$H, $^{35}$S, $^{33}$P, $^{32}$P, $^{225}$Ac, $^{224}$Ac, $^{223}$Ra, $^{213}$Bi, $^{212}$Pb, $^{212}$Bi, $^{211}$At, $^{203}$Pb, $^{203}$Hg, $^{201}$Tl, $^{199}$Au, $^{198}$Au, $^{198}$Au, $^{197}$Pt, $^{18}$F, $^{189}$Re, $^{188}$Re, $^{188}$Re, $^{186}$Re, $^{186}$Re, $^{177}$Lu, $^{177}$Lu, $^{175}$Yb, $^{172}$Tm, $^{169}$Yb, $^{169}$Yb, $^{169}$Er, $^{168}$Tm, $^{167}$Tm, $^{166}$Ho, $^{166}$Dy, $^{165}$Tm, $^{165}$Dy, $^{161}$Tb, $^{15}$O, $^{15}$N, $^{159}$Gd, $^{157}$Gd, $^{153}$Sm, $^{153}$Pb, $^{151}$Pm, $^{14}$C, $^{149}$Pm, $^{143}$Pr, $^{142}$Pr, $^{13}$N, $^{133}$I, $^{131}$In, $^{131}$I, $^{127}$Te, $^{126}$I, $^{125}$Te, $^{125}$I, $^{124}$I, $^{123}$I, $^{122}$Te, $^{121}$Te, $^{121}$Sn, $^{11}$C, $^{113}$In, $^{111}$In, $^{111}$In, $^{111}$Ag, $^{111}$Ag, $^{109}$Pd, $^{109}$Pd, $^{107}$Hg, $^{105}$Ru, $^{105}$Rh, $^{105}$Rh, and $^{103}$Ru.

Embodiment 164

The immunoconjugate of embodiment 136, wherein said antibody is attached to a lipid or a liposome complexed with or containing an anti-cancer drug.

Embodiment 165

The immunoconjugate of embodiment 136, wherein said antibody is attached to a detectable label.

Embodiment 166

A pharmaceutical formulation said formulation comprising: a pharmaceutically acceptable carrier and an antibody according to any one of embodiments 1-135; and/or a pharmaceutically acceptable carrier and a immunoconjugate according to any one of embodiments 136-165.

Embodiment 167

The pharmaceutical formulation of embodiment 166, wherein said formulation is a unit dosage formulation.

Embodiment 168

The formulation according to any one of embodiments 166-167, wherein said formulation is formulated for administration via a route selected from the group consisting of oral administration, nasal administration, rectal administration, intraperitoneal injection, intravascular injection, subcutaneous injection, transcutaneous administration, and intramuscular injection.

20

Embodiment 169

A method of reducing tumor initiating cells in a cell population, the method comprising contacting a cell population, wherein the population comprises tumor initiating cells that express ALPPL2 and cells other than tumor initiating cells, with an anti-ALPPL2 immunoconjugate according to any one of embodiments 136-164, wherein the effector comprising said immunoconjugate has cytostatic and/or cytotoxic activity and/or immunomodulatory activity, whereby the frequency of tumor initiating cells in the tumor cell population is reduced.

Embodiment 170

The method of embodiment 169, wherein the contacting is performed in vivo.

Embodiment 171

The method of embodiment 169, wherein the contacting is performed in vitro.

Embodiment 172

A method of inhibiting the growth and/or proliferation of a cell that expresses ALPPL2, said method comprising: contacting said cell with an antibody according to any one of embodiments 1-135; and/or contacting said cell with an anti-ALPPL2 immunoconjugate according to any one of embodiments 136-164, wherein the effector comprising said immunoconjugate has cytostatic and/or cytotoxic activity and/or immunomodulatory activity.

Embodiment 173

The method of embodiment 172, wherein said cell is a cancer cell.

Embodiment 174

The method of embodiment 173, wherein said cancer cell is selected from the group consisting of mesothelioma, testicular cancer, endometrial cancer, and subsets of ovarian, pancreatic, and non small cell lung cancers.

Embodiment 175

The method according to any one of embodiments 173-174, wherein said cell is a metastatic cell.

Embodiment 176

The method according to any one of embodiments 173-175, wherein said cell is a solid tumor cell.

Embodiment 177

The method according to any one of embodiments 172-176, wherein said effector comprises a radionuclide and/or a cytostatic drug.

Embodiment 178

The method of embodiment 177, wherein said effector comprises one or more of the following: a cytotoxic and/or cytostatic drug; a lipid or liposome containing a cytotoxic and/or cytostatic drug; a polymeric drug carrier comprising a cytotoxic and/or cytostatic drug; and a nanoparticle drug carrier comprising a cytotoxic and/or cytostatic drug.

Embodiment 179

The method of embodiment 178, wherein said drug is an anti-cancer drug.

Embodiment 180

The method of embodiment 179, wherein said drug is selected from the group consisting of auristatin, dolastatin, colchicine, combretastatin, and mTOR/PI3K inhibitors.

Embodiment 181

The method of embodiment 179, wherein said drug is monomethyl auristatin F.

Embodiment 182

The method of embodiment 179, wherein said drug is selected from the group consisting of flourouracil (5-FU), capecitabine, 5-trifluoromethyl-2'-deoxyuridine, methotrexate sodium, raltitrexed, pemetrexed, cytosine Arabinoside, 6-mercaptopurine, azathioprine, 6-thioguanine (6-TG), pentostatin, fludarabine phosphate, cladribine, floxuridine (5-fluoro-2), ribonucleotide reductase inhibitor (RNR), cyclophosphamide, neosar, ifosfamide, thiotepa, 1,3-bis(2-chloroethyl)-1-nitrosourea (BCNU), 1,-(2-chloroethyl)-3-cyclohexyl-lnitrosourea, methyl (CCNU), hexamethylmelamine, busulfan, procarbazine HCL, dacarbazine (DTIC), chlorambucil, melphalan, cisplatin, carboplatin, oxaliplatin, bendamustine, carmustine, chloromethine, dacarbazine (DTIC), fotemustine, lomustine, mannosulfan, nedaplatin, nimustine, prednimustine, ranimustine, satraplatin, semustine, streptozocin, temozolomide, treosulfan, triaziquone, triethylene melamine, thioTEPA, triplatin tetranitrate, trofosfamide, uramustine, doxorubicin, daunorubicin citrate, mitoxantrone, actinomycin D, etoposide, topotecan HCL, teniposide (VM-26), irinotecan HCL (CPT-11), camptothecin, belotecan, rubitecan, vincristine, vinblastine sulfate, vinorelbine tartrate, vindesine sulphate, paclitaxel, docetaxel, nanoparticle paclitaxel, abraxane, ixabepilone, larotaxel, ortataxel, tesetaxel, vinflunine, retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol. In certain embodiments the anti-cancer compound is selected from the group consisting of abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, and zoledronic acid.

Embodiment 183

The method according to any one of embodiments 178-182, wherein: said drug is conjugated directly to said antibody; or said drug is contained in a lipid or liposome attached to said antibody; or said drug is contained in a polymeric and/or nanoparticle carrier attached to said antibody.

Embodiment 184

The method according to any one of embodiments 172-176, wherein said effector comprises a cytotoxin.

Embodiment 185

The method of embodiment 172, wherein said effector comprises a radionuclide.

Embodiment 186

The method according to any one of embodiments 172-185, wherein said immunoconjugate or antibody is administered in a pharmaceutical composition comprising a pharmaceutical acceptable carrier.

Embodiment 187

The method according to any one of embodiments 172-186, wherein said administering comprises administering to a human or to a non-human mammal.

Embodiment 188

The method according to any one of embodiments 172-187, wherein said administering comprises: administering parenterally; and/or administering into a tumor or a surgical site.

Embodiment 189

The method according to any one of embodiments 172-188, wherein said antibody and/or immunoconjugate is administered as an adjunct therapy to surgery and/or radiotherapy.

Embodiment 190

The method according to any one of embodiments 172-189, wherein said antibody and/or immunoconjugate is administered in conjunction with another anti-cancer drug and/or a hormone.

Embodiment 191

A method of detecting a cancer cell of a cancer that expresses ALPPL2, said method comprising: contacting said cancer cell with a immunoconjugate comprising an antibody according to any one of embodiments 1-135 attached to a detectable label; and detecting the presence and/or location of said detectable label where the presence and/or location is an indicator of the location and/or presence of a cancer cell.

Embodiment 192

The method of embodiment 191, wherein said label comprises a label selected from the group consisting of a radioactive label, a radioopaque label, an MRI label, a PET label, and an SPECT label.

Embodiment 193

The method according to any one of embodiments 191-192, wherein said cancer cell is selected from the group consisting of mesothelioma, testicular cancer, endometrial cancer, and subsets of ovarian, pancreatic, and non small cell lung cancers.

Embodiment 194

The method according to any one of embodiments 191-193, wherein said contacting comprises administering said immunoconjugate to a non-human mammal or to a human.

Embodiment 195

The method according to any one of embodiments 191-194, wherein said detecting comprises detecting said label in vivo.

Embodiment 196

The method of embodiment 195, wherein said detecting comprises using a detection method selected from the group consisting of X-ray, PET, SPECT, MRI, and CAT.

Embodiment 197

The method according to any one of embodiments 191-194, wherein said detecting comprises detecting said label ex vivo in a biopsy or a sample derived from a biopsy.

Embodiment 198

A nucleic acid encoding an antibody or a fragment of an antibody according to any of embodiments 1-135.

Embodiment 199

An expression vector comprising the nucleic acid of embodiment 198.

Embodiment 200

A cell comprising the expression vector of embodiment 199.

Embodiment 201

A chimeric antigen receptor (CAR) comprising an antibody according to any one of embodiments 1-135.

Embodiment 202

The chimeric antigen receptor of embodiment 201, wherein said receptor comprises: said antibody; a transmembrane domain; at least one costimulatory signaling region; and a CD3 zeta signaling domain.

Embodiment 203

The chimeric antigen receptor of embodiment 202, wherein said costimulatory signaling region comprises the intracellular domain of a costimulatory molecule selected from the group consisting of CD27, CD2S, 4-I BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

Embodiment 204

The chimeric antigen receptor of embodiment 202, wherein said costimulatory signaling region comprises 4-1BB.

Embodiment 205

The chimeric antigen receptor according to any one of embodiments 202-204, wherein said transmembrane domain comprise the CD8 hinge domain or a fragment thereof.

Embodiment 206

An isolated nucleic acid sequence encoding a chimeric antigen receptor (CAR) according to any one of embodiments 201-205.

Embodiment 207

A cell comprising a nucleic acid sequence encoding a chimeric antigen receptor (CAR), according to any one of embodiments 201-205.

Embodiment 208

The cell of embodiment 207, wherein said cell is selected from the group consisting of a T cell, a Natural Killer (NK) cell, a cytotoxic T lymphocyte (CTL), and a regulatory T cell.

Embodiment 209

The cell according to any one of embodiments 207-208, wherein the cell exhibits an anti-cancer immune response when the antigen binding domain binds to a cell that expresses ALPP and/or ALPPL2.

Embodiment 210

A pharmaceutical composition for treatment of cancer in a mammal, said formulation comprising a genetically engineered cell (CAR-T cell) according to any one of embodiments 207-209, and a pharmaceutically acceptable carrier.

Embodiment 211

The composition of embodiment 210, wherein said formulation comprises an anti-tumor effective amount of cells, wherein the anti-tumor effective amount of cells ranges from about $10^4$ up to about $10^7$ cells per kg body weight of a mammal in need of such cells.

Embodiment 212

A vector comprising a nucleic acid sequence encoding a chimeric antigen receptor (CAR) according to any one of embodiments 201-205.

Embodiment 213

A method for stimulating a T cell-mediated immune response to a target cell population or tissue in a mammal, wherein said target cell population and/or tissue express ALPP and/or ALPPL2, or a region of ALPP and/or ALPPL2 bound by antibody M25AD, M25ADX and/or M25, said comprising: administering to a mammal an effective amount of a cell genetically modified to express a chimeric antigen receptor (CAR) according to any one of embodiments 201-205.

Embodiment 214

A method of providing an anti-tumor immunity against tumors that express ALPP and/or ALPPL2, and/or a region of ALPP and/or ALPPL2 bound by antibody M25AD, M25ADX and/or M25 in a mammal, the method comprising administering to the mammal an effective amount of a cell genetically modified to express a chimeric antigen receptor (CAR) according to any one of embodiments 201-205, thereby providing an antitumor immunity in the mammal.

Embodiment 215

A method of treating a mammal with a cancer comprising cells that express ALPP and/or ALPPL2, or a region of ALPP and/or ALPPL2 bound by antibody M25AD, M25ADX and/or M25, said method comprising: administering to a mammal an effective amount of a cell genetically modified to express a chimeric antigen receptor (CAR) according to any one of embodiments 201-205.

Embodiment 216

A method of generating a persisting population of genetically engineered T cells in a mammal diagnosed with cancer, said method comprising administering to said mammal a T cell genetically modified to express a chimeric antigen receptor (CAR) according to any one of embodiments 201-205, wherein the persisting population of genetically engineered T cells persists in the human for at least one month after administration.

Embodiment 217

The method of embodiment 216, wherein the persisting population of genetically engineered T cells comprises a memory T cell.

Embodiment 218

The method according to any one of embodiments 216-217, wherein the persisting population of genetically engineered T cells persists in the human for at least three months, or for at least four months, or for at least five months, or for at least six months, or for at least seven months, or for at least eight months, or for at least nine months, or for at least ten months, or for at least eleven months, or for at least twelve months, or for at least two years, or for at least three years after administration.

Embodiment 219

The method according to any one of embodiments 213-215, wherein said cell is a T cell.

Embodiment 220

The method according to any one of embodiments 213-215, wherein said cell is an autologous T cell.

Embodiment 221

The method according to any one of embodiments 213-215, wherein said cell is an allogenic T cell.

Embodiment 222

A method of expanding a population of genetically engineered T cells in a mammal diagnosed with cancer, said method comprising administering to said mammal administering to said mammal a T cell genetically modified to express a chimeric antigen receptor (CAR) according to any one of embodiments 201-205, wherein the administered genetically engineered T cell produces a population of progeny T cells in the human.

Embodiment 223

The method according to any one of embodiments 213-222, wherein said mammal is a human.

Embodiment 224

The method according to any one of embodiments 213-222, wherein said mammal is a non-human mammal.

Embodiment 225

The method according to any one of embodiments 213-224, wherein said cancer comprises cells of a cancer selected from the group consisting of mesothelioma, testicular cancer, endometrial cancer, and ovarian, pancreatic, and non small cell lung cancers that express ALPP and/or ALPPL2.

Embodiment 226

The method according to any one of embodiments 213-225, wherein the administered cell is a T cell.

Embodiment 227

The method according to any one of embodiments 213-226, wherein the administered cell is an autologous T cell.

Embodiment 228

A method for treatment of cancer comprising the steps of contacting a genetically engineered T cell (CAR-T cell) according to embodiment according to any one of embodiments 201-205, wherein with a cancer cell of a mammal, and inducing apoptosis of the cancer cell.

Definitions

The term "patient" includes human and other mammalian subjects that receive either prophylactic or therapeutic treatment.

As used herein, the term "subject" includes any human or non-human animal. For example, the methods and compositions of the present invention can be used to treat a subject having cancer. In one illustrative embodiment, the subject is a human. The term "non-human animal" includes all vertebrates, e.g., mammals and non-mammals, such as non-human primates, sheep, dog, cow, chickens, amphibians, reptiles, etc.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321, O-methylphophoroamidite linkages (see Eckstein, *Oligonucleotides and Analogues: A Practical Approach*, Oxford University Press), and peptide nucleic acid backbones and linkages (see Egholm (1992) *J Am. Chem. Soc.* 114:1895; Meier et al. (1992) *Chem. Int. Ed. Engl.* 31: 1008; Nielsen (1993) *Nature*, 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The term "residue" as used herein refers to natural, synthetic, or modified amino acids.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into a Fab' monomer. The Fab' monomer is essentially a Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Certain preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci. USA*, 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three-dimensional structure substantially similar to the structure of an antigen-binding site are known to those of skill in the art (see e.g., U.S. Pat. Nos. 5,091,513, 5,132,405, and 4,956,778). Particularly preferred antibodies should include all that have been displayed on phage (e.g., scFv, Fv, Fab and disulfide linked Fv (see, e.g., Reiter et al. (1995) *Protein Eng.* 8: 1323-1331).

The term "specifically binds", as used herein, when referring to a biomolecule (e.g., protein, nucleic acid, antibody, etc.), refers to a binding reaction that is determinative of the presence biomolecule in heterogeneous population of molecules (e.g., proteins and other biologics). Thus, under designated conditions (e.g. immunoassay conditions in the case of an antibody or stringent hybridization conditions in the case of a nucleic acid), the specified ligand or antibody binds to its particular "target" molecule and does not bind in a significant amount to other molecules present in the sample.

The phrase "inhibition of proliferation of a cell expressing ALPP and/or ALPPL2" as used herein, refers to the ability of an anti-ALPP/ALPPL2 antibody or immunoconjugate described herein to decrease, preferably to statistically significantly decrease proliferation of a cell expressing ALPP and/or ALPPL2 or a fragment thereof relative to the proliferation in the absence of the antibody or immunoconjugate. In one embodiment, the proliferation of a cell expressing ALPP/ALPPL2 or a fragment thereof (e.g., a cancer cell) may be decreased by at least 10%, or at least 20%, or at least 30%, or at least 40%, or at least 50%, or at least 60%, or at least 70%, or at least 80%, or at least 90%, or 100% when the cells are contacted with the antibody or antigen binding portion thereof or an immunoconjugate described herein, relative to the proliferation measured in the absence of the antibody or antigen binding portion thereof or immunoconjugate (control). Cellular proliferation can be assayed using art recognized techniques which measure rate of cell division, the fraction of cells within a cell population undergoing cell division, and/or rate of cell loss from a cell population due to terminal differentiation or cell death (e.g., using a cell titer glow assay or thymidine incorporation).

The phrase "inhibition of the migration of cells expressing ALPP/ALPPL2" as used herein, refers to the ability of an anti-ALPP/ALPPL2 antibody or an antigen-binding portion thereof or an immunoconjugate described herein to decrease, preferably to statistically significantly decrease the migration of a cell expressing ALPP and/or ALPPL2 and/or a fragment thereof (e.g. a fragment bound by M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF) relative to the migration of the cell in the absence of the antibody. In one embodiment, the migration of a cell expressing ALPP/ALPPL2 (e.g., a cancer cell) may be decreased by at least 10%, or at least 20%, or at least 30%, or at least 40%, or at least 50%, or at least 60%, or at least 70%, or at least 80%, or at least 90%, or 100% when the cells are contacted with the antibody or antigen binding portion thereof or immunoconjugate thereof, relative to cell migration measured in the absence of the antibody or antigen binding portion thereof or immunoconjugate thereof (control). Cell migration can be assayed using art recognized techniques. In various embodiments, it is contemplated that the antibodies and/or the immunoconjugates thereof described herein can inhibit the migration of cells (e.g., cancer cells as described herein) expressing or overexpressing ALPP and/or ALPPL2, and/or a domain of ALPP and/or ALPPL2 bound by M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF.

The term "antigen-binding portion" of an antibody (or simply "antibody portion"), as used herein, refers to one or more fragments of an antibody that retain the ability to specifically bind to an antigen (e.g., ALPP and/or ALPPL2). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb including VH and VL domains; (vi) a dAb fragment (see, e.g., Ward et al. (1989) *Nature* 341: 544-546), which consists of a $V_H$ domain; (vii) a dAb which consists of a $V_H$ or a $V_L$ domain; and (viii) an isolated complementarity determining region (CDR) or (ix) a combination of two or more isolated CDRs which may optionally be joined by a synthetic linker. Furthermore, although the two domains of the Fv fragment, $V_L$ and $V_H$, can be coded for by separate genes, they can be joined, using recombinant methods, by a synthetic linker that enables them to be made as a single protein chain in which the $V_L$ and V-regions pair to form monovalent molecules (known as single chain Fv (scFv); see e.g., Bird et al. (1988) *Science* 242: 423-426; and Huston et al. (1988) *Proc. Natl. Acad. Sci. USA* 85: 5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. Monoclonal antibodies can be prepared using any art recognized technique and those described herein such as, for example, a hybridoma method, as described by Kohler et al. (1975) *Nature*, 256: 495, a transgenic animal, as described by, for example, (see e.g., Lonberg, et al. (1994) *Nature* 368(6474): 856-859), recombinant DNA methods (see, e.g., U.S. Pat. No. 4,816,567), or using phage antibody libraries using the techniques described in, for example, Clackson et al. (1991) *Nature*, 352: 624-628, and Marks et al. (1991) *J. Mol. Biol.*, 222: 581-597. Monoclonal antibodies include chimeric antibodies, human antibodies and humanized antibodies and may occur naturally or be recombinantly produced.

The term "recombinant antibody," refers to antibodies that are prepared, expressed, created or isolated by recombinant means, such as (a) antibodies isolated from an animal (e.g., a mouse) that is transgenic or transchromosomal for immunoglobulin genes (e.g., human immunoglobulin genes) or a hybridoma prepared therefrom, (b) antibodies isolated from a host cell transformed to express the antibody, e.g., from a transfectoma, (c) antibodies isolated from a recombinant, combinatorial antibody library (e.g., containing human antibody sequences) using phage display, and (d) antibodies prepared, expressed, created or isolated by any other means that involve splicing of immunoglobulin gene sequences (e.g., human immunoglobulin genes) to other DNA sequences. Such recombinant antibodies may have variable and constant regions derived from human germline immunoglobulin sequences. In certain embodiments, however, such recombinant human antibodies can be subjected to in vitro mutagenesis and thus the amino acid sequences of the $V_H$ and $V_L$ regions of the recombinant antibodies are sequences that, while derived from and related to human germline V- and $V_L$ sequences, may not naturally exist within the human antibody germline repertoire in vivo.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species.

The term "human antibody," as used herein, is intended to include antibodies having variable regions in which both the framework and CDR regions are derived from human germline immunoglobulin sequences as described, for example, by Kabat et al. (See Kabat, et al. (1991) Sequences of proteins of Immunological Interest, Fifth Edition, U.S. Department of Health and Human Services, NIH Publication No. 91-3242). Furthermore, if the antibody contains a constant region, the constant region also is derived from human germline immunoglobulin sequences. The human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The human antibody can have at least one or more amino acids replaced with an amino acid residue, e.g., an activity enhancing amino acid residue which is not encoded by the human germline immunoglobulin sequence. Typically, the human antibody can have up to twenty positions replaced with amino acid residues which are not part of the human germline immunoglobulin sequence. In one particular embodiment, these replacements are within the CDR regions as described in detail below.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

As used herein, a "heterologous antibody" is defined in relation to the transgenic non-human organism or plant producing such an antibody.

An "isolated antibody," as used herein, is intended to refer to an antibody that is substantially free of other antibodies having different antigenic specificities (e.g., an isolated antibody that specifically binds to ALPP and/or ALPL2 is substantially free of antibodies that specifically bind antigens other than ALPP and/or ALPPL2). In addition, an isolated antibody is typically substantially free of other cellular material and/or chemicals. In one embodiment, a combination of "isolated" monoclonal antibodies having different ALPP/ALPPL2 binding specificities are combined in a well-defined composition.

As used herein, "isotype" refers to the antibody class (e.g., IgM or IgG1) that is encoded by heavy chain constant region genes. In one embodiment, an antibody or antigen binding portion thereof is of an isotype selected from an IgG1, an IgG2, an IgG3, an IgG4, an IgM, an IgA1, an IgA2, an IgAsec, an IgD, or an IgE antibody isotype. In some embodiments, a monoclonal antibody of the invention is of the IgG1 isotype. In other embodiments, a monoclonal antibody of the invention is of the IgG2 isotype.

An "antigen" is an entity (e.g., a proteinaceous entity or peptide) to which an antibody or antigen-binding portion thereof binds. In various embodiments of the present invention, an antigen is ALPP and/or ALPPL2, and/or a domain of ALPP and/or ALPPL2 bound by M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF, e.g., as presented on a cell (e.g., an ALPPL2 positive cancer cell).

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art and those described herein, for example, x-ray crystallography and 2-dimensional nuclear magnetic resonance (see, e.g., Epitope Mapping Protocols in Methods in Molecular Biology, Vol. 66, G. E. Morris, Ed. (1996)).

Also contemplated herein are antibodies that bind the same or an overlapping epitope as the M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF antibodies described herein. Antibodies that recognize the same epitope can be identified using routine techniques such as an immunoassay, for example, by showing the ability of one antibody to block the binding of another antibody to a target antigen, i.e., a competitive binding assay. Competitive binding is determined in an assay in which the immunoglobulin under test inhibits specific binding of a reference antibody to a common antigen, such as ALPP and/or ALPPL2. Numerous types of competitive binding assays are known, for example: solid phase direct or indirect radioimmunoassay (RIA), solid phase direct or indirect enzyme immunoassay (EIA), sandwich competition assay (see, e.g., Stahli et al. (1983) *Meth. Enzymol.,* 9: 242); solid phase direct biotin-avidin EIA (see Kirkland et al., (1986) *J. Immunol.* 137: 3614); solid phase direct labeled assay, solid phase direct labeled sandwich assay (see, e.g., Harlow and Lane (1988) *Antibodies: A Laboratory Manual,* Cold Spring Harbor Press); solid phase direct label RIA using, e.g., $^{125}$I label (see, e.g., Morel et al., (1988) *Mol. Immunol.* 25(1): 7); solid phase direct biotin-avidin EIA (Cheung et al. (1990) *Virology* 176: 546); and direct labeled RIA. (Moldenhauer et al. (1990) *Scand J. Immunol.* 32: 77). Typically, such an assay involves the use of purified antigen (e.g., APPL and/or APPL2) bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

As used herein, the terms "specific binding," "specifically binds," "selective binding," and "selectively binds," mean that an antibody or antigen-binding portion thereof, exhibits appreciable affinity for a particular antigen or epitope and, generally, does not exhibit significant cross-reactivity with other antigens and epitopes. "Appreciable" or preferred binding includes binding with an affinity of at least (KD equal to or less than) $10^{-6}$ M, $10^{-7}$ M, $10^{-8}$ M, $10^{-9}$ M, $10^{-10}$ M, or $10^{-11}$ M. Affinities greater than $10^{-9}$ M, preferably greater than $10^{-10}$ M are more preferred. Values intermediate of those set forth herein are also intended to be within the scope of the present invention and a preferred binding affinity can be indicated as a range of affinities, for example, $10^{-6}$ M to $10^{-11}$ M, preferably $10^{-7}$ M or $10^{-8}$ M to $10^{-10}$ M. An antibody that "does not exhibit significant cross-reactivity" is one that will not appreciably bind to an undesirable entity (e.g., an undesirable proteinaceous entity). For example, in one embodiment, an antibody or antigen-binding portion thereof that specifically binds to ALPP and/or ALPPL2 but will not significantly react with other molecules and ALPP/ALPPL2 proteins or peptides. Specific or selective binding can be determined according to any art-recognized means for determining such binding, including, for example, according to Scatchard analysis and/or competitive binding assays.

The term "$K_D$," as used herein, is intended to refer to the dissociation equilibrium constant of a particular antibody-antigen interaction or the affinity of an antibody for an antigen. In one embodiment, the antibody or antigen binding portion thereof according to the present invention binds an antigen (e.g., ALPP and/or ALPPL2) or a cell expressing the antigen with an affinity ($K_D$) of 5 nM or better (i.e., or less) (e.g., 40 nM or 30 nM or 20 nM or 10 nM or less), as measured using a surface plasmon resonance assay or a cell binding assay. In a particular embodiment, an antibody or antigen binding portion thereof according to the present invention binds ALPP and/or ALPPL2, and/or a domain of ALPP and/or ALPPL2 bound by M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF with an affinity ($K_D$) of 5 nM or better (e.g., 4 nM, 2 nM, 1.5 nM, 1.4 nM, 1.3 nM, 1 nM or less), as measured by a surface plasmon resonance assay or a cell binding assay. In other embodiments, an antibody or antigen binding portion thereof binds an antigen (e.g., ALPP and/or ALPPL2) with an affinity ($K_D$) of approximately less than $10^{-10}$ M, or $100 \times 10^{-11}$ M, or $10 \times 10^{-11}$ M, or even lower using live prostate tumor cells by FACS.

The term "$K_{off}$," as used herein, is intended to refer to the off rate constant for the dissociation of an antibody from the antibody/antigen complex.

The term "EC50," as used herein, refers to the concentration of an antibody or an antigen-binding portion thereof or an immunoconjugate described herein, that induces a response, either in an in vitro or an in vivo assay, which is 50% of the maximal response, i.e., halfway between the maximal response and the baseline.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "modifying," or "modification," as used herein, is intended to refer to changing one or more amino acids in the antibodies or antigen-binding portions thereof. The change can be produced by adding, substituting or deleting an amino acid at one or more positions. The change can be produced using known techniques, such as PCR mutagenesis. For example, in some embodiments, an antibody or an antigen-binding portion thereof identified' using the methods of the invention can be modified, to thereby modify the binding affinity of the antibody or antigen-binding portion thereof to ALPP/ALPPL2.

In certain embodiments "conservative amino acid substitutions" in the sequences of the anti-ALPP/ALPPL2 antibodies described herein, i.e., nucleotide and amino acid sequence modifications that do not abrogate the binding of the antibody encoded by the nucleotide sequence or containing the amino acid sequence, to the antigen, e.g., ALPP/ALPPL2 are contemplated. Conservative amino acid substitutions include the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution. Thus, a predicted nonessential amino acid residue in an anti-ALPP/ALPPL2 antibody is preferably replaced with another amino acid residue from the same class. Methods of identifying nucleotide and amino acid conservative substitutions that do not eliminate antigen binding are well-known in the art (see, e.g., Brummell et al. (1993) *Biochem.* 32: 1180-1187; Kobayashi et al. (1999) *Protein Eng.* 12(10): 879-884; and Burks et al. (1997) *Proc. Natl. Acad. Sci. USA* 94: 412-417).

The term "non-conservative amino acid substitution" refers to the substitution of an amino acid in one class with an amino acid from another class; for example, substitution of an Ala, a class II residue, with a class III residue such as Asp, Asn, Glu, or Gln.

In another embodiment, mutations (conservative or non-conservative) can be introduced randomly along all or part of an anti-ALPP/ALPPL2 antibody coding sequence, such as by saturation mutagenesis, and the resulting modified antibodies can be screened for binding activity.

A "consensus sequence" is a sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" of an immunoglobulin refers to a framework region in the consensus immunoglobulin sequence.

Similarly, the consensus sequence for the CDRs of can be derived by optimal alignment of the CDR amino acid sequences of the anti-ALPP/ALPPL2 antibodies described herein.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions.times.100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software, using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of Meyers and Miller (1989) *CABIOS,* 4: 11-17, which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (1970) *J. Mol. Biol.* 48: 444-453 algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the contemplated herein can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

The nucleic acid compositions described herein (e.g., nucleic acids encoding all or a portion of an anti-ALPP/ALPPL2 antibody or immunoconjugate) while often in a native sequence (except for modified restriction sites and the like), from either cDNA, genomic or mixtures thereof may be mutated, in accordance with standard techniques to provide variant sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

The term "operably linked" refers to a nucleic acid sequence placed into a functional relationship with another nucleic acid sequence. For example, DNA for a pre-sequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms, "plasmid" and "vector" may be used interchangeably. However, the invention is intended to include such other forms of expression vectors, such as viral vectors (e.g., replication defective retroviruses, adenoviruses and adeno-associated viruses), that serve equivalent functions.

The term "recombinant host cell" (or simply "host cell"), as used herein, is intended to refer to a cell into which an expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The terms "treat," "treating," and "treatment," as used herein, refer to therapeutic or preventative measures described herein. The methods of "treatment" employ administration to a subject (e.g., a subject in need thereof), an anti-ALPP/ALPPL2 antibody or antigen binding portion or an immunoconjugate comprising such an antibody or antigen binding portion described herein. In certain embodiments the subject is a subject diagnosed with and/or under treatment for an ALPPL2 positive cancer (e.g., mesothelioma) in order to prevent, cure, delay, reduce the severity of, or ameliorate one or more symptoms of the disease or disorder or recurring disease or disorder, or in order to prolong the survival of a subject beyond that expected in the absence of such treatment.

The terms "cancer" and "cancerous" refer to or describe the physiological condition in mammals that is typically characterized by unregulated cell growth. An ALPP- or ALPPL2-positive positive cancer refers to a cancer characterized by cells that express or overexpress ALPP and/or ALPPL2 or a fragment thereof bound by the M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF antibodies described herein. Illustrative ALPPL2-positive cancers include, but are not limited to, mesothelioma, testicular cancer, endometrial cancer, and a subset of pancreatic cancer, ovarian cancer and non-small cell lung cancer.

The term "effective amount," as used herein, refers to that amount of an anti-ALPP/ALPPL2 antibody or an antigen binding portion thereof and/or an immunoconjugate thereof, that is sufficient to effect treatment, prognosis or diagnosis of a disease associated with the growth and/or proliferation of ALPP/ALPPL2-positive cells (e.g., an ALPP/ALPPL2-positive cancer), as described herein, when administered to a subject. A therapeutically effective amount will vary depending upon the subject and disease condition being treated, the weight and age of the subject, the severity of the disease condition, the manner of administration and the like, which can readily be determined by one of ordinary skill in the art. The dosages for administration can range from, for example, about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, of an anti-ALPP/ALPPL2 antibody described herein and/or antigen binding portion thereof, and/or immunoconjugate thereof as described herein. Dosage regiments may be adjusted to provide the optimum therapeutic response. An effective amount is also one in which any toxic or detrimental effects (i.e., side effects) of an antibody or antigen binding portion thereof are minimized and/or outweighed by the beneficial effects.

An "effector" refers to any molecule or combination of molecules whose activity it is desired to deliver/into and/or localize at cell. Effectors include, but are not limited to labels, cytotoxins, enzymes, growth factors, transcription factors, antibodies, drugs, etc.

The phrase "inhibiting the growth and/or proliferation", e.g. of cancer cells includes inter alia inducing cellular apoptosis or other cell killing mechanisms, reducing the invasiveness of the cells, stalling the cells at a point in the cell cycle, and the like.

The term "immunoconjugate" refers to an antibody attached to one or more effectors or to a plurality of antibodies attached to one or more effectors. The term "immunoconjugate" is intended to include effectors chemically conjugated to the antibodies as well as antibodies expresses as a fusion protein where the antibody (or a portion thereof) is directly attached or attached through a linker to a peptide effector or to an effector comprising a peptide.

The term "anti-tumor effect" as used herein, refers to a biological effect that can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the antibodies, immunoconjugates, CAR-cells described herein in prevention of the occurrence of tumor in the first place.

The term "autologous" is meant to refer to any material derived from the same individual to which it is later to be re-introduced into the individual.

The term "allogeneic" refers to a cell or graft derived from a different animal of the same species.

The term "xenogeneic" refers to a cell or graft derived from an animal of a different species.

The term "co-stimulatory ligand," as the term is used herein, includes a molecule on an antigen presenting cell (e.g., an APC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-IBB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, that in combination with a primary signal, such as TCR/CD3 ligation, leads to T cell proliferation and/or upregulation or downregulation of key molecules.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an APC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

BRIEF DESCRIPTION OF THE DRAWINGS

FIG. 1 illustrates the amino acid sequences for ALPP (SEQ ID NO:1) and ALPPL2 (SEQ ID NO:2).

FIG. 3A shows geometric means of tumor volumes were plotted. Injection started on day-7, every 5-day, for 5 doses of 5 mg/kg per mouse. M25mcvcpabMMAF: the test ADC (MMAF conjugated to M25 IgG1). IgG: naked M25 IgG1 control. FIG. 3B: Animal body weights were monitored and plotted. No overt sign of toxicity was seen. Note: in the experiment shown in A and B, a control ADC (ctr IgG1-mcvcpab-MMAF) was not included, but we have studied the control ADC in other experiments: it behaves similarly to that of the vehicle or naked IgG control).

DETAILED DESCRIPTION

Figure 2:
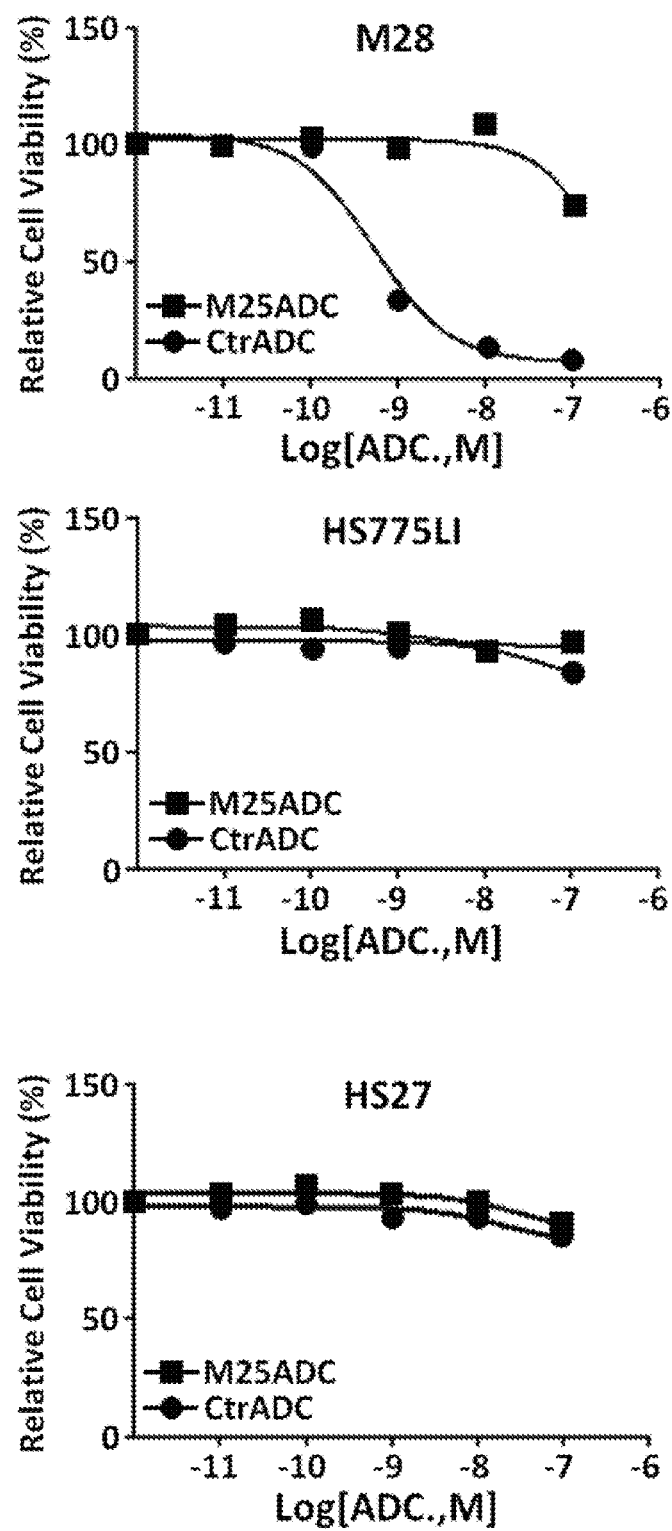
FIG. 2 illustrates potent and specific tumor cell killing in vitro. MMAF was conjugated to the M25 IgG1 via the mc-vc-pab linker, purified, and incubated with mesothelioma cell line M28 and control cells (HS775Li, a primary human liver cell line, and HS27, a foreskin fibroblast cell line). There are over 1,000-fold differential in EC50s between tumor and control non-tumorigenic cells (0.54 nM vs.>1 µM), demonstrating potent and selective tumor killing by our novel ADC.

In various embodiments antibodies are provided that bind to cell surface antigens that are overexpressed by tumor cells with no or minimal expression on normal human tissues. The antibodies can be used alone in the treatment of cancers, or in various embodiments uses of the antibodies include, but are not limited to:

1) Use for payload delivery (e.g., drug, siRNA, mRNA, cytokine, radionuclide) to a tumor cell;

2) Use as components of a bispecific or oligospecific antibody that selectively activates the immune system at the site of the tumor;

3) Use in the construction of chimeric antigen receptors (CAR-T) for cell based therapies;

4) Use in the construction of bispecific antibodies; and

5) Use as diagnostic/staging tools for tumor detection/quanfi9ication and for patient stratification and outcome analysis.

Through phage antibody display library selection on live tumor cells and cancer specimens, we have identified a novel anti-ALPPL2 antibody. ALPPL2 is expressed specifically by several types of incurable cancer but not normal human tissues except for placental trophoblasts. The exquisite tissue specificity of ALPPL2 should facilitate the preparation of highly specific targeted therapy and immunotherapy against cancers that overexpress this antigen. Such cancers include, but are not limited to mesothelioma, testicular cancer, endometrial cancer, and a subset of pancreatic cancer, ovarian cancer and non-small cell lung cancer. As illustrated in the Examples herein, the targetability of the antigen has been demonstrated in vitro and in vivo with antibody-drug conjugates (ADCs) using auristatin derivatives.

Accordingly in various embodiments, isolated anti-ALPP/ALPPL2 are provided as well as chimeric moieties comprising the anti-ALPP/ALPPL2 antibodies joined to an effector. In certain embodiments antibody-drug conjugates (ADCs) are provided that comprise an anti-ALPP/ALPPL2 antibody attached to a cytotoxic/cytostatic drug, for example a drug that has activity against both dividing and resting tumor cells, such as DNA chelating agents.

Additionally chimeric constructs are provided that expand beyond targeted chemotherapy to immunotherapy by incorporating, for example, providing bispecific antibodies comprising an anti-ALPP/ALPPL2 antibody attached to a second antibody that is capable of recruiting and activating immune system components or attached to a moiety that is a checkpoint inhibitor (e.g., anti-CTLA4 (e.g., comprising an ipilimumab variable region), and/or antibodies directed against PD-L1 (e.g., comprising an nivolumab, or pembrolizumab variable region), and/or antibodies directed against PD-L2. In certain embodiments the anti-ALPP/ALPPL2 antibodies are used in other platforms including, but not limited to, platforms such as chimeric antigen receptor engineered T cells (CAR-T) and immunocytokines.

Antibodies that Bind ALPP/ALPPL2

Antibodies were discovered that specifically bind ALPP and/or ALPPL2 in vitro and in situ, e.g., when a cancer cell expressing ALPPL2 is in a tissue microenvironment. As indicated above, such antibodies are useful for targeting cancers when used alone, or when attached to an effector to form a "targeted effector".

Accordingly in certain embodiments, an isolated antibody is provided that that specifically binds ALPP and/or ALPPL2 and that specifically binds to a cell that expresses or overexpresses ALPPL/ALPPL2 (e.g., a mesothelioma cell, a testicular cancer cell, an endometrial cancer cell, and certain pancreatic cancer, ovarian cancer and non-small cell lung cancer cells).

The antibodies designated herein as M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF (see, e.g., Table 1) are illustrative prototypical antibodies. In certain embodiments antibodies that comprise VL CDR1 and/or VL CDR2, and/or VL CDR3, and/or VH CDR1 and/or VH CDR2, and/or VH CDR3 of one or more of these antibodies are contemplated. In certain embodiments antibodies that comprise the VH domain and/or the VL domain of one or more of these antibodies are contemplated. Also contemplated are antibodies that compete for binding at ALPPL and/or ALPPL2, particularly when expressed and displayed at the cell surface, with one or more of as M25AD, MD25ADX and/or M25.

The amino acid sequences of the VH and VL domains of M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and M25wtLF antibodies are shown in Table 1.

TABLE 1

Amino acid sequences of VH and VL domains of novel human anti-ALPP/ALPPL2 antibodies. Underlined regions represent CDR1, CDR2, and CDR3, respectively. M25 and ALPPL2rd3_1 have identical heavy chain but different light chains. M25AD and ALPPrd3_2 have identical heavy chain but different light chains. SEQ ID NOs are given for VH joined to VL by indicated linker (i.e., VH-Linker-VL).

| Name | VH | Linker | VL | SEQ ID NO |
|---|---|---|---|---|
| M25ADLF | QVQLQQSGGGLVKPGGSRLSCAASGFTFSSYDMHWVRQAPGKGLEWVAVISYDGSNKYYADSVKGRFTISRDNSKNTLYLQMDSLRAEDTAVYFCAKEGDSSRWSYDLWGRGTLVTVSS | GGGGS GGGGS GGGGS | QSALTQPASVSGSPGQSITISCTGTSSDVGGYNYVSWYQQHPGKAPKVMIYDVTNRPSGVSNRFSGSKSGNTASLTISGLQAEDEADYYCSSYTSTSTFVVFGGGTKLTVLG | 3 |
| M25ADLFEG | QVQLQQSGGGLVKPGGSRLSCAASGFTFSSYDMHWVRQAPGKGLEWVAVISYEGSNKYYADSVKGRFTISRDNSKNTLYLQMDSLRAEDTAVYFCAKEGDSSRWSYDLWGRGTLVTVSS | GGGGS GGGGS GGGGS | QSALTQPASVSGSPGQSITISCTGTSSDVGGYNYVSWYQQHPGKAPKVMIYDVTNRPSGVSNRFSGSKSGNTASLTISGLQAEDEADYYCSSYTSTSTFVVFGGGTKLTVLG | 4 |
| M25ADLFDS | QVQLQQSGGGLVKPGGSRLSCAASGFTFSSYDMHWVRQAPGKGLEWVAVISYDSSNKYYADSVKGRFTISRDNSKNTLYLQMDSLRAEDTAVYFCAKEGDSSRWSYDLWGRGTLVTVSS | GGGGS GGGGS GGGGS | QSALTQPASVSGSPGQSITISCTGTSSDVGGYNYVSWYQQHPGKAPKVMIYDVTNRPSGVSNRFSGSKSGNTASLTISGLQAEDEADYYCSSYTSTSTFVVFGGGTKLTVLG | 5 |
| M25FYIA | QVQLQQSGGGLVKPGGSRLSCAASGFTFSSYAMHWVRQAPGKGLEWVAVISYDGSNKYYADSVKGRFTISRDNSKNTLYLQMDSLRAEDTAVYYCAKEGDSSRWSYDLWGRGTLVTVSS | GGGGS GGGGS GGGGS | QSALTQPASVSGSPGQSITISCTGTSSDVGGYNYVSWYQQHPGKAPKVMIYDVTNRPSGVSNRFSGSKSGNTASLTISGLQAEDEADYYCSSYTIASTLVVFGGGTKLTVL | 6 |
| M25FYIAEG | QVQLQQSGGGLVKPGGSRLSCAASGFTFSSYAMHWVRQAPGKGLEWVAVISYEGSNKYYADSVKGRFTISRDNSKNTLYLQMDSLRAEDTAVYYCAKEGDSSRWSYDLWGRGTLVTVSS | GGGGS GGGGS GGGGS | QSALTQPASVSGSPGQSITISCTGTSSDVGGYNYVSWYQQHPGKAPKVMIYDVTNRPSGVSNRFSGSKSGNTASLTISGLQAEDEADYYCSSYTIASTLVVFGGGTKLTVL | 7 |
| M25FYIADS | QVQLQQSGGGLVKPGGSRLSCAASGFTFSSYAMHWVRQAPGKGLEWVAVISYDSSNKYYADSVKGRFTISRDNSKNTLYLQMDSLRAEDTAVYYCAKEGDSSRWSYDLWGRGTLVTVSS | GGGGS GGGGS GGGGS | QSALTQPASVSGSPGQSITISCTGTSSDVGGYNYVSWYQQHPGKAPKVMIYDVTNRPSGVSNRFSGSKSGNTASLTISGLQAEDEADYYCSSYTIASTLVVFGGGTKLTVL | 8 |
| M25 | QVQLQQSGGGLVKPGGSRLSCAASGFTFSSYAMHWVRQAPGKGLEWVAVISYDGSNKYYADSVKGRFTISRDNSKNTLYLQMDSLRAEDTAVYFCAKEGDSSRWSYDLWGRGTLVTVSS | GGGGS GGGGS GGGGS | QSALTQPASVSGSPGQSITISCTGTSSDVGGYNYVSWYQQHPGKAPKVMIYDVTNRPSGVSNRFSGSKSGNTASLTISGLQAEDEADYYCSSYTSTSTLVVFGGGTKLTVL | 9 |
| M25EG | QVQLQQSGGGLVKPGGSRLSCAASGFTFSSYAMHWVRQAPGKGLEWVAVISYEGSNKYYADSVKGRFTISRDNSKNTLYLQMDSLRAEDTAVYFCAKEGDSSRWSYDLWGRGTLVTVSS | GGGGS GGGGS GGGGS | QSALTQPASVSGSPGQSITISCTGTSSDVGGYNYVSWYQQHPGKAPKVMIYDVTNRPSGVSNRFSGSKSGNTASLTISGLQAEDEADYYCSSYTSTSTLVVFGGGTKLTVL | 10 |
| M25DS | QVQLQQSGGGLVKPGGSRLSCAASGFTFSSYAMHWVRQAPGKGLEWVAVISYDSSNKYYADSVKGRFTISRDNSKNTLYLQMDSLRAEDTAVYFCAKEGDSSRWSYDLWGRGTLVTVSS | GGGGS GGGGS GGGGS | QSALTQPASVSGSPGQSITISCTGTSSDVGGYNYVSWYQQHPGKAPKVMIYDVTNRPSGVSNRFSGSKSGNTASLTISGLQAEDEADYYCSSYTSTSTLVVFGGGTKLTVL | 11 |
| M25AELF | QVQLQQSGGGLVKPGGSRLSCAASGFTFSSYEMHWVRQAPGKGLEWVAVISYDGSNKYYADSVKGRFTISRDNSKNTLYLQMDSLRAEDTAVYFCAKEGDSSRWSYDLWGRGTLVTVSS | GGGGS GGGGS GGGGS | QSALTQPASVSGSPGQSITISCTGTSSDVGGYNYVSWYQQHPGKAPKVMIYDVTNRPSGVSNRFSGSKSGNTASLTISGLQAEDEADYYCSSYTSTSTFVVFGGGTKLTVLG | 12 |

TABLE 1-continued

Amino acid sequences of VH and VL domains of novel human anti-ALPP/ALPPL2 antibodies. Underlined regions represent CDR1, CDR2, and CDR3, respectively. M25 and ALPPL2rd3_1 have identical heavy chain but different light chains. M25AD and ALPPrd3_2 have identical heavy chain but different light chains. SEQ ID NOs are given for VH joined to VL by indicated linker (i.e., VH-Linker-VL).

| Name | VH | Linker | VL | SEQ ID NO |
|---|---|---|---|---|
| M25AELFEG | QVQLQQSGGGLVKPGGSLRL SCAASGFTFSSYEMHWVRQA PGKGLEWVAVISYEGSNKYY ADSVKGRFTISRDNSKNTLY LQMDSLRAEDTAVYFCAKEG DSSRWSYDLWGRGTLVTVSS | GGGGS GGGGS GGGGS | QSALTQPASVSGSPGQSITI SCTGTSSDVGGYNYVSWYQQ HPGKAPKVMIYDVTNRPSGV SNRFSGSKSGNTASLTISGL QAEDEADYYCSSYTSTSTFV VFGGGTKLTVLG | 13 |
| M25AELFDS | QVQLQQSGGGLVKPGGSLRL SCAASGFTFSSYEMHWVRQA PGKGLEWVAVISYDSSNKYY ADSVKGRFTISRDNSKNTLY LQMDSLRAEDTAVYFCAKEG DSSRWSYDLWGRGTLVTVSS | GGGGS GGGGS GGGGS | QSALTQPASVSGSPGQSITI SCTGTSSDVGGYNYVSWYQQ HPGKAPKVMIYDVTNRPSGV SNRFSGSKSGNTASLTISGL QAEDEADYYCSSYTSTSTFV VFGGGTKLTVLG | 14 |
| M25ADL99P | QVQLQQSGGGLVKPGGSLRL SCAASGFTFSSYDMHWVRQA PGKGLEWVAVISYDGSNKYY ADSVKGRFTISRDNSKNTLY LQMDSLRAEDTAVYFCAKEG DSSRWSYDLWGRGTLVTVSS | GGGGS GGGGS GGGGS | QSALTQPASVSGSPGQSITI SCTGTSSDVGGYNYVSWYQQ HPGKAPKVMIYDVTNRPSGV SNRFSGSKSGNTASLTISGL QAEDEADYYCSSYTSTSTPV VFGGGTKLTVL | 15 |
| M25ADL99G | QVQLQQSGGGLVKPGGSLRL SCAASGFTFSSYDMHWVRQA PGKGLEWVAVISYDGSNKYY ADSVKGRFTISRDNSKNTLY LQMDSLRAEDTAVYFCAKEG DSSRWSYDLWGRGTLVTVSS | GGGGS GGGGS GGGGS | QSALTQPASVSGSPGQSITI SCTGTSSDVGGYNYVSWYQQ HPGKAPKVMIYDVTNRPSGV SNRFSGSKSGNTASLTISGL QAEDEADYYCSSYTSTSTGV VFGGGTKLTVL | 16 |
| M25ADS95R | QVQLQQSGGGLVKPGGSLRL SCAASGFTFSSYDMHWVRQA PGKGLEWVAVISYDGSNKYY ADSVKGRFTISRDNSKNTLY LQMDSLRAEDTAVYFCAKEG DSSRWSYDLWGRGTLVTVSS | GGGGS GGGGS GGGGS | QSALTQPASVSGSPGQSITI SCTGTSSDVGGYNYVSWYQQ HPGKAPKVMIYDVTNRPSGV SNRFSGSKSGNTASLTISGL QAEDEADYYCSSYTRTSTLV VFGGGTKLTVL | 17 |
| M25ADD28G | QVQLQQSGGGLVKPGGSLRL SCAASGFTFSSYDMHWVRQA PGKGLEWVAVISYDGSNKYY ADSVKGRFTISRDNSKNTLY LQMDSLRAEDTAVYFCAKEG DSSRWSYDLWGRGTLVTVSS | GGGGS GGGGS GGGGS | QSALTQPASVSGSPGQSITI SCTGTSSGVGGYNYVSWYQQ HPGKAPKVMIYDVTNRPSGV SNRFSGSKSGNTASLTISGL QAEDEADYYCSSYTSTSTLV VFGGGTKLTVL | 18 |
| M25ADS91G | QVQLQQSGGGLVKPGGSLRL SCAASGFTFSSYDMHWVRQA PGKGLEWVAVISYDGSNKYY ADSVKGRFTISRDNSKNTLY LQMDSLRAEDTAVYFCAKEG DSSRWSYDLWGRGTLVTVSS | GGGGS GGGGS GGGGS | QSALTQPASVSGSPGQSITI SCTGTSSDVGGYNYVSWYQQ HPGKAPKVMIYDVTNRPSGV SNRFSGSKSGNTASLTISGL QAEDEADYYCGSYTSTSTLV VFGGGTKLTVL | 19 |
| M25ADY93H | QVQLQQSGGGLVKPGGSLRL SCAASGFTFSSYDMHWVRQA PGKGLEWVAVISYDGSNKYY ADSVKGRFTISRDNSKNTLY LQMDSLRAEDTAVYFCAKEG DSSRWSYDLWGRGTLVTVSS | GGGGS GGGGS GGGGS | QSALTQPASVSGSPGQSITI SCTGTSSDVGGYNYVSWYQQ HPGKAPKVMIYDVTNRPSGV SNRFSGSKSGNTASLTISGL QAEDEADYYCSSHTSTSTLV VFGGGTKLTVL | 20 |
| M25ADYHSRLF | QVQLQQSGGGLVKPGGSLRL SCAASGFTFSSYDMHWVRQA PGKGLEWVAVISYDGSNKYY ADSVKGRFTISRDNSKNTLY LQMDSLRAEDTAVYFCAKEG DSSRWSYDLWGRGTLVTVSS | GGGGS GGGGS | SALTQPASVSGSPGQSITIS CTGTSSDVGGYNYVSWYQQH PGKAPKVMIYDVTNRPSGVS NRFSGSKSGNTASLTISGLQ AEDEADYYCSSHTRTSTFVV FGGGTKLTVLG | 21 |

TABLE 1-continued

Amino acid sequences of VH and VL domains of novel human anti-ALPP/ALPPL2 antibodies. Underlined regions represent CDR1, CDR2, and CDR3, respectively. M25 and ALPPL2rd3_1 have identical heavy chain but different light chains. M25AD and ALPPrd3_2 have identical heavy chain but different light chains. SEQ ID NOs are given for VH joined to VL by indicated linker (i.e., VH-Linker-VL).

| Name | VH | Linker | VL | SEQ ID NO |
|---|---|---|---|---|
| M25GRITSGFYGDwtLC | QVQLQQSGGGLVKPGGSRLSCAASRFTFSSYAMHWVRQAPGKGLEWVAVISYDGSNKYYADSVKGRFTTSRDNSKNTLYLQMDGLRAEDTAVYYCAKEDDSSRWSYDLWGRGTLVTVSS | GGGGS GGGGS GGGGS | QSALTQPASVSGSPGQSITISCTGTSSDVGGYNYVSWYQQHPGKAPKVMIYDVTNRPSGVSNRFSGSKSGNTASLTISGLQAEDEADYYCSSYTSTSTLVVFGGGTKLTVL | 22 |
| M25FSITSGFYGDwtLC | QVQLQQSGGGLVKPGGSRLSCAASGSTFSSYAMHWVRQAPGKGLEWVAVISYDGSNKYYADSVKGRFTTSRDNSKNTLYLQMDGLRAEDTAVYYCAKEDDSSRWSYDLWGRGTLVTVSS | GGGGS GGGGS GGGGS | QSALTQPASVSGSPGQSITISCTGTSSDVGGYNYVSWYQQHPGKAPKVMIYDVTNRPSGVSNRFSGSKSGNTASLTISGLQAEDEADYYCSSYTSTSTLVVFGGGTKLTVL | 23 |
| M253018IA | QVQLVESGGGVVQPGRSLRLSCAASGFTFSSYDMHWVRQAPGKGLEWVAVISYDGSNKYYADSVKGRFTISRDNSKNTLYLQMNSLRAEDTAVYYCAREGDSSRWSYDLWGRGTLVTVSS | GGGGS GGGGS GGGGS | QSALTQPASVSGSPGQSITISCTGTSSDVGGYNYVSWYQQHPGKAPKVMIYDVTNRPSGVSNRFSGSKSGNTASLTISGLQAEDEADYYCSSYTIASTLVVFGGGTKLTVL | 24 |
| M253018LF | QVQLVESGGGVVQPGRSLRLSCAASGFTFSSYDMHWVRQAPGKGLEWVAVISYDGSNKYYADSVKGRFTISRDNSKNTLYLQMNSLRAEDTAVYYCAREGDSSRWSYDLWGRGTLVTVSS | GGGGS GGGGS GGGGS | QSALTQPASVSGSPGQSITISCTGTSSDVGGYNYVSWYQQHPGKAPKVMIYDVTNRPSGVSNRFSGSKSGNTASLTISGLQAEDEADYYCSSYTSTSTFVVFGGGTKLTVLG | 25 |
| M25AD | QVQLQQSGGGLVKPGGSRLSCAASGFTFSSYDMHWVRQAPGKGLEWVAVISYDGSNKYYADSVKGRFTISRDNSKNTLYLQMDSLRAEDTAVYFCAKEGDSSRWSYDLWGRGTLVTVSS | GGGGS GGGGS GGGGS | QSALTQPASVSGSPGQSITISCTGTSSDVGGYNYVSWYQQHPGKAPKVMIYDVTNRPSGVSNRFSGSKSGNTASLTISGLQAEDEADYYCSSYTSTSTLVVFGGGTKLTVL | 26 |
| M25ADX | QVQLQQSGGGLVKPGGSRLSCAASGFTFSSYDMHWVRQAPGKGLEWVAVISYDGSNKYYADSVKGRFTISRDNSRNTLSLQMSSLRAEDTALYYCVKEGDSSRWSYDPWGRGTLVTVSS | GGGGS GGGGS GGGGS | QSALTQPASVSGSPGQSITISCTGTSSDVGGYNYVSWYQQHPGKAPKVMIYDVTNRPSGVSNRFSGSKSGNTASLTISGLQAEDEADYYCSSYTSTSTLVVFGGGTKLTVLG | 27 |
| ALPPL2rd3_1 | QVQLQQSGGGLVKPGGSRLSCAASGFTFSSYAMHWVRQAPGKGLEWVAVISYDGSNKYYADSVKGRFTISRDNSKNTLYLQMDSLRAEDTAVYFCAKEGDSSRWSYDLWGRGTLVTVSS | GGGGS GGGGS GGGGS | QSALTQPASVSGSPGQSITISCTGTSSDVGGYKYVSWYQQHPGKAPKLMIYEVSNRPSGVSNRFSGSKSGNTASLTISGLQAEDEAAYFCSAYSPPGIMMFGGGTKLTVLG | 28 |
| ALPPL2rd3_2 | QVQLQQSGGGLVKPGGSRLSCAASGFTFSSYDMHWVRQAPGKGLEWVAVISYDGSNKYYADSVKGRFTISRDNSKNTLYLQMDSLRAEDTAVYFCAKEGDSSRWSYDLWGRGTLVTVSS | GGGGS GGGGS GGGGS | QSALTQPASVSGSPGQSITISCTGTSSDVGGYKYVSWYQQHPGKAPKLMIYEVSNRPSGVSNRFSGSKSGNTASLTISGLQAEDEAAYFCSAYSPPGIMMFGGGTKLTVLG | 29 |
| M25AGIA | QVQLQQSGGGLVKPGGSRLSCAASGFTFSSYGMHWVRQAPGKGLEWVAVISYDGSNKYYADSVKGRFTISRDNSKNTLYLQMDSLRAEDTAVYFCAKEGDSSRWSYDLWGRGTLVTVSS | GGGGS GGGGS GGGGS | QSALTQPASVSGSPGQSITISCTGTSSDVGGYNYVSWYQQHPGKAPKVMIYDVTNRPSGVSNRFSGSKSGNTASLTISGLQAEDEADYYCSSYTIASTLVVFGGGTKLTVL | 30 |
| M25AGLF | QVQLQQSGGGLVKPGGSRLSCAASGFTFSSYGMHWVRQAPGKGLEWVAVISYDGSNKYYADSVKGRFTISRDNSKNTLYLQMDSLRAEDTAVYFCAKEGDSSRWSYDLWGRGTLVTVSS | GGGGS GGGGS GGGGS | QSALTQPASVSGSPGQSITISCTGTSSDVGGYNYVSWYQQHPGKAPKVMIYDVTNRPSGVSNRFSGSKSGNTASLTISGLQAEDEADYYCSSYTSTSTFVVFGGGTKLTVLG | 31 |

TABLE 1-continued

Amino acid sequences of VH and VL domains of novel human anti-ALPP/ALPPL2 antibodies. Underlined regions represent CDR1, CDR2, and CDR3, respectively. M25 and ALPPL2rd3_1 have identical heavy chain but different light chains. M25AD and ALPPrd3_2 have identical heavy chain but different light chains. SEQ ID NOs are given for VH joined to VL by indicated linker (i.e., VH-Linker-VL).

| Name | VH | Linker | VL | SEQ ID NO |
|---|---|---|---|---|
| M25ASIA | QVQLQQSGGGLVKPGGSLRL SCAASGFTFSSYSMHWVRQA PGKGLEWVAVISYDGSNKYY ADSVKGRFTISRDNSKNTLY LQMDSLRAEDTAVYFCAKEG DSSRWSYDLWGRGTLVTVSS | GGGGS GGGGS GGGGS | QSALTQPASVSGSPGQSITI SCTGTSSDVGGYNYVSWYQQ HPGKAPKVMIYDVTNRPSGV SNRFSGSKSGNTASLTISGL QAEDEADYYCSSYTIASTLV VFGGGTKLTVL | 32 |
| M25ASLF | QVQLQQSGGGLVKPGGSLRL SCAASGFTFSSYSMHWVRQA PGKGLEWVAVISYDGSNKYY ADSVKGRFTISRDNSKNTLY LQMDSLRAEDTAVYFCAKEG DSSRWSYDLWGRGTLVTVSS | GGGGS GGGGS GGGGS | QSALTQPASVSGSPGQSITI SCTGTSSDVGGYNYVSWYQQ HPGKAPKVMIYDVTNRPSGV SNRFSGSKSGNTASLTISGL QAEDEADYYCSSYTSTSTFV VFGGGTKLTVLG | 33 |
| M25ASwt | QVQLQQSGGGLVKPGGSLRL SCAASGFTFSSYSMHWVRQA PGKGLEWVAVISYDGSNKYY ADSVKGRFTISRDNSKNTLY LQMDSLRAEDTAVYFCAKEG DSSRWSYDLWGRGTLVTVSS | GGGGS GGGGS GGGGS | QSALTQPASVSGSPGQSITI SCTGTSSDVGGYNYVSWYQQ HPGKAPKVMIYDVTNRPSGV SNRFSGSKSGNTASLTISGL QAEDEADYYCSSYTSTSTLV VFGGGTKLTVL | 34 |
| M25AVIA | QVQLQQSGGGLVKPGGSLRL SCAASGFTFSSYVMHWVRQA PGKGLEWVAVISYDGSNKYY ADSVKGRFTISRDNSKNTLY LQMDSLRAEDTAVYFCAKEG DSSRWSYDLWGRGTLVTVSS | GGGGS GGGGS GGGGS | QSALTQPASVSGSPGQSITI SCTGTSSDVGGYNYVSWYQQ HPGKAPKVMIYDVTNRPSGV SNRFSGSKSGNTASLTISGL QAEDEADYYCSSYTIASTLV VFGGGTKLTVL | 35 |
| M25AVLF | QVQLQQSGGGLVKPGGSLRL SCAASGFTFSSYVMHWVRQA PGKGLEWVAVISYDGSNKYY ADSVKGRFTISRDNSKNTLY LQMDSLRAEDTAVYFCAKEG DSSRWSYDLWGRGTLVTVSS | GGGGS GGGGS GGGGS | QSALTQPASVSGSPGQSITI SCTGTSSDVGGYNYVSWYQQ HPGKAPKVMIYDVTNRPSGV SNRFSGSKSGNTASLTISGL QAEDEADYYCSSYTSTSTFV VFGGGTKLTVLG | 36 |
| M25ALIA | QVQLQQSGGGLVKPGGSLRL SCAASGFTFSSYLMHWVRQA PGKGLEWVAVISYDGSNKYY ADSVKGRFTISRDNSKNTLY LQMDSLRAEDTAVYFCAKEG DSSRWSYDLWGRGTLVTVSS | GGGGS GGGGS GGGGS | QSALTQPASVSGSPGQSITI SCTGTSSDVGGYNYVSWYQQ HPGKAPKVMIYDVTNRPSGV SNRFSGSKSGNTASLTISGL QAEDEADYYCSSYTIASTLV VFGGGTKLTVL | 37 |
| M25ALLF | QVQLQQSGGGLVKPGGSLRL SCAASGFTFSSYLMHWVRQA PGKGLEWVAVISYDGSNKYY ADSVKGRFTISRDNSKNTLY LQMDSLRAEDTAVYFCAKEG DSSRWSYDLWGRGTLVTVSS | GGGGS GGGGS GGGGS | QSALTQPASVSGSPGQSITI SCTGTSSDVGGYNYVSWYQQ HPGKAPKVMIYDVTNRPSGV SNRFSGSKSGNTASLTISGL QAEDEADYYCSSYTSTSTFV VFGGGTKLTVLG | 38 |
| M25wt IA | QVQLQQSGGGLVKPGGSLRL SCAASGFTFSSYAMHWVRQA PGKGLEWVAVISYDGSNKYY ADSVKGRFTISRDNSKNTLY LQMDSLRAEDTAVYFCAKEG DSSRWSYDLWGRGTLVTVSS | GGGGS GGGGS GGGGS | QSALTQPASVSGSPGQSITI SCTGTSSDVGGYNYVSWYQQ HPGKAPKVMIYDVTNRPSGV SNRFSGSKSGNTASLTISGL QAEDEADYYCSSYTIASTLV VFGGGTKLTVL | 39 |
| M25wt LF | QVQLQQSGGGLVKPGGSLRL SCAASGFTFSSYAMHWVRQA PGKGLEWVAVISYDGSNKYY ADSVKGRFTISRDNSKNTLY LQMDSLRAEDTAVYFCAKEG DSSRWSYDLWGRGTLVTVSS | GGGGS GGGGS GGGGS | QSALTQPASVSGSPGQSITI SCTGTSSDVGGYNYVSWYQQ HPGKAPKVMIYDVTNRPSGV SNRFSGSKSGNTASLTISGL QAEDEADYYCSSYTSTSTFV VFGGGTKLTVLG | 40 |

Using the amino acid sequences provided for the M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and M25wtLF antibodies, numerous antibody forms can be prepared, e.g., as described below. Such forms include, but are not limited to a substantially intact (e.g., full length) immunoglobulin (e.g., an IgA, IgE, IgG, and the like), an antibody fragment (e.g., Fv, Fab, (Fab')$_2$, (Fab')$_3$, IgGΔCH$_2$, a minibody, and the like), a single chain antibody (e.g., scFv), a diabody, a unibody, an affibody, and the like.

It will be recognized, that in certain embodiments, e.g., where the antibodies are single chain antibodies, the VH and VL domains comprising such antibody can be joined directly together or by a peptide linker. Illustrative peptide linkers include, but are not limited to GGGGS GGGGS GGGGS (SEQ ID NO:41), GGGGS GGGGS (SEQ ID NO:42), GGGGS (SEQ ID NO:43), GS GGGGS GGGGS GGS GGGGS (SEQ ID NO:44), SGGGGS (SEQ ID NO:45), GGGS (SEQ ID NO:46), VPGV (SEQ ID NO:47), VPGVG (SEQ ID NO:48), GVPGVG (SEQ ID NO:49), GVG VP GVG (SEQ ID NO:50), VP GVG VP GVG (SEQ ID NO:51), GGSSRSS (SEQ ID NO:52), and GGSSRSSSSGGGGSGGGG (SEQ ID NO:53), and the like.

As indicated above, in various embodiments, the antibody binds (e.g., specifically binds ALPP and/or ALPPL2 (see, e.g., FIG. 1 for ALPP and ALPPL2 sequences). Typically antibodies contemplated herein will specifically bind cancer cells that express ALPPL2 or a domain thereof that is bound by the M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF antibodies described herein. In certain embodiments the antibody binds to cell expressing ALPPL2 with an affinity greater than (K$_D$ less than) about 5 nM, or less than about 4 nM, or less than about 3 nM, or about 2 nM or less when measured on live cells by FACS. In certain embodiments the antibody binds to cell expressing ALPPL2 with an affinity greater than (K$_D$ less than) about 50 pM, or less than about 40 pM, or less than about 30 pM when measured on live cells by FACS.

Using the sequence information provided herein antibodies comprising one or more of the CDRs comprising, e.g., M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF, or antibodies comprising the VH and/or VL domain(s) of these antibodies can readily be prepared using standard methods (e.g. chemical synthesis methods and/or recombinant expression methods) well known to those of skill in the art, e.g., as described below.

In addition, other "related" anti-ALPP/ALPPL2 antibodies can be identified by screening for antibodies that bind to the same epitope (e.g. that compete with one or more of M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF antibodies for binding to ALPP and/or ALPPL2 and/or to a cell expressing or overexpressing ALPP and/or ALPPL2, and/or by modification of the M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF antibodies identified herein to produce libraries of modified antibody and then rescreening antibodies in the library for improved binding to cells expressing or overexpressing ALPP and/or ALPPL2 or a domain thereof.

Identification of Other Antibodies Binding the Same ALPP and/or ALPPL2 Epitope(s) as M25AD, MD25ADX and/or M25.

Having identified ALPP and/or ALPP2 as useful antibody target(s) and M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF antibodies as useful prototypical antibodies, other "related" antibodies that bind ALPP and/or ALPPL2 can readily be identified by screening for antibodies that bind ALPP/ALPPL2 and that cross-react with one or more of M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF, e.g., at the epitope bound by M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF, and/or for antibodies that cross-react with one or more of M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF for binding to mesothelioma cell (e.g., M28 cell line), Monoclonal Antibodies.

Monoclonal antibodies that bind ALPP and/or ALPPL2, preferably binding the epitope bound by one or more of M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF can be produced using a variety of known techniques, such as the standard somatic cell hybridization technique described by Kohler and Milstein (1975) *Nature* 256: 495, viral or oncogenic transformation of B lymphocytes or phage display technique using libraries of human antibody genes. In particular embodiments, the antibodies are fully human monoclonal antibodies.

Accordingly, in one embodiment, a hybridoma method is used for producing an antibody that binds ALPP and/or ALPPL2. In this method, a mouse or other appropriate host animal can be immunized with a suitable antigen in order to elicit lymphocytes that produce or are capable of producing antibodies that will specifically bind to the antigen used for immunization. Alternatively, lymphocytes may be immunized in vitro. Lymphocytes can then be fused with myeloma cells using a suitable fusing agent, such as polyethylene glycol, to form a hybridoma cell (Goding (1986) Monoclonal Antibodies: Principles and Practice, pp. 59-103 (Academic Press)). Culture medium in which hybridoma cells are growing is assayed for production of monoclonal antibodies directed against the antigen. After hybridoma cells are identified that produce antibodies of the desired specificity, affinity, and/or activity, the clones may be subcloned by limiting dilution procedures and grown by standard methods (Id.). Suitable culture media for this purpose include, for example, D-MEM or RPMI-1640 medium. In addition, the hybridoma cells may be grown in vivo as ascites tumors in an animal. The monoclonal antibodies secreted by the subclones can be separated from the culture medium, ascites fluid, or serum by conventional immunoglobulin purification procedures such as, for example, protein A-Sepharose, hydroxylapatite chromatography, gel electrophoresis, dialysis, or affinity chromatography.

In another embodiment, antibodies and antibody portions that bind ALPP and/or ALPPL2 can be isolated from antibody phage libraries generated using the techniques described in, for example, McCafferty et al. (1990) *Nature,* 348: 552-554, Clackson et al. (1991) *Nature,* 352:624-628, Marks et al. (1991) *J. Mol. Biol.,* 222: 581-597, Hoet et al (2005) *Nature Biotechnol.,* 23: 344-348; U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al. Additionally, production of high affinity (nM range) human antibodies by chain shuffling (Marks et al. (1992) *Bio/Technology,* 10:779-783), as well as combinatorial infection and in vivo recombination as a strategy for constructing very large phage libraries (Waterhouse et al. (1993) *Nucl. Acids. Res.,* 21: 2265-2266) may also be used.

In a particular embodiment, the monoclonal antibody or antigen binding portion thereof that binds ALPP and/or ALPPL2, preferably binding the epitope of bound by one or more of M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF is produced using the phage display technique described by Hoet et al., supra. This technique involves the generation of a human Fab library having a unique combination of immunoglobulin sequences isolated from human donors and having synthetic diversity in the heavy-chain CDRs is generated. The library is then screened for Fabs that bind to ALPP and/or ALPPL2, preferably competing for binding with one or more of M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF.

In yet another embodiment, human monoclonal antibodies directed against ALPP and/or ALPPL2, preferably comprising the epitope bound by one or more of M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF can be generated using transgenic or transchromosomic mice carrying parts of the human immune system rather than the mouse system (see e.g., Lonberg, et al. (1994) *Nature* 368(6474): 856-859; Lonberg and Huszar, (1995) *Intern. Rev. Immunol.* 13: 65-93, Harding and Lonberg (1995) *Ann. NY. Acad. Sci.* 764: 536-546, and U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.).

In another embodiment, human antibodies directed against ALPP and/or ALPPL2 preferably binding the epitope bound by one or more of M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF can be raised using a mouse that carries human immunoglobulin sequences on transgenes and transchomosomes, such as a mouse that carries a human heavy chain transgene and a human light chain transchromosome (see, e.g., PCT Publication WO 02/43478 to Ishida et al.).

Alternative transgenic animal systems expressing human immunoglobulin genes are available in the art and can be used to raise anti-ALPP/ALPPL2 antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Alternative transchromosomic animal systems expressing human immunoglobulin genes are available in the art and can be used to raise anti-ALPP/ALPPL2 antibodies contemplated herein. For example, mice carrying both a human heavy chain transchromosome and a human light chain tranchromosome can be used; as described in Tomizuka et al. (2000) *Proc. Natl. Acad. Sci. USA* 97: 722-727. Furthermore, cows carrying human heavy and light chain transchromosomes have been described in the art (see, e.g., Kuroiwa et al. (2002) *Nature Biotechnology* 20: 889-894) and can be used to raise anti-ALPP and/or ALPPL2 antibodies.

In yet another embodiment, antibodies that specifically bind ALPP and/or ALPPL2 preferably binding the epitope bound by one or more of M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF can be prepared using a transgenic plant and/or cultured plant cells (such as, for example, tobacco, maize and duckweed) that produce such antibodies. For example, transgenic tobacco leaves expressing antibodies or antigen binding portions thereof can be used to produce such antibodies by, for example, using an inducible promoter (see, e.g., Cramer et al. (1999) *Curr. Top. Microbol. Immunol.* 240: 95-118). Also, transgenic maize can be used to express such antibodies and antigen binding portions thereof (see, e.g., Hood et al. (1999) *Adv. Exp. Med. Biol.* 464: 127-147). Antibodies can also be produced in large amounts from transgenic plant seeds including antibody portions, such as single chain antibodies (scFv's), for example, using tobacco seeds and potato tubers (see, e.g., Conrad et al. (1998) *Plant Mol. Biol.* 38: 101-109). Methods of producing antibodies or antigen binding portions in plants can also be found in, e.g., Fischer et al. (1999) *Biotechnol. ALPP. Biochem.* 30: 99-108, Ma et al. (1995) *Trends Biotechnol.* 13: 522-527, Ma et al. (1995) *Plant Physiol.* 109: 341-346; Whitelam et al. (1994) *Biochem. Soc. Trans.* 22: 940-944, and U.S. Pat. Nos. 6,040,498 and 6,815,184.

The binding specificity of monoclonal antibodies or portions thereof that bind ALPP and/or ALPPL2, preferably binding the epitope bound by one or more of M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF can be prepared using any technique including those disclosed here, can be determined by immunoprecipitation or by an in vitro binding assay, such as radioimmunoassay (MA) or enzyme-linked immunoabsorbent assay (ELISA). The binding affinity of a monoclonal antibody or portion thereof also can be determined by the Scatchard analysis of Munson et al. (1980) *Anal. Biochem.*, 107:220.

Cross-Reactivity with M25AD, MD25ADX, M25, ALPPL2rd3_1, ALPPL2rd3_2, M25AG, M25AS, M25AV, and/or M25AL.

In another approach, antibodies that bind ALPP and/or ALPPL2 can be identified by the fact that they bind the same epitope as the "prototypic" antibodies described herein (e.g., M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF). To identify such antibodies, it is not necessary to isolate the subject epitope. In certain embodiments, one can screen, e.g. antibody libraries for antibodies that compete with the prototypic antibodies of this invention for binding by a cell that expresses ALPP/ALPP2 (e.g. mesothelioma cell such as M28, etc.), and/or for binding to ALPP/ALPPL2.

Methods of screening libraries for epitope binding and/or cell binding and/or internalization are well known to those of skill in the art. In certain embodiments, cross-reactive anti-ALPP and/or ALPPL2 antibodies show at least 60%, preferably 80%, more preferably 90%, and most preferably at least 95% or at least 99% cross-reactivity with the one or more of the M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF antibodies described herein.

Phage Display Methods to Select Other "Related" Anti-ALPP/ALPPL2 Antibodies.

Using the known sequences for the M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF antibodies, a variety of phage display (or yeast display) methods can be used to generate other antibodies that antibodies that specifically bind ALPP/ALPPL2, preferably binding the epitope bound by M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF with the same or even greater affinity.

Chain Shuffling Methods.

One approach to creating antibody variants has been to replace the original $V_H$ or $V_L$ gene with a repertoire of V-genes to create new partners (chain shuffling) (Clackson et al. (1991) Nature. 352: 624-628) in a phage display or yeast display library. Using chain shuffling and phage display, the affinity of a human scFv antibody fragment that bound the hapten phenyloxazolone (phOx) was increased from 300 nM to 1 nM (300 fold) (Marks et al. (1992) Bio/Technology 10: 779-783).

Thus, for example, to alter the affinity of an anti-ALPP/ALPPL2 antibody described herein, a mutant scFv gene repertoire can be created containing a $V_H$ gene of the prototypic M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF antibody and a human $V_L$ gene repertoire (light chain shuffling). The scFv gene repertoire can be cloned into a phage display vector, e.g., pHEN-1 (Hoogenboom et al. (1991) Nucleic Acids Res., 19: 4133-4137) or other vectors, and after transformation a library of transformants is obtained.

Similarly, for heavy chain shuffling, a mutant scFv gene repertoire can be created containing a $V_L$ gene of the prototypic M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF antibody and a human $V_H$ gene repertoire (heavy chain shuffling). The scFv gene repertoire can be cloned into a phage display vector, e.g., pHEN-1 (Hoogenboom et al. (1991) Nucleic Acids Res., 19: 4133-4137) or other vectors, and after transformation a library of transformants is obtained.

The resulting libraries can be screened against the relevant target (e.g., ALPP/ALPPL2, cells expressing ALPP/ALPPL2) and/or for cross-reactivity with M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF.

Site-Directed Mutagenesis to Improve Binding Affinity.

The majority of antigen contacting amino acid side chains are typically located in the complementarity determining regions (CDRs), three in the $V_H$ (CDR1, CDR2, and CDR3) and three in the $V_L$ (CDR1, CDR2, and CDR3) (Chothia et al. (1987) J. Mol. Biol., 196: 901-917; Chothia et al. (1986) Science, 233: 755-8; Nhan et al. (1991) J. Mol. Biol., 217: 133-151). These residues contribute the majority of binding energetics responsible for antibody affinity for antigen. In other molecules, mutating amino acids which contact ligand has been shown to be an effective means of increasing the affinity of one protein molecule for its binding partner (Lowman et al. (1993) J. Mol. Biol., 234: 564-578; Wells (1990) Biochemistry, 29: 8509-8516). Site-directed mutagenesis of CDRs and screening against cells/cell lines that express ALPP/ALPPL2 e.g. as described herein can produce antibodies having improved binding affinity.

CDR Randomization to Produce Higher Affinity Human scFv.

In an extension of simple site-directed mutagenesis, mutant antibody libraries can be created where partial or entire CDRs are randomized ($V_L$ CDR1 CDR2 and/or CDR3 and/or $V_H$ CDR1, CDR2 and/or CDR3). In one embodiment, each CDR is randomized in a separate library, using a known antibody (e.g., M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF) as a template. The CDR sequences of the highest affinity mutants from each CDR library are combined to obtain an additive increase in affinity. A similar approach has been used to increase the affinity of human growth hormone (hGH) for the growth hormone receptor over 1500 fold from $3.4 \times 10^{10}$ to $9.0 \times 10^{13}$ M (Lowman et al. (1993) J. Mol. Biol., 234: 564-578).

$V_H$ CDR3 often occupies the center of the binding pocket, and thus mutations in this region are likely to result in an increase in affinity (Clackson et al. (1995) Science, 267: 383-386). In one embodiment, $V_H$ CDR3 residues are randomized (see, e.g., Schier et al. (1996) Gene, 169: 147-155; Schier and Marks (1996) Human Antibodies and Hybridomas. 7: 97-105, 1996; and Schier et al. (1996) J. Mol. Biol. 263: 551-567).

Other Antibody Modifications.

In one embodiment, partial antibody sequences derived from the M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF antibody may be used to produce structurally and functionally related antibodies. For example, antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al. (1998) *Nature* 332: 323-327; Jones et al., (1986) *Nature* 321: 522-525; and Queen et al. (1989) *Proc. Natl. Acad. Sci. USA,* 86: 10029-10033). Such framework sequences can be obtained from public DNA databases that include germline antibody gene sequences.

Thus, one or more structural features of an anti-ALPP/ALPPL2 antibody, such as the CDRs, can be used to create structurally related anti-ALPP/ALPPL2 antibodies that retain at least one functional property of, for example, the M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLFantibody, e.g., binding to tumor cells that express ALPPL2.

In a particular embodiment, one or more M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF CDR regions (e.g. VH CDR1, and/or CDR2, and/or CDR3, and/or VL CDR1, and/or CDR2, and/or CDR3) is combined recombinantly with known human framework regions and CDRs to create additional, recombinantly-engineered, anti-ALPP/ALPPL2 antibodies. The heavy and light chain variable framework regions can be derived from the same or different antibody sequences.

It is well known in the art that antibody heavy and light chain CDR3 domains play a particularly important role in the binding specificity/affinity of an antibody for an antigen (see, e.g., Hall et al. (1992) *J. Immunol.,* 149: 1605-1612; Polymenis et al. (1994) *J. Immunol.,* 152: 5318-5329; Jahn et al. (1995) *J. Immunobiol.,* 193:400-419; Klimka et al. (2000) *Brit. J. Cancer,* 83: 252-260; Beiboer et al. (2000) *J. Mol. Biol,* 296: 833-849; Rader et al. (1998) *Proc. Natl. Acad. Sci. USA,* 95: 8910-8915; Barbas et al. (1994) *J Am. Chem. Soc.,* 116: 2161-2162; Ditzel et al. (1996) *J. Immunol.,* 157: 739-749). Accordingly, in certain embodiments, antibodies are generated that include the heavy and/or light chain CDR3s of the particular antibodies described herein (e.g., M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF). Accordingly, in certain embodiments, antibodies are generated that include the heavy and/or light chain CDR1s of the particular antibodies described herein (e.g., M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF). The antibodies can further include the other heavy and/or light chain CDRs of the antibodies of the present invention (e.g., M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF).

In certain embodiments the CDR1, 2, and/or 3 regions of the engineered antibodies described above can comprise the exact amino acid sequence(s) as those disclosed herein (e.g., CDRs of M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF). However, the ordinarily skilled artisan will appreciate that some deviation from the exact CDR sequences may be possible while still retaining the ability of the antibody to bind ALPP and/or ALPPL2 effectively (e.g., conservative amino acid substitutions). Accordingly, in another embodiment, the engineered antibody may be composed of one or more CDRs that are, for example, 90%, 95%, 98%, 99% or 99.5% identical to one or more CDRs of the M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF antibody.

In another embodiment, one or more residues of a CDR may be altered to modify binding to achieve a more favored on-rate of binding. Using this strategy, an antibody having ultra-high binding affinity of, for example, $10^{10}$ M$^{-1}$ or more, can be achieved. Affinity maturation techniques, well known in the art and those described herein, can be used to alter the CDR region(s) followed by screening of the resultant binding molecules for the desired change in binding. Accordingly, as CDR(s) are altered, changes in binding affinity as well as immunogenicity can be monitored and scored such that an antibody optimized for the best combined binding and low immunogenicity are achieved.

In addition to, or instead of, modifications within the CDRs, modifications can also be made within one or more of the framework regions, FR1, FR2, FR3 and FR4, of the heavy and/or the light chain variable regions of an antibody, so long as these modifications do not eliminate the binding affinity of the antibody.

In another embodiment, the antibody is further modified with respect to effector function, so as to enhance the effectiveness of the antibody in treating cancer, for example. For example cysteine residue(s) may be introduced in the Fc region, thereby allowing interchain disulfide bond formation in this region. The homodimeric antibody thus generated may have increased complement-mediated cell killing and antibody-dependent cellular cytotoxicity (ADCC) (see, e.g., Caron et al. (1992) *J. Exp Med.* 176: 1191-1195; Shopes (1992) *J. Immunol.* 148: 2918-2922). Homodimeric antibodies with enhanced anti-tumor activity may also be prepared using heterobifunctional cross-linkers (see, e.g., Wolff et al. (1993) *Cancer Res.* 53:2560-2565). Alternatively, an antibody can be engineered which has dual Fc regions and may thereby have enhanced complement lysis and ADCC capabilities (see, e.g., Stevenson et al. (1989) *Anti-Cancer Drug Design* 3: 219-230).

In some instances, Fv framework region (FR) residues of the human immunoglobulin are replaced by corresponding non-human residues. In certain embodiments the antibody may include residues that are found neither a human framework nor in a non-human framework, but are included to further refine and optimize antibody performance. In certain embodiments the antibodies can have Fc regions modified as described in PCT International Publication No. WO 99/58572.

Antibody Production.

In various embodiments antibodies described herein can be produced by chemical synthesis or can be recombinantly expressed.

Chemical Synthesis.

Using the sequence information provided herein, the anti-ALPPL2 specific antibodies described herein (e.g., M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF), or variants thereof, can be chemically synthesized using well known methods of peptide synthesis. Solid phase synthesis in which the C-terminal amino acid of the sequence is attached to an insoluble support followed by sequential addition of the remaining amino acids in the sequence is one preferred method for the chemical synthesis of single chain antibodies. Techniques for solid phase synthesis are described by Barany and Merrifield, *Solid Phase Peptide Synthesis*; pp. 3-284 in *The Peptides: Analysis, Synthesis, Biology*. Vol. 2: *Special Methods in Peptide Synthesis*, Part A., Merrifield et al. (1963) *J. Am. Chem. Soc.,* 85: 2149-2156, and Stewart et al. (1984) *Solid Phase Peptide Synthesis, 2nd ed*. Pierce Chem. Co., Rockford, Ill.

Recombinant Expression of Anti-ALPPL2/ALPPL Antibodies.

In certain embodiments, the anti-ALPPL2/ALPPL specific antibodies described herein (e.g., M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF), or variants thereof, are recombinantly expressed using methods well known to those of skill in the art. For example, using the M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF sequence information provided herein, nucleic acids encoding the desired antibody can be prepared according to a number of standard methods known to those of skill in the art. The nucleic acids are transfected into host cells that then express the desired antibody or a chain thereof.

Molecular cloning techniques to achieve these ends are known in the art. A wide variety of cloning and in vitro amplification methods are suitable for the construction of recombinant nucleic acids. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, N.Y., (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Methods of producing recombinant immunoglobulins are also known in the art. See, Cabilly, U.S. Pat. No. 4,816,567; and Queen et al. (1989) *Proc. Natl Acad. Sci. USA* 86: 10029-10033. In addition, detailed protocols for the expression of antibodies are also provided by Liu et al. (2004) *Cancer Res.* 64: 704-710, Poul et al. (2000) *J. Mol. Biol.* 301: 1149-1161, and the like.

Creation of Other Antibody Forms.

Using the known and/or identified sequences (e.g. $V_H$ and/or $V_L$ sequences) of the single chain antibodies provided herein other antibody forms can readily be created. Such forms include, but are not limited to multivalent antibodies, full antibodies, scFv, (scFv')$_2$, Fab, (Fab')$_2$, chimeric antibodies, and the like.

Creation of Homodimers.

For example, to create (scFv')$_2$ antibodies, two anti-ALPP/ALPPL2 antibodies are joined, either through a linker (e.g., a carbon linker, a peptide, etc.) or through a disulfide bond between, for example, two cysteins. Thus, for example, to create disulfide linked scFv, a cysteine residue can be introduced by site directed mutagenesis at the carboxy-terminus of the antibodies described herein.

An scFv can be expressed from this construct, purified by IMAC, and analyzed by gel filtration. To produce (scFv')$_2$ dimers, the cysteine is reduced by incubation with 1 mM 3-mercaptoethanol, and half of the scFv blocked by the addition of DTNB. Blocked and unblocked scFvs are incubated together to form (scFv')$_2$ and the resulting material can be analyzed by gel filtration. The affinity of the resulting dimmer can be determined using standard methods, e.g. by BIAcore.

In one illustrative embodiment, the (scFv')$_2$ dimer is created by joining the scFv' fragments through a linker, e.g., through a peptide linker. This can be accomplished by a wide variety of means well known to those of skill in the art. For example, one approach is described by Holliger et al. (1993) *Proc. Natl. Acad. Sci. USA,* 90: 6444-6448 (see also WO 94/13804).

It is noted that using the $V_H$ and/or $V_L$ sequences provided herein Fabs and (Fab')$_2$ dimers can also readily be prepared. Fab is a light chain joined to $V_H$-$C_H$1 by a disulfide bond and can readily be created using standard methods known to those of skill in the art. The F(ab)'$_2$ can be produced by dimerizing the Fab, e.g. as described above for the (scFv')$_2$ dimer.

Chimeric Antibodies.

The antibodies contemplated herein also include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; Morrison et al. (1984) *Proc. Natl. Acad. Sci.* 81: 6851-6855, etc.).

While the prototypic antibodies provided herein (e.g., M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF) are fully human antibodies, chimeric antibodies are contemplated, particularly when such antibodies are to be used in species other than humans (e.g., in veterinary applications). Chimeric antibodies are antibodies comprising portions from two different species (e.g. a human and non-human portion). Typically, the antigen combining region (or variable region) of a chimeric antibody is derived from a one species source and the constant region of the chimeric antibody (which confers biological effector function to the immunoglobulin) is derived from another source. A large number of methods of generating chimeric antibodies are well known to those of skill in the art (see, e.g., U.S. Pat. Nos. 5,502,167, 5,500,362, 5,491,088, 5,482,856, 5,472, 693, 5,354,847, 5,292,867, 5,231,026, 5,204,244, 5,202,238, 5,169,939, 5,081,235, 5,075,431, and 4,975,369, and PCT Application WO 91/0996).

In general, the procedures used to produce chimeric antibodies consist of the following steps (the order of some steps may be interchanged): (a) identifying and cloning the correct gene segment encoding the antigen binding portion of the antibody molecule; this gene segment (known as the VDJ, variable, diversity and joining regions for heavy chains or VJ, variable, joining regions for light chains, or simply as the V or variable region or $V_H$ and $V_L$ regions) may be in either the cDNA or genomic form; (b) cloning the gene segments encoding the human constant region or desired part thereof; (c) ligating the variable region to the constant region so that the complete chimeric antibody is encoded in a transcribable and translatable form; (d) ligating this construct into a vector containing a selectable marker and gene control regions such as promoters, enhancers and poly(A) addition signals; (e) amplifying this construct in a host cell (e.g., bacteria); (f) introducing the DNA into eukaryotic cells (transfection) most often mammalian lymphocytes; and culturing the host cell under conditions suitable for expression of the chimeric antibody.

Antibodies of several distinct antigen binding specificities have been manipulated by these protocols to produce chimeric proteins (e.g., anti-TNP: Boulianne et al. (1984) *Nature,* 312: 643) and anti-tumor antigens (see, e.g., Sahagan et al. (1986) *J. Immunol.,* 137: 1066). Likewise several different effector functions have been achieved by linking new sequences to those encoding the antigen binding region. Some of these include enzymes (Neuberger et al. (1984) *Nature* 312: 604), immunoglobulin constant regions from another species and constant regions of another immunoglobulin chain (Sharon et al. (1984) *Nature* 309: 364; Tan et al., (1985) *J. Immunol.* 135: 3565-3567).

In certain embodiments, a recombinant DNA vector is used to transfect a cell line that produces an anti-ALPP/ ALPPL2 (e.g., M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF) antibody. The novel recombinant DNA vector contains a "replacement gene" to replace all or a portion of the gene encoding the immunoglobulin constant region in the cell line (e.g., a replacement gene may encode all or a portion of a constant region of a human immunoglobulin, a specific immunoglobulin class, or an enzyme, a toxin, a biologically active peptide, a growth factor, inhibitor, or a linker peptide to facilitate conjugation to a drug, toxin, or other molecule, etc.), and a "target sequence" that allows for targeted homologous recombination with immunoglobulin sequences within the antibody producing cell.

In another embodiment, a recombinant DNA vector is used to transfect a cell line that produces an antibody having a desired effector function, (e.g., a constant region of a human immunoglobulin) in which case, the replacement gene contained in the recombinant vector may encode all or a portion of a region of an ALPPL2/ALPP specific antibody and the target sequence contained in the recombinant vector allows for homologous recombination and targeted gene modification within the antibody producing cell. In either embodiment, when only a portion of the variable or constant region is replaced, the resulting chimeric antibody can define the same antigen and/or have the same effector function yet be altered or improved so that the chimeric antibody may demonstrate a greater antigen specificity, greater affinity binding constant, increased effector function, or increased secretion and production by the transfected antibody producing cell line, etc.

Regardless of the embodiment practiced, the processes of selection for integrated DNA (via a selectable marker), screening for chimeric antibody production, and cell cloning, can be used to obtain a clone of cells producing the chimeric antibody.

Thus, a piece of DNA that encodes a modification for a monoclonal antibody can be targeted directly to the site of the expressed immunoglobulin gene within a B-cell or hybridoma cell line. DNA constructs for any particular modification can be made to alter the protein product of any monoclonal cell line or hybridoma. The level of expression of chimeric antibody should be higher when the gene is at its natural chromosomal location rather than at a random position. Detailed methods for preparation of chimeric (humanized) antibodies can be found in U.S. Pat. No. 5,482,856.

Intact Human Antibodies.

In another embodiment, this invention provides for intact, fully human anti-ALPP/ALPPL2 antibodies. Such antibodies can readily be produced in a manner analogous to making chimeric human antibodies. In this instance, the VH and VL domains described herein are fully human and can readily be engineered into a substantially complete antibody (e.g., IgG, IgA, IgM, etc.).

For example, methods of converting scFv into fully human substantially full-length immunoglobulins are described, inter alia, by Braren et al. (2007) *Clin. Chem.,* 53(5): 837-844. In one approach described by Braren et al. (Id.) the human immunoglobulin constant regions are synthesized from cDNA derived from human peripheral blood mononuclear cells employing standard reaction conditions. The genes for human IgG1 and IgG4 heavy chain constant regions (IGHG1 and IGHG44) are amplified using PCR primers containing an AscI and a KpnI site (γ1: GAT CGG TAC CGA TCG GCG CGC CCA AAT CTT GTG ACA AAA CT CAC (SEQ ID NO:54), γ4: GAT CGG CGC GCC TTC CAC CAA GGG CCC ATC CGT CTT CCC CCT (SEQ ID NO:55)) and a SfiI site (γ1: GAT CGG CCC AGC CGG CCT CAT TTA CCC GGA GAC A GG GAG AGG CTC TTC (SEQ ID NO:56), γ4: GAT CGG CCC AGC CGG CCT CAT TTA CCC AGA GAC AGG GA (SEQ ID NO:57)), the γ1 CF$_H$2-3 and γ4 CF$_H$2-3 domains using primers containing an AscI and a KpnI site (γ1: GAT CTC TAG ATC ATT TAC CCG GAG ACA GGG AGA GGC TCT TC (SEQ ID NO:58), γ1: GAT CGG CGC GCC CAG CAA CAC CAA GGT GGA CA (SEQ ID NO:59)) and a XbaI site (γ1: GAT CGG CGC GCC AGC CTC CAC CAA GGG CCC AT (SEQ ID NO:60), γ1: GAT CTC TAG ATC ATT TAC CCA GAG ACA GGG A (SEQ ID NO:83)).

For amplification of the genes for the human IgE heavy chain constant regions (IGHE) primers can be used containing an AscI site (GAT CGG CGC GCC CAT CCG TCT TCC CCT TGA (SEQ ID NO:61)), an SfiI site, a 4× his-tag (GAT CGG CCC AGC CGG CCT CAT TTA CCG GGA TTT ACA GAC AC (SEQ ID NO:62)), and for the εC$_H$2-4 domains primers containing an AscI site (GAT CGG CGC GCC CAC CGT GAA GAT CTT AC (SEQ ID NO:63)), an XbaI site, and a 4× his-tag (GAT CTC TAG ATC AAT GGT GGT GAT GTT TAC CGG GAT TTA CAG ACA CCG (SEQ ID NO:64)) can be used. The signal sequence of a gene for rat κ light chain is synthesized by PCR primers containing a NheI site (GTA CGC TAG CAA GAT GGA ATC ACA GAC CCA GGT CCT CAT GTC CCT GCT GCT CTG GAT TTC (SEQ ID NO:65)) and a KpnI site (CAT GTC CCT GCT GCT CTG GAT TTC TGG TAC CTG TGG GGT GAG TCC TTA CAA CGC GTG TAC (SEQ ID NO:66)). After introduction of the leader sequence into the mammalian expression vector, e.g., pcDNA3.1-zeo (Invitrogen Life Technologies), one can insert the individual Ig domains, the Fc domains, and the entire heavy chains γ1, γ4, and ε via the XbaI and the AscI sites. Transfer of the particular scFv into the scFv-C$_H$2-3 or scFv-C$_H$2-4 format can be performed by introduction by PCR of a BsiWI site at the N-terminus and an AscI site at the C-terminus. Subsequently, the DNA can be ligated into the vectors containing the signal sequence and the particular constant regions.

For expression of the heterotetrameric IgG and IgE formats the mammalian expression vector pBudCE4.1 (Invitrogen Life Technologies) can be used. The human light chain constant domain (IGKC) can be amplified using one PCR primer containing an XbaI site and another primer containing an SgfI site (GAT CTC TAG ACT AAC ACT CTC CCC TGT TGA AGC (SEQ ID NO:67) and GAT CGC GAT CGC ACG AAC TGT GGC TGC ACC ATC TGT C (SEQ ID NO:68)). The two human signal sequences VH3-64 and Vκ1 can be synthesized by PCR using primers with an NotI and an internal SwaI or an SalI and an internal SbfI site for insertion of the variable regions (AGA ATG CGG CCG CTA TGG AAT TGG GGC TGA GCT GGG TTT TCC TTG TTG C TAT ATT TAAA TGT GTC CAG TGT (SEQ ID NO:69) and GAT CGT CGA CAT GGA CAT GAG GGT CCC CGC TCA GCT CCT GGG GCT CCT GCT ACT CTG CCT GCA GGG TGC CAG ATG T (SEQ ID NO:70)). After assembly of the leader sequences and the constant regions, the variable regions can then be introduced via the SgfI and the SbfI sites, or the AscI and SwaI sites, respectively. Finally, the entire light chain sequence including the leader sequence can be introduced via the XbaI and the SalI sites and the entire heavy chain including the leader sequence via the NotI site and the SfiI site into the expression vector, e.g., pBudCE4.1.

These approaches are illustrative and not limiting. Numerous other methods of converting scFv and other antibody fragments into full length immunoglobulins are known to those of skill in the art.

Diabodies.

In certain embodiments, diabodies comprising one or more of the V$_H$ and V$_L$ domains described herein are contemplated. The term "diabodies" refers to antibody fragments typically having two antigen-binding sites. The fragments typically comprise a heavy chain variable domain (V$_H$) connected to a light chain variable domain (V$_L$) in the same polypeptide chain (V$_H$-V$_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Holliger et al. (1993) *Proc. Natl. Acad. Sci. USA* 90: 6444-6448.

Unibodies.

In certain embodiments using the sequence information provided herein, the anti-ALPP/ALPPL2 antibodies can be constructed as unibodies. UniBody are antibody technology that produces a stable, smaller antibody format with an anticipated longer therapeutic window than certain small antibody formats. In certain embodiments unibodies are produced from IgG4 antibodies by eliminating the hinge region of the antibody. Unlike the full size IgG4 antibody, the half molecule fragment is very stable and is termed a uniBody. Halving the IgG4 molecule leaves only one area on the UniBody that can bind to a target. Methods of producing unibodies are described in detail in PCT Publication WO2007/059782, which is incorporated herein by reference in its entirety (see, also, Kolfschoten et al. (2007) *Science* 317: 1554-1557).

Affibodies.

In certain embodiments the sequence information provided herein is used to construct affibody molecules that bind ALPP/ALPPL2. Affibody molecules are class of affinity proteins based on a 58-amino acid residue protein domain, derived from one of the IgG-binding domains of staphylococcal protein A. This three helix bundle domain has been used as a scaffold for the construction of combinatorial phagemid libraries, from which affibody variants that target the desired molecules can be selected using phage display technology (see, e.g, Nord et al. (1997) *Nat. Biotechnol.* 15: 772-777; Ronmark et al. (2002) *Eur. J. Biochem.*, 269: 2647-2655.). Details of Affibodies and methods of production are known to those of skill (see, e.g., U.S. Pat. No. 5,831,012 which is incorporated herein by reference in its entirety).

It will be recognized that the antibodies described above can be provided as whole intact antibodies (e.g., IgG), antibody fragments, or single chain antibodies, using methods well known to those of skill in the art. In addition, while the antibody can be from essentially any mammalian species, to reduce immunogenicity, it is desirable to use an antibody that is of the species in which the antibody and/or immunoconjugate is to be used. In other words, for use in a human, it is desirable to use a human, humanized, or chimeric human antibody.

Measurement of Antibody/Polypeptide Binding Affinity.

As explained above, selection for increased avidity can involves measuring the affinity of the antibody for the target antigen (e.g., ALPPL2, especially the epitope bound by one or more of M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF). Methods of making such measurements are well known to those of skill in the art. Briefly, for example, the $K_d$ of the antibody is determined from the kinetics of binding to, e.g. the target cell in a BIAcore, a biosensor based on surface plasmon resonance. For this technique, the antigen or cell (e.g., a cell that expresses ALPPL2) is coupled to a derivatized sensor chip capable of detecting changes in mass. When antibody is passed over the sensor chip, antibody binds to the antigen resulting in an increase in mass that is quantifiable. Measurement of the rate of association as a function of antibody concentration can be used to calculate the association rate constant ($k_{on}$). After the association phase, buffer is passed over the chip and the rate of dissociation of antibody ($k_{off}$) determined. $K_{on}$, is typically measured in the range $1.0 \times 10^2$ to $5.0 \times 10^6$ and $k_{off}$ in the range $1.0 \times 10^{-1}$ to $1.0 \times 10^{-6}$. The equilibrium constant $K_d$ is often calculated as $k_{off}/k_{on}$ and thus is typically measured in the range $10^{-5}$ to $10^{-12}$. Affinities measured in this manner correlate well with affinities measured in solution by fluorescence quench titration.

Immunoconjugates Comprising Antibodies that Specifically Bind ALPP/ALPPL2.

The prototypical anti-ALPP/ALPPL2 antibodies (e.g., M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF) described herein specifically bind to cancer cells expressing ALPPL2 (e.g., cells of cancers including, but not limited to mesothelioma, testicular cancer, endometrial cancer, ovarian cancer, pancreatic cancer, and non small cell lung cancer). The antibodies can be used alone as therapeutics (e.g., to inhibit growth and/or proliferation of a cancer cell expressing ALPPL2 or they can be coupled to an effector forming immunoconjugates that provide efficient and specific delivery of the effector (e.g. cytotoxins, labels, radionuclides, ligands, antibodies, drugs, liposomes, nanoparticles, viral particles, cytokines, immunomodulatory molecules, and the like) to various cancer cells that express ALPPL2 (e.g., isolated cancer cells, cancer stem cells, metastatic cells, solid tumor cells, etc.).

Anti-ALPP/ALPPL2 immunoconjugates can be formed by conjugating the antibodies or antigen binding portions thereof described herein to an effector (e.g., a detectable label, another therapeutic agent, etc.). Illustrative therapeutic agents include, but are not limited to, for example, a cytotoxic or cytostatic agent (e.g., a chemotherapeutic agent), a toxin (e.g. an enzymatically active toxin of bacterial, fungal, plant or animal origin, or fragments thereof), and/or a radioactive isotope (e.g., a radioconjugate), a second antibody.

Illustrative Effectors.

Detectable Labels—Imaging Compositions.

In certain embodiments, the anti-ALPP/ALPPL2 immunoconjugates can be used to direct detectable labels to a tumor site. This can facilitate tumor detection and/or localization. It can be effective for detecting primary tumors, or, in certain embodiments, secondary tumors produced by cancers that express ALPPL2 (e.g., cancers including, but not limited to mesothelioma, testicular cancer, endometrial cancer, ovarian cancer, pancreatic cancer, and non small cell lung cancer).

Thus, in certain embodiments, the effector comprises a detectable label. Suitable detectable labels include, but are not limited to radio-opaque labels, nanoparticles, PET labels, MRI labels, radioactive labels, and the like. Among the radionuclides and useful in various embodiments, gamma-emitters, positron-emitters, x-ray emitters and fluorescence-emitters are suitable for localization, diagnosis and/or staging, and/or therapy, while beta and alpha-emitters and electron and neutron-capturing agents, such as boron and uranium, also can be used for therapy.

In various embodiments the detectable labels can be used in conjunction with an external detector and/or an internal detector and provide a means of effectively localizing and/or visualizing cancer cells expressing ALPPL2. Such detection/visualization can be useful in various contexts including, but not limited to pre-operative and intraoperative settings. Thus, in certain embodiment this invention relates to a method of intraoperatively detecting cancers that express ALPPL2 in the body of a mammal. These methods typically involve administering to the mammal a composition comprising, in a quantity sufficient for detection by a detector (e.g. a gamma detecting probe), an anti-ALPPL2 antibody labeled with a detectable label as described herein, and, after allowing the active substance to be taken up by the target tissue, and preferably after blood clearance of the label, subjecting the mammal to a radioimmunodetection technique in the relevant area of the body, e.g. by using a gamma detecting probe.

In certain embodiments the label-bound antibody can be used in the technique of radioguided surgery, wherein relevant tissues in the body of a subject can be detected and located intraoperatively by means of a detector, e.g. a gamma detecting probe. The surgeon can, intraoperatively, use this probe to find the tissues in which uptake of the compound labeled with a radioisotope, that is, e.g. a low-energy gamma photon emitter, has taken place. In certain embodiments such methods are particularly useful in localizing and removing secondary cancers produced by metastatic cells from a primary tumor.

The anti-ALPP/ALPPL2 antibodies described herein can be coupled directly to the radio-opaque moiety (e.g., at an available cysteine) or they can be attached to a "package" (e.g., a chelate, a liposome, a polymer microbead, a nanoparticle, etc.) carrying, containing, or comprising the radio-opaque material, e.g., as described below.

In addition to radio-opaque labels, other labels are also suitable for use. Detectable labels suitable for use in immunoconjugates include any composition detectable by spectroscopic, photochemical, biochemical, immunochemical, electrical, optical or chemical means. Useful labels in the include magnetic beads (e.g., DYNABEADS™), fluorescent dyes (e.g., fluorescein isothiocyanate, texas red, rhodamine, green fluorescent protein, and the like), radiolabels (e.g., $^{3}$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads, nanoparticles, quantum dots, and the like.

In certain embodiments, suitable radiolabels include, but are not limited to $^{99}$Tc, $^{99}$Tc, $^{97}$Ru, $^{95}$Ru, $^{94}$Tc, $^{90}$Y, $^{90}$Y, $^{89}$Zr, $^{86}$Y, $^{77}$Br, $^{77}$As, $^{76}$Br, $^{75}$Se, $^{72}$As, $^{68}$Ga, $^{68}$Ga, $^{67}$Ga, $^{67}$Ga, $^{67}$Cu, $^{67}$Cu, $^{64}$Cu, $^{62}$Cu, $^{59}$Fe, $^{58}$Co, $^{57}$Co, $^{52}$Mn, $^{52}$Fe, $^{51}$Cr, $^{47}$Sc, $^{3}$H, $^{35}$S, $^{33}$P, $^{32}$P, $^{225}$Ac, $^{224}$Ac, $^{223}$Ra, $^{213}$Bi, $^{212}$Pb, $^{212}$Bi, $^{211}$At, $^{203}$Pb, $^{203}$Hg, $^{201}$Tl, $^{199}$Au, $^{198}$Au, $^{198}$Au, $^{197}$Pt, $^{18}$F, $^{189}$Re, $^{188}$Re, $^{188}$Re, $^{186}$Re, $^{186}$Re, $^{177}$Lu, $^{177}$Lu, $^{175}$Yb, $^{172}$Tm, $^{169}$Yb, $^{169}$Yb, $^{169}$Er, $^{168}$Tm, $^{167}$Tm, $^{166}$Ho, $^{166}$Dy, $^{165}$Tm, $^{165}$Dy, $^{161}$Tb, $^{15}$O, $^{15}$N, $^{159}$Gd, $^{157}$Gd, $^{153}$Sm, $^{153}$Pb, $^{151}$Pm, $^{14}$C, $^{149}$Pm, $^{143}$Pr, $^{142}$Pr, $^{13}$N, $^{133}$I, $^{131}$In, $^{131}$I, $^{127}$Te, $^{126}$I, $^{125}$Te, $^{125}$I, $^{124}$I, $^{123}$I, $^{122}$Te, $^{121}$Te, $^{121}$Sn, $^{11}$C, $^{113}$In, $^{111}$In, $^{111}$In, $^{111}$Ag, $^{111}$Ag, $^{109}$Pd, $^{109}$Pd, $^{107}$Hg, $^{105}$Ru, $^{105}$Rh, $^{105}$Rh, and $^{103}$Ru.

Means of detecting such labels are well known to those of skill in the art. Thus, for example, certain radiolabels may be detected using photographic film, scintillation detectors, PET imaging, MRI, and the like. Fluorescent markers can be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

Radiosensitizers.

In another embodiment, the effector can comprise a radiosensitizer that enhances the cytotoxic effect of ionizing radiation (e.g., such as might be produced by $^{60}$Co or an x-ray source) on a cell. Numerous radiosensitizing agents are known and include, but are not limited to benzoporphyrin derivative compounds (see, e.g., U.S. Pat. No. 5,945,439), 1,2,4-benzotriazine oxides (see, e.g., U.S. Pat. No. 5,849,738), compounds containing certain diamines (see, e.g., U.S. Pat. No. 5,700,825), BCNT (see, e.g., U.S. Pat. No. 5,872,107), radiosensitizing nitrobenzoic acid amide derivatives (see, e.g., U.S. Pat. No. 4,474,814), various heterocyclic derivatives (see, e.g., U.S. Pat. No. 5,064,849), platinum complexes (see, e.g., U.S. Pat. No. 4,921,963), and the like.

Alpha Emitters.

In certain embodiments, the effector can include an alpha emitter, i.e. a radioactive isotope that emits alpha particles. Alpha-emitters have recently been shown to be effective in the treatment of cancer (see, e.g., McDevitt et al. (2001) *Science* 294:1537-1540; Ballangrud et al. (2001) *Cancer Res.* 61: 2008-2014; Borchardt et al. (2003) *Cancer Res.* 63: 5084-50). Suitable alpha emitters include, but are not limited to Bi, $^{213}$Bi, $^{211}$At, and the like.

Chelates

Many of the pharmaceuticals and/or radiolabels described herein can be provided as a chelate. The chelating molecule is typically coupled to a molecule (e.g. biotin, avidin, streptavidin, etc.) that specifically binds an epitope tag attached to an anti-ALPP/ALPPL2 antibody (e.g., M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF) described herein.

Chelating groups are well known to those of skill in the art. In certain embodiments, chelating groups are derived from ethylene diamine tetra-acetic acid (EDTA), diethylene triamine penta-acetic acid (DTPA), cyclohexyl 1,2-diamine tetra-acetic acid (CDTA), ethyleneglycol-O,O'-bis(2-aminoethyl)-N,N,N',N'-tetra-acetic acid (EGTA), N,N-bis(hydroxybenzyl-ethylenediamine-N,N'-diacetic acid (HBED), triethylene tetramine hexa-acetic acid (TTHA), 1,4,7,10-tetraazacyclododecane-N,N'-,N'',N'''-tetra-acetic acid (DOTA), hydroxyethyldiamine triacetic acid (HEDTA), 1,4,8,11-tetra-azacyclotetradecane-N,N',N'',N'''-tetra-acetic acid (TETA), substituted DTPA, substituted EDTA, and the like.

Examples of certain preferred chelators include unsubstituted or, substituted 2-iminothiolanes and 2-iminothiacyclohexanes, in particular 2-imino-4-mercaptomethylthiolane.

One chelating agent, 1,4,7,10-tetraazacyclododecane-N, N, N'', N'''-tetraacetic acid (DOTA), is of particular interest because of its ability to chelate a number of diagnostically and therapeutically important metals, such as radionuclides and radiolabels.

Conjugates of DOTA and proteins such as antibodies have been described. For example, U.S. Pat. No. 5,428,156 teaches a method for conjugating DOTA to antibodies and antibody fragments. To make these conjugates, one carboxylic acid group of DOTA is converted to an active ester which can react with an amine or sulfhydryl group on the antibody or antibody fragment. Lewis et al. (1994) *Bioconjugate Chem.* 5: 565-576, describes a similar method wherein one carboxyl group of DOTA is converted to an active ester, and the activated DOTA is mixed with an antibody, linking the antibody to DOTA via the epsilon-amino group of a lysine residue of the antibody, thereby converting one carboxyl group of DOTA to an amide moiety.

In certain embodiments the chelating agent can be coupled, directly or through a linker, to an epitope tag or to a moiety that binds an epitope tag. Conjugates of DOTA and biotin have been described (see, e.g., Su (1995) *J. Nucl. Med.,* 36 (5 Suppl):154P, which discloses the linkage of DOTA to biotin via available amino side chain biotin derivatives such as DOTA-LC-biotin or DOTA-benzyl-4-(6-amino-caproamide)-biotin). Yau et al., WO 95/15335, disclose a method of producing nitro-benzyl-DOTA compounds that can be conjugated to biotin. The method comprises a cyclization reaction via transient projection of a hydroxy group; tosylation of an amine; deprotection of the transiently protected hydroxy group; tosylation of the deprotected hydroxy group; and intramolecular tosylate cyclization. Wu et al. (1992) *Nucl. Med. Biol.,* 19(2): 239-244 discloses a synthesis of macrocylic chelating agents for radiolabeling proteins with $^{111}$IN and $^{90}$Y. Wu et al. makes a labeled DOTA-biotin conjugate to study the stability and biodistribution of conjugates with avidin, a model protein for studies. This conjugate was made using a biotin hydrazide which contained a free amino group to react with an in situ generated activated DOTA derivative.

Cytotoxins/Cytostatic Agents.

The anti-ALPP/ALPPL2 antibodies described herein (e.g., M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF) can be used to deliver a variety of cytotoxic and/or cytostatic drugs including therapeutic drugs, a compound emitting radiation, cytotoxic molecules of plant, fungal, or bacterial origin, biological proteins, and mixtures thereof. In certain embodiments the cytotoxic drugs can comprise intracellularly acting cytotoxic drugs that are, e.g., small organic molecules, cytotoxic proteins or peptides, radiation emitters, including, for example, short-range, high-energy α-emitters as described above, and the like. Additional representative therapeutic agents include radioisotopes, chemotherapeutic agents, immunomodulatory agents, anti-angiogenic agents, anti-proliferative agents, pro-apoptotic agents, and cytolytic enzymes (e.g., RNAses). An agent may also include a therapeutic nucleic acid, such as a gene encoding an immunomodulatory agent, an anti-angiogenic agent, an anti-proliferative agent, or a pro-apoptotic agent. These drug descriptors are not mutually exclusive, and thus a therapeutic agent may be described using one or more of the above-noted terms. For example, selected radioisotopes are also cytotoxins. In various embodiments therapeutic agents may be prepared as pharmaceutically acceptable salts, acids or derivatives of any of the above.

In certain embodiments, the anti-ALPP/ALPPL2 antibody is attached to a therapeutic cytotoxic/cytostatic drug. In various embodiments the drugs being used to construct ADCs include, but are not limited to microtubule inhibitors and DNA-damaging agents, polymerase inhibitors (e.g., the polymerase II inhibitor, α-amanitin), and the like. In certain embodiments the antibody is conjugated to the drug directly or through a linker, while in other embodiments, the antibody is conjugated to a drug carrier (e.g., a liposome containing the drug, a polymeric drug carrier, a nanoparticle drug carrier, a lipid drug carrier, a dendrimeric drug carrier, and the like).

In certain embodiments the drug comprises a tubulin inhibitor, including, but not limited to auristatin, Dolastatin-10, synthetic derivatives of the natural product Dolastatin-10, and maytansine or a maytansine derivative.

In certain embodiments the drug comprises an auristatin. In certain embodiments the auristatin is selected from the group consisting of auristatin E (AE), auristatin EB (AEB), auristatin EFP (AEFP), Monomethyl Auristatin D (MMAD) or monomethyl dolastatin 10, Monomethyl Auristatin F (MMAF) or N-methylvaline-valine-dolaisoleuine-dolaproine-phenylalanine), Monomethyl Auristatin E (MMAE) or N-methylvaline-valine-dolaisoleuine-dolaproine-norephedrine, 5-benzoylvaleric acid-AE ester (AEVB), vcM MAE, and vcMMAF.

In certain embodiments the drug comprises an enediyne. Enediynes are a class of anti-tumor bacterial products characterized by either nine- and ten-membered rings or the presence of a cyclic system of conjugated triple-double-triple bonds. Exemplary enediynes include, but are not limited to, calicheamicin, esperamicin, and dynemicin. Calicheamicin is an enediyne antibiotic that was originally isolated as a natural product from the soil organism *Micromonospora echinospora* ssp. *calichensis* (Zein et al. Science 27; 240(4856):1198-1201, 1988). It generates double-strand DNA breaks and subsequently induces apoptosis in target cells (Zein et al. Science 27; 240(4856):1198-1201, 1988; Nicolaou et al. Chem. Biol. September; 1(1): 57-66, 1994; Prokop et al. Oncogene 22:9107-9120, 2003). In certain embodiments the drug comprises calicheamicin or a calicheamicin analog. Examples of calicheamicins and analogs thereof suitable for use anti-ALPPL2 immunoconjugates are disclosed, for example, in U.S. Pat. Nos. 4,671, 958 4,970,198, 5,053,394, 5,037,651, 5,079,233, 5,264,586, and 5,108,912, which are incorporated herein by reference in their entirety. In certain embodiments these compounds contain a methyltrisulfide that can be reacted with appropriate thiols to form disulfides, at the same time introducing a functional group such as a hydrazide or other functional group that is useful for conjugating calicheamicin to an anti-ALPPL2 antibody. Disulfide analogs of calicheamicin can also be used, for example, analogs described in U.S. Pat. Nos. 5,606,040 and 5,770,710, which are incorporated herein by reference in its entirety. In certain embodiments the disulfide analog is N-acetyl-gamma-calicheamicin dimethyl hydrazide.

In certain embodiments the drug comprises a geldanamycin. Geldanamycins are benzoquinone ansamycin antibiotic that bind to Hsp90 (Heat Shock Protein 90) and have been used antitumor drugs. Exemplary geldanamycins include, but are not limited to, 17-AAG (17-N-Allylamino-17-

Demethoxygeldanamycin), and 17-DMAG (17-Dimethylaminoethylamino-17-demethoxygeldanamycin).

In certain embodiments the drug comprises a maytansine. Maytansines or their derivatives maytansinoids inhibit cell proliferation by inhibiting the microtubules formation during mitosis through inhibition of polymerization of tubulin (see, e.g., Remillard et al. 91975) *Science* 189: 1002-1005). Illustrative maytansines include, but are not limited to, Mertansine (DM1); and an analogue of maytansine such as DM3 or DM4, as well as ansamitocin.

In certain embodiments the drug comprises a taxane. Taxanes are diterpenes that act as anti-tubulin agents or mitotic inhibitors. Exemplary taxanes include, but are not limited to, paclitaxel and docetaxel.

In certain embodiments the drug comprises a DNA interacting agent. In certain embodiments the DNA interacting agent includes, but is not limited to calicheamicins, duocarmycins, pyrrolobenzodiazepines (PBDs), and the like.

In another illustrative, but non-limiting embodiment, the drug comprises a duocarmycin. Duocarmycins are DNA damaging agents able to exert their mode of action at any phase in the cellular cycle. Agents that are part of this class of duocarmycins typically have potency in the low picomolar range. Illustrative duocarmyhcins (e.g., duocarmycin analogues) that can be used as effectors in the chimeric constructs contemplated herein include, but are not limited to duocarmycin A, duocarmycin B1, duocarmycin B2, duocarmycin C1, duocarmycin C2, duocarmycin D, duocarmycin SA, Cyclopropylbenzoindole duocarmycin (CC-1065), Centanamycin, Rachelmycin, Adozelesin, Bizelesin, Carzelesin, and the like.

In another illustrative, but non-limiting embodiment, the drug comprises a pyrrolobenzodiazepine. In certain embodiments the drug comprises a synthetic derivative of two pyrrolobenzodiazepines linked by a flexible polymethylene tether. Pyrrolobenzodiazepines (PBDs) and PBD dimers are described in U.S. Pat. No. 7,528,126 B2, which is incorporated herein by reference for the Pyrrolobenzodiazepines and PBD dimers described therein. In certain embodiments the pyrrolobenzodiazepine is selected from the group consisting of: Anthramycin (and dimers thereof), Mazethramycin (and dimers thereof), Tomaymycin (and dimers thereof), Prothracarcin (and dimers thereof), Chicamycin (and dimers thereof), Neothramycin A (and dimers thereof), Neothramycin B (and dimers thereof), DC-81 (and dimers thereof), Sibiromycin (and dimers thereof), Porothramycin A (and dimers thereof), Porothramycin B (and dimers thereof), Sibanomycin (and dimers thereof), Abbeymycin (and dimers thereof), SG2000, and SG2285.

In certain embodiments the drug comprise a polymerase inhibitor, including, but not limited to polymerase II inhibitors such as α-amanitin, and poly(ADP-ribose) polymerase (PARP) inhibitors. Illustrative PARP inhibitors include, but are not limited to Iniparib (BSI 201), Talazoparib (BMN-673), Olaparib (AZD-2281), Olaparib, Rucaparib (AG014699, PF-01367338), Veliparib (ABT-888), CEP 9722, MK 4827, BGB-290, 3-aminobenzamide, and the like.

In certain embodiments the drug comprises a vinca alkyloid. Vinca alkyloids are also anti-tubulin agents. Exemplary vinca alkyloids include, but are not limited to, vincristine, vinblastine, vindesine, and vinorelbine.

The foregoing drugs are illustrative and not limiting. In various embodiments other anti-cancer drugs can be utilized including but not limited to anti-cancer antibodies (e.g., HERCEPTIN®), antimetabolites, alkylating agents, topoisomerase inhibitors, microtubule targeting agents, kinase inhibitors, protein synthesis inhibitors, somatostatin analogs, glucocorticoids, aromatose inhibitors, mTOR inhibitors, protein Kinase B (PKB) inhibitors, phosphatidylinositol, 3-Kinase (PI3K) Inhibitors, cyclin dependent kinase inhibitors, anti-TRAIL molecules, MEK inhibitors, and the like. In certain embodiments the anti-cancer compounds include, but are not limited to flourouracil (5-FU), capecitabine/XELODA, 5-Trifluoromethyl-2'-deoxyuridine, methotrexate sodium, raltitrexed/Tomudex, pemetrexed/Alimta®, cytosine Arabinoside (Cytarabine, Ara-C)/Thioguanine, 6-mercaptopurine (Mercaptopurine, 6-MP), azathioprine/Azasan, 6-thioguanine (6-TG)/Purinethol (TEVA), pentostatin/Nipent, fludarabine phosphate/Fludara® cladribine (2-CdA, 2-chlorodeoxyadenosine)/Leustatin, floxuridine (5-fluoro-2)/FUDR (Hospira, Inc.), ribonucleotide Reductase Inhibitor (RNR), cyclophosphamide/Cytoxan (BMS), neosar, ifosfamide/Mitoxana, thiotepa, BCNU 1,3-bis(2-chloroethyl)-1-nitosourea, 1,-(2-chloroethyl)-3-cyclohexyl-lnitrosourea, methyl CCNU, hexamethylmelamine, busulfan/Myleran, procarbazine HCL/Matulane, dacarbazine (DTIC), chlorambucil/Leukaran®, melphalan/Alkeran, cisplatin (Cisplatinum, CDDP)/Platinol, carboplatin/Paraplatin, oxaliplatin/Eloxitan, bendamustine, carmustine, chloromethine, dacarbazine (DTIC), fotemustine, lomustine, mannosulfan, nedaplatin, nimustine, prednimustine, ranimustine, satraplatin, semustine, streptozocin, temozolomide, treosulfan, triaziquone, triethylene melamine, thioTEPA, triplatin tetranitrate, trofosfamide, uramustine, doxorubicin HCL/Doxil, daunorubicin citrate/Daunoxome mitoxantrone HCL/Novantrone, actinomycin D, etoposide/Vepesid, topotecan HCL/Hycamtin, teniposide (VM-26), irinotecan HCL(CPT-11)/, Camptosar®, camptothecin, Belotecan, rubitecan, vincristine, vinblastine sulfate, vinorelbine tartrate, vindesine sulphate, paclitaxel/Taxol, docetaxel/Taxotere, nanoparticle paclitaxel, abraxane, ixabepilone, larotaxel, ortataxel, tesetaxel, vinflunine, and the like. In certain embodiments the anti-cancer drug(s) comprise one or more drugs selected from the group consisting of carboplatin (e.g., PARAPLATIN®), Cisplatin (e.g., PLATINOL®, PLATINOL-AQ®), Cyclophosphamide (e.g., CYTOXAN®, NEOSAR®), Docetaxel (e.g., TAXOTERE®), Doxorubicin (e.g., ADRIAMYCIN®), Erlotinib (e.g., TARCEVA®), Etoposide (e.g., VEPESID®), Fluorouracil (e.g., 5-FU®), Gemcitabine (e.g., GEMZAR®), imatinib mesylate (e.g., GLEEVEC®), Irinotecan (e.g., CAMPTOSAR®), Methotrexate (e.g., FOLEX®, MEXATE®, AMETHOPTERIN®), Paclitaxel (e.g., TAXOL®, ABRAXANE®), Sorafinib (e.g., NEXAVAR®), Sunitinib (e.g., SUTENT®), Topotecan (e.g., HYCAMTIN®), Vinblastine (e.g., VELBAN®), Vincristine (e.g., ONCOVIN®, VINCASAR PFS®). In certain embodiments the anti-cancer drug comprises one or more drugs selected from the group consisting of retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol. In certain embodiments the anti-cancer compound is selected from the group consisting of abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, zoledronic acid, vinblastine, etc.), an antisense molecule, an SiRNA, and the like.

In certain embodiments the cytotoxic/cytostatic agent comprises a protein or peptide toxin or fragment thereof. Enzymatically active toxins and fragments thereof are exemplified by diphtheria toxin A fragment, nonbinding active fragments of diphtheria toxin, exotoxin A (from *Pseudomo-*

*nas aeruginosa*), ricin A chain, abrin A chain, modeccin A chain, α-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, enomycin, and the tricothecenes, for example.

In certain embodiments the cytotoxins can include, but are not limited to *Pseudomonas* exotoxins, *Diphtheria* toxins, ricin, abrin and derivatives thereof. *Pseudomonas* exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2, which inactivates the protein and causes cell death. The function of domain Ib (amino acids 365-399) remains undefined, although a large part of it, amino acids 365-380, can be deleted without loss of cytotoxicity. See Siegall et al. (1989) *J. Biol. Chem.* 264: 14256-14261.

In certain embodiments the antibody is attached to a preferred molecule in which domain Ia (amino acids 1 through 252) is deleted and amino acids 365 to 380 have been deleted from domain Ib. In certain embodiments all of domain Ib and a portion of domain II (amino acids 350 to 394) can be deleted, particularly if the deleted sequences are replaced with a linking peptide.

In addition, the PE and other cytotoxic proteins can be further modified using site-directed mutagenesis or other techniques known in the art, to alter the molecule for a particular desired application. For example, means to alter the PE molecule in a manner that does not substantially affect the functional advantages provided by the PE molecules described here can also be used and such resulting molecules are intended to be covered herein.

Methods of cloning genes encoding PE fused to various ligands are well known to those of skill in the art (see, e.g., Siegall et al. (1989) *FASEB J.*, 3: 2647-2652; and Chaudhary et al. (1987) *Proc. Natl. Acad. Sci. USA*, 84: 4538-4542).

Like PE, diphtheria toxin (DT) kills cells by ADP-ribosylating elongation factor 2 thereby inhibiting protein synthesis. Diphtheria toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al. (1972) *Science,* 175: 901-903; Uchida et al. (1973) *J. Biol. Chem.*, 248: 3838-3844).

In certain embodiments, the antibody-*Diphtheria* toxin immunoconjugates of have the native receptor-binding domain removed by truncation of the *Diphtheria* toxin B chain. One illustrative modified *Dipththeria* toxin is DT388, a DT in which the carboxyl terminal sequence beginning at residue 389 is removed (see, e.g., Chaudhary et al. (1991) *Bioch. Biophys. Res. Comm.*, 180: 545-551). Like the PE chimeric cytotoxins, the DT molecules can be chemically conjugated to the anti-ALPP antibody, but, in certain preferred embodiments, the antibody will be fused to the *Diphtheria* toxin by recombinant means (see, e.g., Williams et al. (1990) *J. Biol. Chem.* 265: 11885-11889).

Immunomodulators

In certain embodiments the anti-ALPP/ALPPL2 antibodies are attached to an immunomodulatory and function to localize the immunomodulatory at the cancer cell/tumor site. Numerous immunomodulators that can activate an immune response are known to those of skill in the art. In one illustrative, but non-limiting embodiment the immunomodulatory comprise an anti-CD3 antibody. Anti-CD3 monoclonal antibodies induce the proliferation of human T-cells cells in vitro and activate specific and nonspecific cytolysis by human T-cell clones and human peripheral blood lymphocytes. In vivo administration of anti-CD3 prevents tumor growth of a UV-induced mouse fibro sarcoma.

In certain embodiments the immunomodulators comprise agents that blockade immune checkpoints. Immune checkpoints refer to a plethora of inhibitory pathways hardwired into the immune system that are crucial for maintaining self-tolerance and modulating the duration and amplitude of physiological immune responses in peripheral tissues in order to minimize collateral tissue damage. It is now clear that tumours co-opt certain immune-checkpoint pathways as a major mechanism of immune resistance, particularly against T cells that are specific for tumor antigens. Because many of the immune checkpoints are initiated by ligand-receptor interactions, they can be readily blocked by antibodies or modulated by recombinant forms of ligands or receptors.

Cytotoxic T-lymphocyte-associated antigen 4 (CTLA4) antibodies were the first of this class of immunotherapeutics to achieve US Food and Drug Administration (FDA) approval. The first such drug to receive approval, ipilimumab (Yervoy®), for the treatment of advanced melanoma, blocks the activity of a checkpoint protein known as CTLA4, which is expressed on the surface of activated immune cells called cytotoxic T lymphocytes. CTLA4 acts as a "switch" to inactivate these T cells, thereby reducing the strength of immune responses; ipilimumab binds to CTLA4 and prevents it from sending its inhibitory signal. Two other FDA-approved checkpoint inhibitors, nivolumab (Opdivo®) and pembrolizumab (Keytruda®), work in a similar way, but they target a different checkpoint protein on activated T cells known as PD-1. Nivolumab is approved to treat some patients with advanced melanoma or advanced lung cancer, and pembrolizumab is approved to treat some patients with advanced melanoma.

Accordingly in certain embodiments the immunomodulators comprise antibodies directed against CTLA4 (e.g., ipilimumab), and/or antibodies directed against PD-L1 (e.g., nivolumab, pembrolizumab), and/or antibodies directed against PD-L2.

Other examples of immune modulators that can be attached to the anti-ALPP/ALPPL2 antibody include, but are not limited to, gancyclovier, etanercept, tacrolimus, sirolimus, voclosporin, cyclosporine, rapamycin, cyclophosphamide, azathioprine, mycophenolgate mofetil, methotrextrate, glucocorticoid and its analogs, cytokines, xanthines, stem cell growth factors, lymphotoxins, tumor necrosis factor (TNF), hematopoietic factors, interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GM-CSF)), interferons (e.g., interferons-alpha, interferon-beta, interferon-gamma), the stem cell growth factor designated "S 1 factor," erythropoietin and thrombopoietin, or a combination thereof.

Useful immunomodulatory agents also include anti-hormones that block hormone action on tumors and immunosuppressive agents that suppress cytokine production, down-regulate self-antigen expression, or mask MHC antigens. Representative anti-hormones include anti-estrogens including, for example, tamoxifen, raloxifene, aromatase inhibiting 4(5)-imidazoles, 4-hydroxytamoxifen, trioxifene, keoxifene, LY 117018, onapnstone, and toremifene; and anti-androgens such as flutamide, nilutamide, bicalutamide, leuprolide, and goserelin; and anti-adrenal agents. Illustrative immunosuppressive agents include, but are not limited to 2-amino-6-aryl-5-substituted pyrimidines, azathioprine, cyclophosphamide, bromocryptine, danazol, dapsone, glutaraldehyde, anti-idiotypic antibodies for MHC antigens and MHC fragments, cyclosporin A, steroids such as glucocorticosteroids, cytokine or cytokine receptor antagonists (e.g., anti-interferon antibodies, anti-IL10 antibodies, anti-TNFα antibodies, anti-IL2 antibodies), streptokinase, TGFβ, rapamycin, T-cell receptor, T-cell receptor fragments, and T cell receptor antibodies.

Viral Particles.

In certain embodiments, the effector comprises a viral particle (e.g., a filamentous phage, an adeno-associated virus (AAV), a lentivirus, and the like). The antibody can be conjugated to the viral particle and/or can be expressed on the surface of the viral particle (e.g. a filamentous phage). The viral particle can additionally include a nucleic acid that is to be delivered to the target (e.g., a cancer cell that expresses ALPPL2) cell. The use of viral particles to deliver nucleic acids to cells is described in detail in WO 99/55720, U.S. Pat. Nos. 6,670,188, 6,642,051, and 6,669,936.

Antibodies.

In certain embodiments the effector comprises another antibody (e.g., a second) antibody. Attachment of an antibody effector to an anti-ALPPL2 antibody described herein can provide a bi-specific antibody. In certain embodiments the antibody effector comprises an antibody that binds a different epitope of ALPPL2 (than that bound by the anti-ALPPL2 antibody), or a different target on a cell that expresses ALPPL2. Thus, in certain embodiments the effector comprises an antibody that binds a marker expressed on the surface of a cancer cell such as a mesothelioma cell, a testicular cancer cell, an endometrial cancer cell, and certain pancreatic cancer, ovarian cancer and non-small cell lung cancer cells.

In certain embodiments the effector antibody binds to a moiety other than a marker on a cancer cell. For example, in certain embodiments the effector can be an antibody that binds CD3 (e.g., an anti-CD3 antibody). Anti-CD3 monoclonal antibodies induce the proliferation of human T-cells cells in vitro and activate specific and nonspecific cytolysis by human T-cell clones and human peripheral blood lymphocytes. In vivo administration of anti-CD3 prevents tumor growth of a UV-induced mouse fibro sarcoma. Thus, the anti-CD3 antibody effector can be used to enhance an immune response against the anti-ALPL2 targeted cell.

Other illustrative, but non-limiting effector antibodies include, antibodies directed against FcγRI (CD64), which is notably expressed on monocytes and macrophages and upregulated upon activation on neutrophils, antibodies directed against EpCAM (CD326), and the like.

The foregoing bispecific antibodies are illustrative and non-limiting and it will be recognized that essentially any antibody can be coupled to the anti-ALPP/ALPPL2 antibodies described herein depending on the desired application.

B) Attachment of the Antibody to the Effector.

One of skill will appreciate that the anti-ALPP/ALPPL2 antibodies described herein (e.g., M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF) and the effector molecule(s) can be joined together in any order. Thus, where antibody is a single chain polypeptide, the effector molecule can be joined to either the amino or carboxy termini of the targeting molecule. Where the antibody comprises more than one amino acid chain, the effector molecule can be joined to either the amino or carboxyl terminal of any peptide comprising the antibody. The antibody can also be joined to an internal region of the effector molecule, or conversely, the effector molecule can be joined to an internal location of the antibody, as long as the attachment does not interfere with the respective activities of the molecules.

The antibody and the effector can be attached by any of a number of means well known to those of skill in the art. Typically the effector is conjugated, either directly or through a linker (spacer), to the antibody. However, in certain embodiments, where the effector is or comprises a polypeptide it is possible to recombinantly express the chimeric molecule as a single-chain fusion of the effector to a single chain antibody, or as a fusion of the effector to one chain of an antibody comprising more than one chain.

Conjugation of the Effector Molecule to the Antibody.

In certain embodiments, the anti-ALPP/ALPPL2 antibodies described herein (e.g., M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF) can be chemically conjugated to the effector molecule (e.g., a cytotoxin, a label, a ligand, a drug, a liposome, etc.). Means of chemically conjugating molecules are well known to those of skill.

The procedure for attaching an effector to an antibody will vary according to the chemical structure of the effector and/or antibody. Polypeptides typically contain variety of functional groups; e.g., carboxylic acid (COOH) or free amine ($-NH_2$) groups, that are available for reaction with a suitable functional group on an effector molecule to bind the effector thereto.

Alternatively, the antibody and/or the effector can be derivatized to expose or attach additional reactive functional groups. The derivatization can involve attachment of any of a number of linker molecules such as those available from Pierce Chemical Company, Rockford Ill.

A "linker", as used herein, is a molecule that is used to join the targeting molecule to the effector molecule. The linker is capable of forming covalent bonds to both the targeting molecule and to the effector molecule. Suitable linkers are well known to those of skill in the art and include, but are not limited to, straight or branched-chain carbon linkers, heterocyclic carbon linkers, or peptide linkers. Where the targeting molecule and the effector molecule are polypeptides, the linkers may be joined to the constituent amino acids through their side groups (e.g., through a disulfide linkage to cysteine). However, in a preferred embodiment, the linkers will be joined to the alpha carbon amino or carboxyl groups of the terminal amino acids.

The immunoconjugates can be made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. (1987) Science 238: 1098. Carbon-14-labeled 1-isothiocyanatobenzyl-3-methyldiethylene triaminepentaacetic acid (MX-DTPA) is an illustrative, but non-limiting, chelating agent for conjugation of, e.g., a radionucleotide to the antibody (see, e.g., WO1994/011026 (PCT/US1993/010953)).

In certain embodiments conjugation of effectors (e.g., drugs, liposomes, etc.). or linkers attached to effectors, to an antibody takes place at solvent accessible reactive amino acids such as lysines or cysteines that can be derived from the reduction of inter-chain disulfide bonds in the antibody. In certain embodiments cysteine conjugation can occur after reduction of four inter-chain disulfide bonds.

In certain embodiments site-specific conjugation, in which a known number of linker-drugs are consistently conjugated to defined sites in the antibody can be performed to produce a highly homogenous construct. Drug-to-antibody ratio (DAR) can precisely controlled and can be tailored to various linker-drugs, producing, for example, either 2- or 4-DAR site-specific ADCs.

A number of methods are known to achieve sites-specific conjugation. For example, the amino acid cysteine contains a reactive thiol group that serves essential roles in the structure and function of many proteins. Conjugation of thio-reactive probes to proteins through cysteine residues has long been a method for protein labeling, and it has also been applied to the generation of antibody drug conjugates (ADCs). In certain illustrative, but non-limiting embodiments, this process involves partial reduction of existing disulfide bonds (e.g., interchain disulfide bonds).

In certain embodiments to maintain disulfide bonds, cysteine residues can be engineered into proteins. The success of using introduced cysteine residues for site-specific conjugation relies on the ability to select proper sites in which cysteine-substitution does not alter protein structure or function. To accomplish this, the Phage Elisa for Selection of Reactive Thiols (PHESELECTOR) was developed by introducing reactive cysteine residues into an antibody-Fab (trastuzumab-Fab 4D5) at various sites, displaying the Fab on phage, and screening to identify reactive cysteines that do not interfere with antigen binding (see, e.g., Junutula et al. (2008) J. Immunol. Meth. 332: 41-52).

The PHESELECTOR approach has been demonstrated to be efficient and specific, especially compared with conventional cysteine conjugation. It has been demonstrated that the optimal sites for cysteine found using, e.g., an antibody fragment (e.g., Fab) and the PHESELECTOR method can also be applied to full-length antibodies, and data indicate that these sites work well for site-specific conjugation to other mAbs (see, e.g., Boswell et al. (2011) Bioconjug. Chem. 22: 1994-2004; Boswell et al. (2012) Soc. Nuclear Med. 53: 1454-1461; Shen et al. (2012) Nat. Biotechnol. 30:184-189).

Another illustrative, but non-limiting strategy for site-specific conjugation centers on the insertion of amino acids with bio-orthogonal reactive handles such as the amino acid selenocysteine and the unnatural amino acid, acetylphenylalanine (pAcPhe). Two methods have been developed to employ these amino acids and both utilize stop codons. However, one method incorporates selenocysteine (Sec) by pairing the opal stop codon, UGA, with a Sec insertion sequence and the other method incorporates acetylphenylalanine at the amber stop codon, UAG, using a tRNA/aminoacyltRNA synthetase pair. Selenocysteine, employed by the first method, is very similar to the amino acid, cysteine, but contains a selenium atom in place of the sulfur atom. The selenolate group is a more reactive nucleophile than the thiolate counterpart, rendering it amenable to conjugation with electrophilic compounds under conditions in which selenocysteine is selectively activated. There are approximately 25 known selenium-containing proteins in mammals, including proteins such as glutathione peroxidases and thioreductases (Kryukov et al. 92003) Science, 300: 1439-1443). Under normal conditions, UGA codes for transcriptional termination; however, in the presence of a Sec insertion sequence (SECIS) located in the 3' UTR of Sec containing proteins, termination is prevented by the formation of an mRNA secondary structure and Sec is inserted at the UGA codon (Caban and Copeland (2006) Cell Mol. Life Sci. 63: 73-81). Sec insertion can be engineered into non-Sec coding genes by insertion of the UGA codon and a SECIS at the 3' end of the gene. This technique has been used, inter alia, in the Sec labeling and subsequent site-specific conjugation of mAbs (see, e.g., Hofer et al. (2009) Biochem. 48: 12047-12057).

Still another illustrative method for site-specific conjugation utilizes the unnatural amino acid, p-acetylphenylalanine (pAcPhe). pAcPhe contains a keto group that can be selectively conjugated to a drug containing an alkoxy-amine through an oxime ligation. To incorporate pAcPhe into an antibody, the amber stop codon is substituted into the antibody at the desired location. The antibody cDNA is then co-expressed with an amber suppressor tRNA and the properly paired mutant tRNA sythetase. The tRNA sythetase loads pAcPhe onto the amber tRNA and thus pAcPhe is incorporated into the antibody at the amber site UAG (see, e.g., Liu et al. 92007) Nat. Meth. 4: 239-244; Wang et al. (2003) Proc. Natl. Acad. Sci. USA, 100: 56-61; Axup (2012) Proc. Natl. Acad. Sci. USA, 109: 16101-16116).

In addition to pAcPhe, other unnatural amino acids can be exploited for use in site-specific conjugation using similar processes involving matching tRNA/aminoacyltRNA synthetase pairs (see, e.g., Young (2002) J. Mol. Biol. 395: 361-374; Kiick et al. (2002) Proc. Natl. Acad. Sci. USA, 99: 19-24).

In various embodiments the use of enzymes to catalyze bond formation can be exploited for use in site-specific conjugation. For example, the glycotransferase platform uses a mutant glycotransferase to attach a chemically active sugar moiety to a glycosylation site on an antibody. Molecules of choice can then be conjugated to the chemical handle on the sugar moiety. In another illustrative, but non-limiting approach transglutaminase is used to form a bond between an amine group on the linker/drug and an engineered glutamine residue on the antibody.

Glycotransferases are a large family of proteins involved in the synthesis of oligosaccharides and are responsible for the transfer of a sugar residue from an activated sugar nucleotide to a sugar acceptor or glycoprotein/lipid. The structures of several glycotransferases are known and reveal that sugar donor specificity is determined by a few amino acids in the catalytic pocket (Qasba et al. (2005) *Trends Biochem. Sci.* 30: 53-62), Using this knowledge, residues have been mutated in the pocket of the glycotransferase, e.g., B4Gal-T1, to broaden donor specificity and allow the transfer of the chemically reactive sugar residue, 2-keto-Gal (see, e.g., Ramakrishnan et al. (2002) *J. Biol. Chem.* 277: 20833-20839). This technology allows for the ability to transfer a chemically reactive sugar to any lipid or protein containing a glycosylation site. Human IgG antibodies contain an N-glycosylation site at the conserved Asn-297 of the Fc fragment. The glycans attached to this site are generally complex, but can be degalactosylated down to G0, onto which a mutant glycotransferase is capable of transferring C2-keto-Gal with high efficiency (see, e.g., Boeggeman et al. (2009) *Bioconjug. Chem.* 20: 1228-1236). The active chemical handle of C2-keto Gal can then be coupled to biomolecules with an orthogonal reactive group. This approach has been used successfully for the site-specific conjugation of the anti-Her2 antibody, trastuzumab, with Alexa Fluor 488 aminooxyacetamide and is a viable technique for site specific ADC generation (Id.).

The second platform utilizes transglutaminase to catalyze the formation of a covalent bond between a free amine group and a glutamine side chain. Transglutaminase from *Streptoverticillium mobaraense* (mTG) is commercially available and has been used extensively as a protein crosslinking agent (see, e.g., Yokoyama et al. (2004) ALPP. *Microbiol. Biotechnol.* 64: 447-454). mTG does not recognize any of the natural occurring glutamine residues in the Fc region of glycosylated antibodies, but does recognize a "glutamine tag" that can be engineered into an antibody (see, e.g., Jeger et al. (2010) *Angew Chem. Int. Ed. Engl.* 49: 9995-9997). By way of illustration, the glutamine tag, LLQG, has been engineered into different sites in the constant domain of an antibody targeting the epidermal growth factor receptor. mTG was then used to conjugate these sites with fluorophores or monomethyl dolastatin 10 (MMAD) and several sites where found to have good biophysical properties and a high degree of conjugation. mTG was also able to conjugate to glutamine tags on anti-Her2 and anti-M1S1 antibodies. An antiM1S1-vc-MMAD conjugate displayed strong in vitro and in vivo activity, suggesting that conjugation using this method does not alter antibody binding or affinity and demonstrates the utility of this approach in the site-specific conjugation of ADCs (see, e.g., Strop et al. (2013) *Chem. Biol.* 20: 161-167).

In addition to glycotransferases and transglutaminases, other enzymes have been explored for use in protein labeling (Sunbul and Yin (2009) *Org. Biomol. Chem.* 7: 3361-3371). One such enzyme, formylglycine generating enzyme, recognizes the sequence CxPxR and oxidizes a cysteine residue to form formylglycine, thus generating a protein with an aldehyde tag. The aldehyde group can then be conjugated to molecule of choice through, e.g., hydrozino-Pictet-Spengler chemistry.

Many other procedures and linker molecules for attachment of various compounds including radionuclide metal chelates, toxins and drugs to proteins such as antibodies are known (see, e.g., European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071-4075). In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine*, Academic Press, pp. 168-190 (1982), Waldmann (1991) *Science,* 252: 1657, U.S. Pat. Nos. 4,545,985 and 4,894,443.

In some circumstances, it is desirable to free the effector from the antibody when the immunoconjugate has reached its target site. Therefore, immunoconjugates comprising linkages that are cleavable in the vicinity of the target site may be used when the effector is to be released at the target site. Cleaving of the linkage to release the agent from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225, and 4,625,014. Illustrative cleavable linkers include, but are not limited to, acid-labile linkers, protease cleavable linkers, disulfide linkers, and the like. Acid-labile linkers are designed to be stable at pH levels encountered in the blood, but become unstable and degrade when the low pH environment in lysosomes is encountered. Protease-cleavable linkers are also designed to be stable in blood/plasma, but rapidly release free drug inside lysosomes in cancer cells upon cleavage by lysosomal enzymes. They take advantage of the high levels of protease activity inside lysosomes and typically include a peptide sequence that is recognized and cleaved by these proteases, e.g., as occurs with a dipeptide Val-Cit linkage that is rapidly hydrolyzed by cathepsins. Disulfide linkers exploit the high level of intracellular reduced glutathione to release free drug inside the cell.

Thus, in various embodiments the linker can be stable (non-cleavable) or hydrolysable (cleavable), whereby it is released following cellular entry. The major mechanisms by which the drug is cleaved from the antibody include hydrolysis in the acidic pH of the lysosomes (hydrazones, acetals, and cis-aconitate-like amides), peptide cleavage by lysosomal enzymes (the cathepsins and other lysosomal enzymes), and reduction of disulfides. As a result of these varying mechanisms for cleavage, mechanisms of linking the drug to the antibody also vary widely and any suitable linker can be used.

An example of a suitable conjugation procedure relies on the conjugation of hydrazides and other nucleophiles to the aldehydes generated by oxidation of the carbohydrates that naturally occur on antibodies. Hydrazone-containing conjugates can be made with introduced carbonyl groups that provide the desired drug-release properties. Conjugates can also be made with a linker that has a disulfide at one end, an alkyl chain in the middle, and a hydrazine derivative at the other end. The anthracyclines are one example of cytotoxins that can be conjugated to antibodies using this technology.

Linkers containing functional groups other than hydrazones have the potential to be cleaved in the acidic milieu of the lysosomes. For example, conjugates can be made from thiol-reactive linkers that contain a site other than a hydrazone that is cleavable intracellularly, such as esters, amides, and acetals/ketals. Camptothecin is one cytotoxic agent that can be conjugated using these linkers. Ketals made from a 5 to 7-member ring ketone and that has one of the oxygens attached to the cytotoxic agent and the other to a linker for antibody attachment also can be used. The anthracyclines are also an example of a suitable cytotoxin for use with these linkers.

Another example of a class of pH sensitive linkers are the cis-aconitates, which have a carboxylic acid juxtaposed to an amide bond. The carboxylic acid accelerates amide hydrolysis in the acidic lysosomes. Linkers that achieve a similar type of hydrolysis rate acceleration with several other types of structures can also be used. The maytansinoids are an example of a cytotoxin that can be conjugated with linkers attached at C-9.

Another potential release method for drug conjugates is the enzymatic hydrolysis of peptides by the lysosomal enzymes. In one example, a peptide is attached via an amide bond to para-aminobenzyl alcohol and then a carbamate or carbonate is made between the benzyl alcohol and the cytotoxic agent. Cleavage of the peptide leads to the collapse, or self-immolation, of the aminobenzyl carbamate or carbonate. The cytotoxic agents exemplified with this strategy include anthracyclines, taxanes, mitomycin C, and the auristatins. In one example, a phenol can also be released by collapse of the linker instead of the carbamate. In another variation, disulfide reduction is used to initiate the collapse of a para-mercaptobenzyl carbamate or carbonate.

In certain embodiments cytotoxic agents conjugated to antibodies have little, if any, solubility in water and that can limit drug loading on the conjugate due to aggregation of the conjugate. One approach to overcoming this is to add solublizing groups to the linker. Conjugates made with a linker consisting of PEG and a dipeptide can been used, including those having a PEG di-acid, thiol-acid, or maleimide-acid attached to the antibody, a dipeptide spacer, and an amide bond to the amine of an anthracycline or a duocarmycin analogue. Another example is a conjugate prepared with a PEG-containing linker disulfide bonded to a cytotoxic agent and amide bonded to an antibody. Approaches that incorporate PEG groups can be beneficial in overcoming aggregation and limits in drug loading.

In certain embodiments linkers for the preparation of the antibody-drug conjugates described herein include, but are not limited to, linkers having the formula:

(CO-Alk$^1$-Sp$^1$-Ar-Sp$^2$-Alk$^2$-C(Z$^1$=Q-Sp)

where Alk$^1$ and Alk$^2$ are independently a bond or branched or unbranched $(C_1-C_{10})$ alkylene chain; Sp$^1$ is a bond, —S—, —CONH—, —NHCO—, —NR—, —N(CH$_2$CH$_2$)$_2$N—, or —X—Ar'—Y—(CH$_2$)$_n$—Z wherein X, Y, and Z are independently a bond, —NR'—, —S—, or —O—, with the proviso that when n=0, then at least one of Y and Z must be a bond and Ar' is 1,2-, 1,3-, or 1,4-phenylene optionally substituted with one, two, or three groups of $(C_1-C_5)$ alkyl, $(C_1-C_4)$ alkoxy, $(C_1-C_4)$ thioalkoxy, halogen, nitro, —COOR', —CONHR', —(CH$_2$)$_n$COOR', —S(CH$_2$)$_n$COOR', —O(CH$_2$)$_n$CONHR', or —S(CH$_2$)$_n$CONHR', with the proviso that when Alk' is a bond, Sp$_1$ is a bond; n is an integer from 0 to 5; R' is a branched or unbranched $(C_1-C_5)$ chain optionally substituted by one or two groups of —OH, $(C_1-C_4)$ alkoxy, $(C_1-C_4)$ thioalkoxy, halogen, nitro, $(C_1-C_3)$ dialkylamino, or $(C_1-C_3)$ trialkylammonium -A$^-$ where A$^-$ is a pharmaceutically acceptable anion completing a salt; Ar is 1,2-, 1,3-, or 1,4-phenylene optionally substituted with one, two, or three groups of $(C_1-C_6)$ alkyl, $(C_1-C_5)$ alkoxy, $(C_1-C_4)$ thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR' where n and R' are as hereinbefore defined or a 1,2-, 1,3-, 1,4-, 1,5-, 1,6-, 1,7-, 1,8-, 2,3-, 2,6-, or 2,7-naphthylidene or

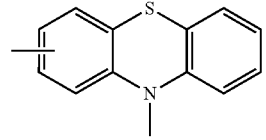

with each naphthylidene or phenothiazine optionally substituted with one, two, three, or four groups of $(C_1-C_6)$ alkyl, $(C_1-C_5)$ alkoxy, $(C_1-C_4)$ thioalkoxy, halogen, nitro, —COOR', —CONHR', —O(CH$_2$)$_n$COOR', —S(CH$_2$)$_n$COOR', or —S(CH$_2$)$_n$CONHR' wherein n and R' are as defined above, with the proviso that when Ar is phenothiazine, Sp$^1$ is a bond only connected to nitrogen; Sp$^2$ is a bond, —S—, or —O—, with the proviso that when Alk$^2$ is a bond, Sp$^2$ is a bond; Z$^1$ is H, $(C_1-C_5)$ alkyl, or phenyl optionally substituted with one, two, or three groups of $(C_1-C_5)$ alkyl, $(C_1-C_5)$ alkoxy, $(C_1-C_4)$ thioalkoxy, halogen, nitro, —COOR', —ONHR', —O(CH$_2$)$_n$COOR', —S(CH$_2$)$_n$COOR', —O(CH$_2$)$_n$CONHR', or —S(CH$_2$)$_n$CONHR' wherein n and R' are as defined above; Sp is a straight or branched-chain divalent or trivalent $(C_1-C_{18})$ radical, divalent or trivalent aryl or heteroaryl radical, divalent or trivalent $(C_3-C_{18})$ cycloalkyl or heterocycloalkyl radical, divalent or trivalent aryl- or heteroaryl-aryl $(C_1-C_{18})$ radical, divalent or trivalent cycloalkyl- or heterocycloalkyl-alkyl $(C_1-C_{18})$ radical or divalent or trivalent $(C_2-C_{18})$ unsaturated alkyl radical, wherein heteroaryl is preferably furyl, thienyl, N-methylpyrrolyl, pyridinyl, N-methylimidazolyl, oxazolyl, pyrimidinyl, quinolyl, isoquinolyl, N-methylcarbazoyl, aminocourmarinyl, or phenazinyl and where if Sp is a trivalent radical, Sp may be additionally substituted by lower $(C_1-C_5)$ dialkylamino, lower $(C_1-C_5)$ alkoxy, hydroxy, or lower $(C_1-C_5)$ alkylthio groups; and Q is =NHNCO—, =NHNCS—, =NHN-CONH—, =NHNCSNH—, or =NHO—.

In certain embodiments Alk$^1$ is a branched or unbranched $(C_1-C_{10})$ alkylene chain; Sp' is a bond, —S—, —CONH—, —NHCO—, or —NR' wherein R' is as hereinbefore defined, with the proviso that when Alk' is a bond, Sp' is a bond;

Ar is 1,2-, 1,3-, or 1,4-phenylene optionally substituted with one, two, or three groups of $(C_1-C_6)$ alkyl, $(C_1-C_5)$ alkoxy, $(C_1-C_4)$ thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR' wherein n and R' are as hereinbefore defined, or Ar is a 1,2-, 1,3-, 1,4-, 1,5-, 1,6-, 1,7-, 1,8-, 2,3-, 2,6-, or 2,7-naphthylidene each optionally substituted with one, two, three, or four groups of $(C_1-C_6)$ alkyl, $(C_1-C_5)$ alkoxy, $(C_1-C_4)$ thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR';

Z$^1$ is $(C_1-C_5)$ alkyl, or phenyl optionally substituted with one, two, or three groups of $(C_1-C_5)$ alkyl, $(C_1-C_4)$ alkoxy, $(C_1-C_4)$ thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR'; Alk$^2$ and Sp$^2$ are together a bond; and Sp and Q are as immediately defined above.

U.S. Pat. No. 5,773,001, incorporated herein by reference for the linkers and linking methods described therein, discloses linkers that can be used with nucleophilic drugs, particularly hydrazides and related nucleophiles, prepared from the calicheamicins. These linkers are especially useful in those cases where better activity is obtained when the linkage formed between the drug and the linker is hydrolysable. These linkers contain two functional groups, including (1) a group for reaction with an antibody (e.g., carboxylic acid), and (2) a carbonyl group (e.g., an aldehyde or a ketone) for reaction with a drug. The carbonyl groups may react with a hydrazide group on the drug to form a hydrazone linkage. This linkage is cleavable hydrolysable, allowing for release of the therapeutic agent from the conjugate after binding to the target cells.

In certain embodiments, N-hydroxysuccinimide (OSu) esters or other comparably activated esters can be used to generate an activated hydrolyzable linker-drug moiety. Examples of other suitable activating esters include, but are not limited to NHS (N-hydroxysuccinimide), sulfo-NHS (sulfonated NHS), PFP (pentafluorophenyl), TFP (tetrafluorophenyl), and DNP (dinitrophenyl).

In certain embodiments the linker is a hydrolysable linker such as a maleimidocaproyl-valine-citrulline-p-aminobenzyloxycarbonyl (MC-vc-PAB-MMAE) or 4-(4-acetylphenoxy)butanoic acid (AcBut). In certain embodiments the linker is a non-hydrolysable linker such as maleimidocaproyl (MC-MMAF). In certain illustrative, but non-limiting embodiments, antibody-drug conjugates can be prepared using, for example, (3-Acetylphenyl)acetic acid (AcPAc) or 4-mercapto-4-methyl-pentanoic acid (Amide) as the linker molecule.

In certain embodiments the linker can be a dipeptide linker, such as a valine-citrulline (val-cit), a phenylalanine-lysine (phe-lys) linker, or maleimidocapronic-valine-citruline-p-aminobenzyloxycarbonyl (vc) linker, a tripeptide linker such as GGG and the like, a tetrapeptide linker such as GGGG (SEQ ID NO:71), a pentapeptide linker such as GGGGS (SEQ ID NO:72), and the like. In certain embodiments, the linker is Sulfosuccinimidyl-4-[N-maleimidomethyl]cyclohexane-1-carboxylate (smcc). Sulfo-smcc conjugation occurs via a maleimide group which reacts with sulfhydryls (thiols, —SH), while its Sulfo-NHS ester is reactive toward primary amines (as found in Lysine and the protein or peptide N-terminus). Further, in certain embodiments, the linker may be maleimidocaproyl (mc).

The foregoing linkers are illustrative and non-limiting. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

Conjugated Encapsulation Systems.

While, in various embodiments the therapeutic agents are chemically conjugated to the antibody, e.g., as described above, in other embodiments, the effector can comprise an encapsulation system, such as a viral capsid, a liposome, or micelle that contains a therapeutic composition such as a drug, a nucleic acid (e.g. an antisense nucleic acid, and RNAi, or another nucleic acid to be delivered to the cell), or another therapeutic moiety that is preferably shielded from direct exposure to the circulatory system. Means of preparing liposomes attached to antibodies are well known to those of skill in the art (see, e.g., U.S. Pat. No. 4,957,735, Connor et al. (1985) *Pharm. Ther.*, 28: 341-365, and the like).

Conjugation of Chelates.

In certain embodiments, the effector comprises a chelate that is attached to an antibody or to an epitope tag. The anti-ALPP/ALPPL2 antibody bears a corresponding epitope tag or antibody so that simple contacting of the antibody to the chelate results in attachment of the antibody with the effector. The combining step can be performed before the moiety is used (targeting strategy) or the target tissue can be bound to the antibody before the chelate is delivered. Methods of producing chelates suitable for coupling to various targeting moieties are well known to those of skill in the art (see, e.g., U.S. Pat. Nos. 6,190,923, 6,187,285, 6,183,721, 6,177,562, 6,159,445, 6,153,775, 6,149,890, 6,143,276, 6,143,274, 6,139,819, 6,132,764, 6,123,923, 6,123,921, 6,120,768, 6,120,751, 6,117,412, 6,106,866, 6,096,290, 6,093,382, 6,090,800, 6,090,408, 6,088,613, 6,077,499, 6,075,010, 6,071,494, 6,071,490, 6,060,040, 6,056,939, 6,051,207, 6,048,979, 6,045,821, 6,045,775, 6,030,840, 6,028,066, 6,022,966, 6,022,523, 6,022,522, 6,017,522, 6,015,897, 6,010,682, 6,010,681, 6,004,533, and 6,001,329).

Representative linkers useful for conjugation of radioisotopes include, but are not limited to, diethylenetriamine pentaacetate (DTPA)-isothiocyanate, succinimidyl 6-hydrazinium nicotinate hydrochloride (SHNH), and hexamethylpropylene amine oxime (HMPAO) (see, e.g., Bakker et al. (1990) *J. Nucl. Med.* 31: 1501-1509, Chattopadhyay et al. (2001) *Nucl. Med. Biol.* 28: 741-744, Dewanjee et al. (1994) *J. Nucl. Med.* 35: 1054-63, Krenning et al. (1989) *Lancet* 1: 242-244, Sagiuchi et al. (2001) *Ann. Nucl. Med.* 15: 267-270); U.S. Pat. No. 6,024,938). Alternatively, in certain embodiments, the antibody may be derivatized so that a radioisotope may be bound directly to it (see, e.g., Yoo et al. (1997) *J. Nucl. Med.* 38: 294-300). Iodination methods are also known in the art, and representative protocols may be found, for example, in Krenning et al. (1989) *Lancet* 1:242-244 and in Bakker et al. (1990) *J. Nucl. Med.* 31:1501-1509.

Production of Fusion Proteins.

Where the antibody and/or the effector is relatively short (e.g., less than about 50 amino acids) they can be synthesized using standard chemical peptide synthesis techniques. Where both molecules are relatively short the chimeric molecule may be synthesized as a single contiguous polypeptide. Alternatively the targeting molecule and the effector molecule may be synthesized separately and then fused by condensation of the amino terminus of one molecule with the carboxyl terminus of the other molecule thereby forming a peptide bond. Alternatively, the targeting and effector molecules can each be condensed with one end of a peptide spacer molecule thereby forming a contiguous fusion protein.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis*; pp. 3-284 in *The Peptides: Analysis, Synthesis, Biology. Vol.* 2: *Special Methods in Peptide Synthesis*, Part A., Merrifield, et al. *J. Am. Chem. Soc.*, 85: 2149-2156 (1963), and Stewart et al., *Solid Phase Peptide Synthesis, 2nd ed.* Pierce Chem. Co., Rockford, Ill. (1984).

In certain embodiments, the chimeric fusion proteins of the present invention are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins of this invention can be prepared by any suitable method, including, for example, cloning and restriction of appropriate sequences, or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.*, 22: 1859-1862; and the solid support method of U.S. Pat. No. 4,458,066.

Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences can be obtained by the ligation of shorter sequences.

Alternatively, in certain embodiments subsequences can be cloned and the appropriate subsequences cleaved using appropriate restriction enzymes. The fragments can then be ligated to produce the desired DNA sequence.

In certain embodiments DNA encoding fusion proteins of the present invention can be cloned using PCR cloning methods.

While the antibody and the effector are, in certain embodiments, essentially joined directly together, one of skill will appreciate that the molecules can be separated by a spacer, e.g., a peptide spacer consisting of one or more amino acids (e.g., (Gly$_4$Ser)$_3$, SEQ ID NO:73). Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

The nucleic acid sequences encoding the fusion proteins can be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes (1982) *Protein Purification*, Springer-Verlag, N.Y.; Deutscher (1990) *Methods in Enzymology Vol. 182: Guide to Protein Purification.*, Academic Press, Inc. N.Y.). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the fusion protein may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (see, e.g., Debinski et al. (1993) *J. Biol. Chem.*, 268: 14065-14070; Kreitman and Pastan (1993) *Bioconjug. Chem.*, 4: 581-585; and Buchner, et al. (1992) *Anal. Biochem.*, 205: 263-270).

One of skill would recognize that modifications can be made to the fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

Pharmaceutical Compositions.

The anti-ALPP/ALPPL2 antibodies described herein (e.g., M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF) and/or immunoconjugates thereof are useful for parenteral, topical, oral, or local administration (e.g. injected into a tumor site), aerosol administration, or transdermal administration, for prophylactic, but principally for therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the antibodies described herein and/or immunoconjugates thereof and pharmaceutical compositions comprising antibodies described herein and/or immunoconjugates thereof, when administered orally, are preferably protected from digestion. This can be accomplished by a number of means known to those of skill in the art, e.g., by complexing the protein with a composition to render it resistant to acidic and enzymatic hydrolysis or by packaging the protein in an appropriately resistant carrier such as a liposome. Means of protecting proteins from digestion are well known in the art.

In various embodiments a composition, e.g., a pharmaceutical composition, containing one or a combination of anti-ALPP/ALPPL2 antibodies, or antigen-binding portion(s) thereof, or immunoconjugates thereof, formulated together with a pharmaceutically acceptable carrier are provided.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, may be coated in a material to protect the compound from the action of acids and other natural conditions that may inactivate the compound.

In certain embodiments the antibody and/or immunoconjugate can be administered in the "native" form or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience, and as described above.

By way of illustration, a pharmaceutically acceptable salt can be prepared for any of the antibodies and/or immunoconjugates described herein having a functionality capable of forming a salt. A pharmaceutically acceptable salt is any salt that retains the activity of the parent compound and does not impart any deleterious or untoward effect on the subject to which it is administered and in the context in which it is administered.

In various embodiments pharmaceutically acceptable salts may be derived from organic or inorganic bases. The salt may be a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

Methods of formulating pharmaceutically active agents as salts, esters, amide, prodrugs, and the like are well known to those of skill in the art. For example, salts can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the active agents herein include halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

For the preparation of salt forms of basic drugs, the pKa of the counterion is preferably at least about 2 pH units lower than the pKa of the drug. Similarly, for the preparation of salt forms of acidic drugs, the pKa of the counterion is preferably at least about 2 pH units higher than the pKa of the drug. This permits the counterion to bring the solution's pH to a level lower than the $pH_{max}$ to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (i.e., break down into the individual entities of drug and counterion) in an aqueous environment.

Preferably, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

Preparation of esters typically involves functionalization of hydroxyl and/or carboxyl groups that are present within the molecular structure of the antibody and/or immunoconjugate. In certain embodiments, the esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

Pharmaceutical compositions comprising the antibodies and/or immunoconjugates described herein can be administered alone or in combination therapy, i.e., combined with other agents. For example, the combination therapy can include a an antibody or immunoconjugate with at least one or more additional therapeutic agents, such as the anticancer agents described infra. The pharmaceutical compositions can also be administered in conjunction with radiation therapy and/or surgery.

A composition comprising the antibodies and/or immunoconjugates described herein can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art (see, e.g., Sustained and Controlled Release Drug Delivery Systems, J. R. Robinson, ed., Marcel Dekker, Inc., New York, 1978).

In certain embodiments administration of an anti-ALPP/ALPPL2 antibody or immunoconjugate may be facilitated by coating the antibody or immunoconjugate composition, or co-administering the antibody or immunoconjugate, a material to prevent its inactivation. For example, the compound may be administered to a subject in an appropriate carrier, for example, liposomes, or a diluent. Pharmaceutically acceptable diluents include, but are not limited to, saline and aqueous buffer solutions. Liposomes include, but are not limited to, water-in-oil-in-water CGF emulsions as well as conventional liposomes (Strej an et al. (1984) *J. Neuroimmunol*, 7: 27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of is contemplated. Supplementary active compounds can also be incorporated into the compositions.

In various embodiments the therapeutic compositions are typically sterile and stable under the conditions of manufacture and storage. The composition(s) can be formulated as a solution, a microemulsion, in a lipid or liposome, or other ordered structure suitable to contain high drug concentration(s). In certain embodiments the carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound (e.g., antibodies and/or immunoconjugates described herein) in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, illustrative methods of preparation include vacuum drying, and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, in certain embodiments, the antibodies and/or immunoconjugates described herein may be administered once or twice daily, or once or twice weekly, or once or twice monthly by subcutaneous injection.

It is especially advantageous to formulate parenteral compositions in unit dosage form for ease of administration and uniformity of dosage. Unit dosage form as used herein refers to physically discrete units suited as unitary dosages for the subjects to be treated. Each unit contains a predetermined quantity of active compound calculated to produce the desired therapeutic effect in association with the required pharmaceutical carrier. The specifications for the unit dosage forms are dictated by and directly dependent on (a) the unique characteristics of the active compound and the particular therapeutic effect to be achieved, and (b) the limitations inherent in the art of compounding such an active compound for the treatment of individuals.

In certain embodiments the formulation comprises a pharmaceutically anti-oxidant. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the antibodies and/or immunoconjugates described herein include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient that can be combined with a carrier material to produce a single dosage form will generally be that amount of the composition which produces a therapeutic effect. Generally, out of one hundred percent, this amount will range from about 0.001 percent to about ninety percent of active ingredient, preferably from about 0.005 percent to about 70 percent, most preferably from about 0.01 percent to about 30 percent.

Formulations of antibodies and/or immunoconjugates described herein that are suitable for vaginal administration also include pessaries, tampons, creams, gels, pastes, foams or spray formulations containing such carriers as are known in the art to be appropriate. Dosage forms for the topical or transdermal administration of antibodies and/or immunoconjugates described herein include powders, sprays, ointments, pastes, creams, lotions, gels, solutions, patches and inhalants. In certain embodiments the active compound may be mixed under sterile conditions with a pharmaceutically acceptable carrier, and with any preservatives, buffers, or propellants that may be required.

The phrases "parenteral administration" and "administered parenterally" as used herein means modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection, and infusion.

Examples of suitable aqueous and nonaqueous carriers that may be employed in the pharmaceutical compositions comprising antibodies and/or immunoconjugates described herein include, but are not limited to water, ethanol, polyols (such as glycerol, propylene glycol, polyethylene glycol, and the like), and suitable mixtures thereof, vegetable oils, such as olive oil, and injectable organic esters, such as ethyl oleate, and the like. Proper fluidity can be maintained, for example, by the use of coating materials, such as lecithin, by the maintenance of the required particle size in the case of dispersions, and by the use of surfactants.

In various embodiments these compositions may also contain adjuvants such as preservatives, wetting agents, emulsifying agents and dispersing agents. Particular examples of adjuvants that are well-known in the art include, for example, inorganic adjuvants (such as aluminum salts, e.g., aluminum phosphate and aluminum hydroxide), organic adjuvants (e.g., squalene), oil-based adjuvants, virosomes (e.g., virosomes that contain a membrane-bound hemagglutinin and neuraminidase derived from the influenza virus).

Prevention of presence of microorganisms in formulations may be ensured both by sterilization procedures, and/or by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

When the antibodies and/or immunoconjugates described herein are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, the antibodies and/or immunoconjugates described herein, that may be used in a suitable hydrated form, and/or the pharmaceutical compositions, are formulated into pharmaceutically acceptable dosage forms by conventional methods known to those of skill in the art.

Actual dosage levels of the active ingredients (e.g., antibodies and/or immunoconjugates described herein) in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of antibodies and/or immunoconjugates described herein will be that amount of the compound which is the lowest dose effective to produce a therapeutic effect. Such an effective dose will generally depend upon the factors described above. In certain embodiments, it is preferred that administration be intravenous, intramuscular, intraperitoneal, or subcutaneous, preferably administered proximal to the site of the target. If desired, the effective daily dose of a therapeutic composition may be administered a single dosage, or as two, three, four, five, six or more sub-doses administered separately at appropriate intervals throughout the day, optionally, in unit dosage forms. While it is possible for antibodies and/or immunoconjugates described herein to be administered alone, it is typically preferable to administer the compound(s) as a pharmaceutical formulation (composition).

In certain embodiments the therapeutic compositions can be administered with medical devices known in the art. For example, in a illustrative embodiment, antibodies and/or immunoconjugates described herein can be administered with a needleless hypodermic injection device, such as the devices disclosed in U.S. Pat. No. 5,399,163, 5,383,851, 5,312,335, 5,064,413, 4,941,880, 4,790,824, or 4,596,556. Examples of useful well-known implants and modules are described for example in U.S. Pat. No. 4,487,603, which discloses an implantable micro-infusion pump for dispensing medication at a controlled rate, in U.S. Pat. No. 4,486,194, which discloses a therapeutic device for administering medications through the skin, in U.S. Pat. No. 4,447,233, which discloses a medication infusion pump for delivering medication at a precise infusion rate, in U.S. Pat. No. 4,447,224, which discloses a variable flow implantable infusion apparatus for continuous drug delivery, in U.S. Pat. No. 4,439,196, which discloses an osmotic drug delivery system having multi-chamber compartments, and in U.S. Pat. No. 4,475,196, which discloses an osmotic drug delivery system. Many other such implants, delivery systems, and modules are known to those skilled in the art.

In certain embodiments, the anti-ALPP/ALPPL2 antibodies and/or immunoconjugates described herein can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade (1989) *J. Clin. Pharmacol.* 29: 685). Illustrative targeting moieties include, but are not limited to folate or biotin (see, e.g., U.S. Pat. No. 5,416,016); mannosides (Umezawa et al., (1988) *Biochem. Biophys. Res. Commun.* 153: 1038); antibodies (Bloeman et al. (1995) *FEBS Lett.* 357:140; Owais et al. (1995) *Antimicrob. Agents Chemother.* 39:180); surfactant protein A receptor (Briscoe et al. (1995) *Am. J. Physiol.* 1233:134).

Kits.

Where a radioactive, or other, effector is used as a diagnostic and/or therapeutic agent, it is frequently impossible to put the ready-for-use composition at the disposal of the user, because of the often poor shelf life of the radiolabeled compound and/or the short half-life of the radionuclide used. In such cases the user can carry out the labeling reaction with the radionuclide in the clinical hospital, physician's office, or laboratory. For this purpose, or other purposes, the various reaction ingredients can then be offered to the user in the form of a so-called "kit". The kit is preferably designed so that the manipulations necessary to perform the desired reaction should be as simple as possible to enable the user to prepare from the kit the desired composition by using the facilities that are at his disposal. Therefore the invention also relates to a kit for preparing a composition according to this invention.

In certain embodiments, such a kit comprises one or more antibodies or immunoconjugates described herein. The antibodies or immunoconjugates can be provided, if desired, with inert pharmaceutically acceptable carrier and/or formulating agents and/or adjuvants is/are added. In addition, the kit optionally includes a solution of a salt or chelate of a suitable radionuclide (or other active agent), and (iii) instructions for use with a prescription for administering and/or reacting the ingredients present in the kit.

The kit to be supplied to the user may also comprise the ingredient(s) defined above, together with instructions for use, whereas the solution of a salt or chelate of the radionuclide, defined sub (ii) above, which solution has a limited shelf life, may be put to the disposal of the user separately.

The kit can optionally, additionally comprise a reducing agent and/or, if desired, a chelator, and/or instructions for use of the composition and/or a prescription for reacting the ingredients of the kit to form the desired product(s). If desired, the ingredients of the kit may be combined, provided they are compatible.

In certain embodiments, the immunoconjugate can simply be produced by combining the components in a neutral medium and causing them to react. For that purpose the effector may be presented to the antibody, for example, in the form of a chelate.

When kit constituent(s) are used as component(s) for pharmaceutical administration (e.g. as an injection liquid) they are preferably sterile. When the constituent(s) are provided in a dry state, the user should preferably use a sterile physiological saline solution as a solvent. If desired, the constituent(s) may be stabilized in the conventional manner with suitable stabilizers, for example, ascorbic acid, gentisic acid or salts of these acids, or they may comprise other auxiliary agents, for example, fillers, such as glucose, lactose, mannitol, and the like.

While the instructional materials, when present, typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

Chimeric Antigen Receptor (CAR) Constructs and Therapy.

In certain embodiments, the antibodies described herein can be utilized in the creation of constructs/cells for CAR-T cell therapy. CAR-T cell therapy is a cellular immunotherapy that involves administration to a mammal having cancer (e.g., a cancer patient) genetically engineered cells (e.g., T cells, a natural killer (NK) cells, a cytotoxic T lymphocytes (CTLs), regulatory T cells, and the like) that express a chimeric antigen receptor (CAR) and that that act on tumor cells (that interact with the CAR) and cause apoptosis of the tumor cells.

Typically, the genetically engineered cells are prepared by expressing on a cell (e.g., a T cell) a CAR having variable regions of an antibody (VL and VH) combined with a CD3 chain (intracellular domain) using gene transfer technique. CAR is a general term for a chimeric protein in which a light chain (VL) and a heavy chain (VH) of a variable region of a monoclonal antibody specific for a tumor antigen (e.g., an anti-ALPP/ALPPL2 antibody described herein) are linked in series, which are then linked to a T-cell receptor (TCR) chain at the C-terminal side. More details of CAR-T cell therapy are described, inter alia, by Nakazawa et al. (2013) *Shinshu Med. J.* 61(4): 197-203.

In certain embodiments the chimeric antigen receptor (CAR) comprises an extracellular and intracellular domain. The extracellular domain comprises a target-specific binding element otherwise referred to as an antigen binding moiety that specifically binds to ALPP and/or ALPPL2 or a domain thereof bound by M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF antibodies. In various embodiments the target specific binding element comprise an anti-ALPP/ALPPL2 antibody.

In various embodiments the intracellular domain or otherwise the cytoplasmic domain comprises, one or more costimulatory signaling region(s), and in various embodiments, a zeta chain portion. The costimulatory signaling region refers to a portion of the CAR comprising the intracellular domain of a costimulatory molecule. In various embodiments costimulatory molecules are cell surface molecules other than antigen receptors or their ligands that are required for an efficient response of lymphocytes to antigen.

Between the extracellular domain and the transmembrane domain of the CAR, or between the cytoplasmic domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. In various embodiments the spacer domain may comprise up to 300 amino acids, or in various embodiments about 10 to about 100 amino acids, and in certain embodiments about 25 to about 50 amino acids.

CAR Antigen Binding Moiety

In various embodiments the chimeric antigen receptor constructs will comprises a target-specific binding element otherwise referred to as an antigen binding moiety that specifically binds to ALPP and/or to ALPPL2, and/or to a domain of ALPP and/or to ALPPL2 that is bound by M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF antibodies. In certain embodiments the target-specific binding element comprises a binding domain from M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF antibody. In certain embodiments the target-specific binding element comprises an M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF antibody.

Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

In various embodiments the transmembrane domain can be derived either from a natural or from a synthetic source. Where the source is natural, the domain may be derived from any membrane-bound or transmembrane protein. Illustrative, but non-limiting, examples of transmembrane regions of particular use in the CAR constructs contemplated here can be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain can be synthetic, in which case it can comprise predominantly hydrophobic residues such as leucine and valine. In certain embodiments aa triplet of phenylalanine, tryptophan and valine will be found at each end of a synthetic transmembrane domain. Optionally, a short oligo- or polypeptide linker, e.g., between 2 and about 10 amino acids in length may form the linkage between the transmembrane domain and the cytoplasmic signaling domain of the CAR. In certain embodiments a glycine-serine doublet provides a particularly suitable linker.

In certain embodiment, the transmembrane domain of the CAR comprises a CD8 transmembrane domain. In on illustrative, but non-limiting, embodiment, the CD8 transmembrane domain comprises or consists of the amino acid sequence Ile Trp Ala. Pro Leu Ala Gly Thr Cys Gly Val Leu Leu Leu Ser Leu Val Ile Thr Leu Tyr Cys (SEQ ID NO:74). In certain illustrative, but non-limiting embodiments the CD8 transmembrane domain can be encoded by the nucleic acid sequence ATCTACATCT GGGCGCCCTT GGCCGGGACT TGTGGGGTCC TTCTCCTGTC ACTGGTTATC ACCCTTTACT GC (SEQ ID NO:75).

In certain embodiments the transmembrane domain of the CAR can comprise or consist of the CD8α hinge domain. In on illustrative, but non-limiting, embodiment, the CD8α hinge domain comprises or consists of the amino acid sequence Thr Thr Thr Pro Ala Pro Arg Pro Pro Thr Pro Ala Pro Thr Ile Ala Ser Gln Pro Leu Ser Leu Arg Pro Glu Ala Cys Arg Pro Ala Ala Gly Glyl Ala Val Hhis Thr Arg Gly Leu Asp Phe Ala Cys Asp Ile Tyr (SEQ ID NO:76). In certain illustrative, but non-limiting embodiments the CD8α hinge domain can be encoded by the nucleic acid sequence ACCACGACGC CAGCGCCGCG ACCACCAACA CCGGCGCCCA CCATCGCGTC GCAGCCCCTG TCCCTGCGCC CAGAGGCGTG CCGGCCAGCG GCGGGGGGCG CAGTGCACAC GAGGGGGCTG GACTTCGCCT GTGAT (SEQ ID NO:77).

Cytoplasmic Domain

The cytoplasmic domain or otherwise the intracellular signaling domain of the CAR is responsible for activation of at least one of the normal effector functions of the immune cell in which the CAR has been placed. The term "effector function" refers to a specialized function of a cell. An effector function of a T cell, for example, may be cytolytic activity, or helper activity including the secretion of cytokines. Thus the term "intracellular signaling domain" refers to the portion of a protein that transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion can be used in place of the intact chain as long as it transduces the effector function signal. The term intracellular signaling domain is thus meant to include any truncated portion of the intracellular signaling domain sufficient to transduce the effector function signal.

Illustrative, but non-limiting examples of intracellular signaling domains for use in the CAR can include a cytoplasmic sequence of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are often insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs that are known as immunoreceptor tyrosine-based activation motifs or ITAMs.

Illustrative, but non-limiting examples of ITAM containing primary cytoplasmic signaling sequences that are of particular use in the CARs contemplated herein invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3 zeta.

In one illustrative, but non-limiting embodiment, the cytoplasmic domain of the CAR can be designed to comprise the CD3-zeta signaling domain by itself or combined with any other desired cytoplasmic domain(s) useful in the context of the CAR. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include, but are not limited to, CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. In one illustrate embodiment, the co-stimulatory signaling element comprises 4-1BB.

The cytoplasmic signaling sequences within the cytoplasmic signaling portion of the CAR can be linked to each other in a random or specified order. Optionally, a short oligo- or polypeptide linker, e.g., between 2 and about 10 amino acids in length can form the linkage. In certain embodiments a glycine-serine doublet provides a particularly suitable linker.

In one illustrative but non-limiting embodiment, the cytoplasmic domain is designed to comprise the signaling domain of CD3-zeta and the signaling domain of CD28. In another embodiment, the cytoplasmic domain is designed to comprise the signaling domain of CD3-zeta and the signaling domain of 4-1BB. In yet another embodiment, the cytoplasmic domain is designed to comprise the signaling domain of CD3-zeta and the signaling domain of CD28 and 4-1BB.

In one embodiment, the cytoplasmic domain in the CAR of the invention is designed to comprise the signaling domain of 4-1BB and the signaling domain of CD3-zeta, wherein the signaling domain of 4-1BB comprises or consists of the amino acid sequence Lys Arg Gly Arg Lys Lys Leu Leu Tyr Ile Phe Lys Gln Pro Phe Met Arg Pro Val Gln Thr Thr Gln Glu Glu Asp Gly Cys Ser Cys Arg Phe Pro Glu Glu Glu Glu Gly gly cys Glu Leu (SEQ ID NO:78) and/or the signaling domain of CD3-zeta comprises or consists of the amino acid sequence Arg Val Lys Phe Ser Arg Ser Ala Asp Ala Pro Ala Tyr Lys Gln Gly Gln Asn Gln Leu Tyr Asn Glu Leu Asn Leu Gly ARg Arg Glu Glu Tyr Asp Val Leu Asp Lys Arg Arg Gly Arg Asp Pro Glu Met Gly Gly Lys Pro Arg Arg Lys Asn Pro Gln Glu Gly Leu Tyr Asn Glu Leu Gln Lys Asp Lys Met Ala glu Ala Tyr Ser Glu Ile Gly Met Lys Gly Glu Arg Arg Arg Gly Lys Gly His Asp Gly Leu Tyr Gln Gly Leu Ser Thr Ala Thr Lys Asp Thr Tyr Asp Ala Leu His Met Gln Ala Leu Pro Pro Arg (SEQ ID NO:79.

In one illustrative, but non-limiting embodiment, the signaling domain of 4-1BB is encoded by a nucleic acid sequence that comprises or consists of the sequence AAACGGGGCA GAAAGAAACT CCTGTATATA TTCAAACAAC CATTTATGAG ACCAGTACAA ACTACTCAAG AGGAAGATGG CTGTAGCTGC CGATTTCCAG AAGAAGAAGA AGGAGGATGT GAACTG (SEQ ID NO:80). In one illustrative, but non-limiting embodiment, the signaling domain of CD3-zeta is encoded by a nucleic acid that comprises or consists of the sequence AGAGTGAAGT TCAGCAGGAG CGCAGACGCC CCCGCGTACA AGCAGGGCCA GAACCAGCTC TATAACGAGC TCAATCTAGG ACGAAGAGAG GAGTACGATG TTTTGGACAA GAGACGTGGC CGGGACCCTG AGATGGGGGG AAAGCCGAGA AGGAAGAACC CTCAGGAAGG CCTGTACAAT GAACTGCAGA AAGATAAGAT GGCGGAGGCC TACAGTGAGA TTGGGATGAA AGGCGAGCGC (SEQ ID NO:81).

The foregoing embodiments are illustrative and non-limiting. Using the teachings provided herein numerous CARs directed against ALPPP and/or ALPPL2 will be available to one of skill in the art.

Vectors

In various embodiments a DNA construct comprising sequences of a CAR as described herein is provided. In certain embodiments the CAR comprising an antigen binding moiety that specifically binds to ALPP and/or to ALPPL2, and/or to a domain of ALPP and/or ALPPL2 bound by antibody M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF, wherein the nucleic acid sequence of the antigen binding moiety is operably linked to the nucleic acid sequence of an intracellular domain. An exemplary intracellular domain that can be used in the CAR of the invention includes but is not limited to the intracellular domain of CD3-zeta, CD28, 4-1BB, and the like. In some instances, the CAR can comprise any combination of CD3-zeta, CD28, 4-1BB, and the like.

In one embodiment, the CAR of the invention comprises an anti-ALPP/ALPPL2 scFv (e.g., M25AD, M25ADX, M25, etc.), a human CD8 hinge and transmembrane domain, and human 4-1BB and CD3zeta signaling domains.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

In certain embodiments vectors are provided in which a nucleic acid sequence encoding a CAR as described herein is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding CARs can be achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs described herein can also be used for nucleic acid immunization and gene therapy, using standard gene delivery protocols. Methods for gene delivery are known in the art (see, e.g., U.S. Pat. Nos. 5,399,346, 5,580,859, and 5,589,466). In certain embodiments gene therapy vectors are provided.

The nucleic acid encoding the CAR can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

In certain embodiments the expression vector may be provided to a cell in the form of a viral vector. Viral vector technology is well known in the art and is described, for example, in Sambrook et al. (2001) Molecular Cloning: A Laboratory Manual, Cold Spring Harbor Laboratory, New York), and in other virology and molecular biology manuals. Viruses that are useful as vectors include, but are not limited to, retroviruses, adenoviruses, adeno-associated viruses, herpes viruses, and lentiviruses (including self-inactivating lentivirus vectors). In general, a suitable vector contains an origin of replication functional in at least one organism, a promoter sequence, convenient restriction endonuclease sites, and one or more selectable markers (see, e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1alpha (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Moreover the constructs are not be limited to the use of constitutive promoters and inducible and/or tissue-specific promoters are also contemplated. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In certain embodiments, in order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes can be used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al. (2000) *FEBS Letts.* 479: 79-82). Suitable expression systems are well known and may be prepared using known techniques or obtained commercially. In general, the construct with the minimal 5' flanking region showing the highest level of expression of reporter gene is identified as the promoter. Such promoter regions can be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art (see, e.g., Sambrook et al. (2001) Molecular Cloning: A Laboratory Manual, Cold Spring Harbor Laboratory, New York). One illustrative, but non-limiting method for the introduction of a polynucleotide into a host cell is calcium phosphate transfection.

Biological methods for introducing a polynucleotide of interest into a host cell can include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like (see, e.g, U.S. Pat. Nos. 5,350,674 and 5,585,362, and the like).

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An illustrative colloidal system for use as a delivery vehicle in vitro and in vivo is a liposome (e.g., an artificial membrane vesicle).

In the case where a non-viral delivery system is utilized, one illustrative delivery vehicle is a lipid and/or a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

In various embodiments lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform can be used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al. (1991) *Glycobiology* 5: 505-510). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Sources of Immune Cells

In certain embodiments prior to expansion and genetic modification of the immune cells (e.g. T cells) described herein of the invention, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as FICOLL™ separation. In one illustrative embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In another illustrative embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3.times.28)-conjugated beads, such as DYNABEADS® M-450 CD3/CD28 T, for a time period sufficient for positive selection of the desired T cells. In one illustrative embodiment, the time period is about 30 minutes. In certain illustrative embodiments, the time period ranges from 30 minutes to 36 hours or longer and all integer values there between. In a certain embodiments the time period is at least 1, 2, 3, 4, 5, or 6 hours. In yet another embodiment, the time period is 10 to 24 hours. In one embodiment, the incubation time period is 24 hours. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells that typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a another embodiment, greater than 100 million cells/ml is used. In a another embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In another embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5\times10^6$/ml. In another embodiment, the concentration used can be from about $1\times10^5$/ml to $1\times10^6$/ml, and any integer value in between.

In certain embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C., e.g., at a rate of 1° C. per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, the T cells may be expanded, frozen, and used at a later time. In certain embodiments, samples are collected from a patient shortly after diagnosis of a particular disease (e.g., cancer) as described herein but prior to any treatments. In a further embodiment, the cells are isolated from a blood sample or an apheresis from a subject prior to any number of relevant treatment modalities, including but not limited chemotherapy, surgery, and/or radiotherapy.

In certain embodiments T cells are obtained from a subject directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

Whether prior to or after genetic modification of the T cells to express a desirable CAR (e.g., a CAR described herein), the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Publications No: 2006/0121005.

In various embodiments the T cells are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For costimulation of an accessory molecule on the surface of the T cells, a ligand that binds the accessory molecule can be used. For example, a population of T cells can be contacted with an anti-CD3 antibody and an anti-CD28 antibody, under conditions appropriate for stimulating proliferation of the T cells. To stimulate proliferation of either CD4$^+$ T cells or CD8$^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (see, e.g., Berg et al. (1998) *Transplant Proc.* 30(8): 3975-3977, 1998; Haanen et al. (1999) *J. Exp. Med.* 190(9): 1319-1328; Garland et al. (1999) *J. Immunol Meth.* 227(1-2): 53-63, and the like).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent that will bind to the agents (see, e.g., U.S. Patent Pub. Nos. 2004/0101519 and 2006/0034810 for artificial antigen presenting cells (aAPCs) that are contemplated for use in activating and expanding T cells in the present invention).

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for CD4$^+$ T cell expansion and T cell growth is used. In certain embodiments, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect, more anti-CD28 antibody is bound to the particles than anti-CD3 antibody, i.e., the ratio of CD3:CD28 is less than one. In certain embodiments, the ratio of anti CD28 antibody to anti CD3 antibody bound to the beads is greater than 2:1. In one particular embodiment, a 1:100 CD3:CD28 ratio of antibody bound to the beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

In certain embodiments ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In certain embodiments the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, 10$^4$ to 10$^9$ T cells) and beads (for example, DYNABEADS® M-450 CD3/CD28 T paramagnetic beads at a ratio of 1:1) are combined in a buffer, e.g., PBS (without divalent cations such as, calcium and magnesium).

Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one illustrative embodiment, the mixture may be cultured for several hours (about 3 hours) to about 14 days or any hourly integer value in between. In another embodiment, the mixture may be cultured for 21 days. In one embodiment the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-.gamma., IL-4, IL-7, GM-CSF, IL-10, IL-12, IL-15, TGF-β, and TNF-α or any other additives for the growth of cells known to the skilled artisan. Other additives for the growth of cells include, but are not limited to, surfactant, plasmanate, and reducing agents such as N-acetyl-cysteine and 2-mercapto-ethanol. In certain embodiments media can include RPMI 1640, AIM-V, DMEM, MEM, α-MEM, F-12, X-Vivo 15, X-Vivo 20, and the like. Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, can be included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4$^+$) that is greater than the cytotoxic or suppressor T cell population ($T_c$, CD8$^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of T-cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application of CARs

In various embodiments cells transduced with a vector encoding the CARs described herein are provided. In one illustrative embodiment T cells transduced with a lentiviral vector (LV) are provided where the LV encodes an anti-ALPP/ALPPL2 CAR as described herein. Therefore, in some instances, the transduced T cell can elicit a CAR-mediated T-cell response.

In certain embodiments the use of a CAR to redirect the specificity of a primary T cell to a tumor antigen is provided. Thus, methods for stimulating a T cell-mediated immune response to a target cell population or tissue in a mammal comprising the step of administering to the mammal a T cell that expresses a CAR as described herein are provided.

In certain embodiments methods of cellular therapy are provided where the cellular therapy utilizes cells (e.g., immunomodulatory cells such as T cells) genetically modified to express a CAR as described herein and the CAR expressing cell (e.g., CAR T cell) is infused to a recipient in need thereof. The infused cell is able to kill cancer cells in the recipient, particularly cancer cells expressing ALPP and/or ALPPL2 (e.g., mesothelioma, testicular cancer, endometrial cancer, and subsets of ovarian, pancreatic, and non small cell lung cancers). Unlike antibody therapies, CAR T cells are able to replicate in vivo resulting in long-term persistence that can lead to sustained tumor control.

In one embodiment, the CAR T cells described herein can undergo robust in vivo T cell expansion and can persist for an extended amount of time. In another embodiment, the CAR T cells described herein evolve into specific memory T cells that can be reactivated to inhibit any additional tumor formation or growth. For example, in certain embodiments the CAR T cells can undergo robust in vivo T cell expansion and persist at high levels for an extended amount of time in blood and bone marrow and form specific memory T cells. Without wishing to be bound by any particular theory, CAR T cells may differentiate in vivo into a central memory-like state upon encounter and subsequent elimination of target cells expressing the surrogate antigen.

Without wishing to be bound by any particular theory, the anti-tumor immunity response elicited by the CAR-modified T cells may be an active or a passive immune response. In addition, the CAR mediated immune response may be part of an adoptive immunotherapy approach in which CAR-modified T cells induce an immune response specific to the antigen binding moiety in the CAR. For example, the anti-ALPP/ALPPL2 CAR cells elicit an immune response specific against cancer cells ALPPL2.

The cancers that may be treated include any cancer that expresses or overexpresses ALPP and/or ALPPL2 or a fragment thereof to which an M25ADLF, M25ADLFEG, M25ADLFDS, M25FYIA, M25FYIAEG, M25FYIADS, M25, M25EG, M25DS, M25AELF, M25AELFEG, M25AELFDS, M25ADL99P, M25ADL99G, M25ADS95R, M25ADD28G, M25ADS91G, M25ADY93H, M25ADYHSRLF, M25GRITSGFYGDwtLC, M25FSITSGFYGDwtLC, M253018IA, M253018LF, M25AD, M25ADX, ALPPL2rd3_1, ALPPL2rd3_2, M25AGIA, M25AGLF, M25ASIA, M25ASLF, M25ASwt, M25AVIA, M25AVLF, M25ALIA, M25ALLF, M25wtIA, and/or M25wtLF antibody specifically binds.

Cancers that may be treated include tumors that are not vascularized, or not yet substantially vascularized, as well as vascularized tumors. The cancers may comprise non-solid tumors or may comprise solid tumors, or may comprise cancer cells (e.g., cancer stem cells). Types of cancers to be treated with the CARs of the invention include, but are not limited to mesothelioma, testicular cancer, endometrial cancer, and subsets of ovarian, pancreatic, and non-small cell lung cancers.

In certain embodiments the CAR-modified T cells described herein can also serve as a type of vaccine for ex vivo immunization and/or in vivo therapy in a mammal In certain embodiments the mammal is a non-human mammal and in other embodiments the mammal is a human.

With respect to ex vivo immunization, at least one of the following can occur in vitro prior to administering the cell into a mammal: i) expansion of the cells, ii) introducing a nucleic acid encoding a CAR to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. In certain embodiments the CAR-modified cell can be autologous with respect to the recipient. Alternatively, the cells can be allogeneic, syngeneic or xenogeneic with respect to the recipient.

A suitable, but non-limiting procedure for ex vivo expansion of hematopoietic stem and progenitor cells is described in U.S. Pat. No. 5,199,942 and can be applied to the cells described herein. Other suitable methods are known in the art and the methods are not limited to any particular method of ex vivo expansion of the cells. Briefly in certain embodiments ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In certain embodiments, in addition to using a cell-based vaccine in terms of ex vivo immunization, compositions and methods are also provided for in vivo immunization to elicit an immune response directed against cells displaying ALPP and/or ALPPL2 in a subject.

In various embodiments the CAR-modified cells described herein can be administered either alone, or as a pharmaceutical composition in combination with diluents and/or with other components such as IL-2 or other cytokines or cell populations. Briefly, in certain embodiments pharmaceutical compositions can comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. In certain embodiments compositions comprising CAR modified cells are formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al. (1988) *New Eng. J. Med.* 319: 1676). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom as described herein, and reinfuse the patient with these activated and expanded T cells. In certain embodiments this process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a subject by intradermal or subcutaneous injection. In another embodiment, the T cell compositions of the present invention are preferably administered by i.v. injection. In certain embodiments the compositions of T cells may be injected directly into a tumor, lymph node, or site of infection.

The dosage of the above treatments to be administered to a sibkect will vary with the precise nature of the condition being treated and the recipient of the treatment. The scaling of dosages for human administration can be performed according to art-accepted practices.

EXAMPLES

The following examples are offered to illustrate, but not to limit the claimed invention.

Example 1

We have previously used subtractive phage antibody display library selection to identify human monoclonal antibodies that bind with high specificity to living tumor cells and tumor cells in situ residing in their natural tissue microenvironment. In our work on mesothelioma, an incurable orphan disease, we identified a novel antibody that binds specifically to mesothelioma cell lines and tissues but not any other cell lines studied.

To further characterize the target antigen expression on normal tissues, we biotin-labeled the IgG1 derived from the scFv and stained the FDA standard panel of normal human tissues for therapeutic antibody evaluation which contains 90 cores (triplicates) of 30 organs. We found no staining for all normal human tissues except placental trophoblasts (Table 2).

TABLE 2

Immunohistochemistry (IHC) on normal human tissue.

| Tissue Name | Staining | Tissue Name | Staining | Tissue Name | Staining |
|---|---|---|---|---|---|
| Lymph node | N | Ovary | N | Small intestine | N |
| Skeletal muscle | N | Pancreas | N | Peripheral nerve | N |
| Prostate | N | Salivary gland | N | Uterus | N |
| Kidney | N | Pituitary gland | N | Cerebellum | N |
| Liver | N | Placenta | ++++ | Cerebrum | N |
| Lung | N | Skin | N | Testis | N |
| Stomach | N | Spinal cord | N | Thymus | N |
| Esophagus | N | Spleen | N | Thyroid gland | N |
| Heart | N | Colon | N | Ureter | N |
| Uterine cervix | N | Smooth muscle | N | | |

N: no staining or no change of stain compared to secondary only control.
++++: strong staining.
Biotin-labeled M25 IgG1 was used in the study.

This exquisite specificity prompted us to identify the target antigen by immunoprecipitation and mass spectrometry. The antigen was identified as ALPPL2 and confirmed by ectopic expression of ALPPL2 cDNA in a target negative cell line (HEK293a). ALPPL2 is a member of the alkaline phosphatase (AP) family, consisting of two closely related isoforms expressed in placental trophoblasts (ALPPL2 and ALPP), and two widely expressed members ALPL (tissue-nonspecific, liver/bone/kidney) and ALPI (intestinal). Our M25 antibody binds specifically to the placentally expressed ALPPL2 (and ALPP) but not ALPL and ALPI that are expressed outside the placenta.

Interestingly, our preliminary data from competitive FACS using soluble antigens suggest that our antibody binds preferentially the cell surface form, potentially alleviating some of the concerns of antigen shedding. While this phenomenon is under investigation, without being bound to a particular theory, it is believed that ALPPL2 exists as a stable dimer on the cell surface (a common property of the AP family), but less so in solution due to lack of membrane association that stabilizes the otherwise weak monomer-monomer interaction, which leads to an avidity-based preferential binding by our antibody to membrane ALPPL2. It should be pointed out that our antibody was selected from phage display libraries on live tumor cells, as opposed to recombinant soluble proteins, thus it may not be entirely surprising that the antibody possesses this novel property.

Identification of the antigen allowed us to perform immunohistochemistry (IHC) studies on paraffin-embedded tumor tissues. We found that the antigen is widely expressed in mesothelioma, testicular cancer, endometrial cancer, and subsets of ovarian, pancreatic, and non small cell lung cancers. We also generated a recombinant extracellular domain (ECD)-Fc fusion molecule and used it to select out additional high affinity antibodies by FACS from a newly created, cell surface binder-enriched yeast antibody display library. We have identified a variant of M25, M25AD, which binds to tumor cells with an apparent affinity of 28 p in its IgG1 form.

Figure 3A:
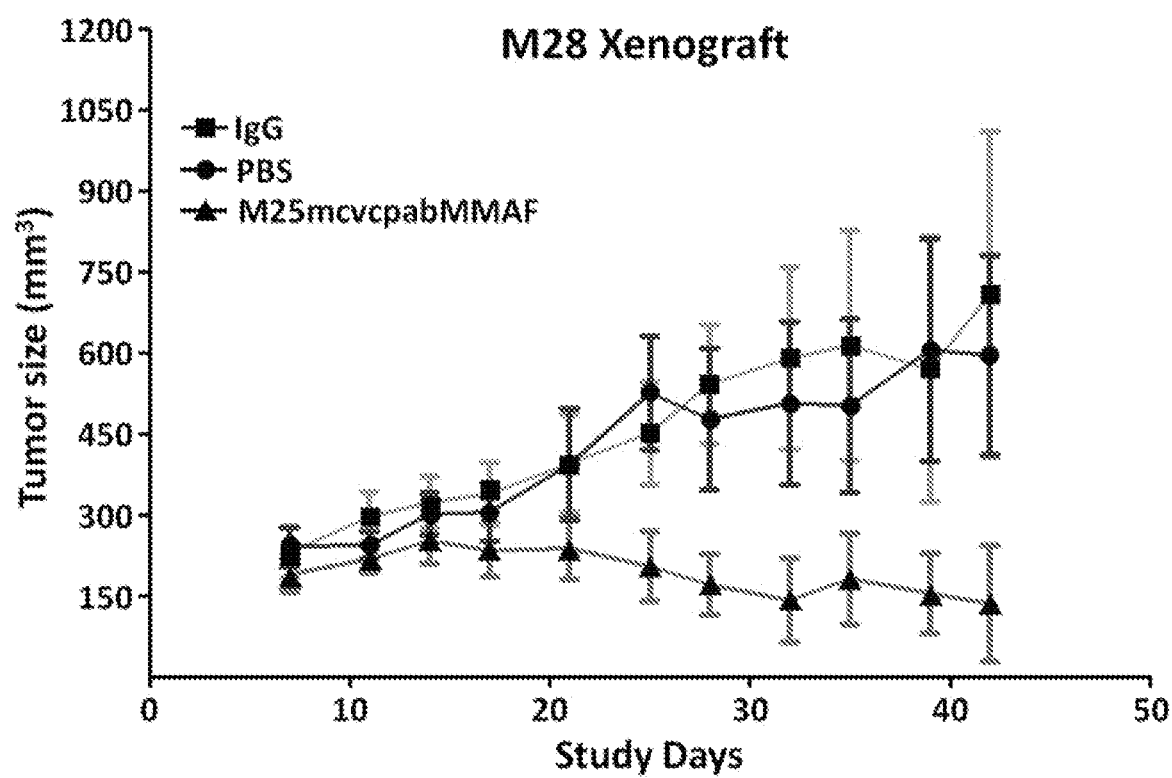
FIGS. 3A and 3B show that anti-ALLP/ALLPL2 ADC potently inhibit tumor xenograft growth in vivo.
Figure 3B:
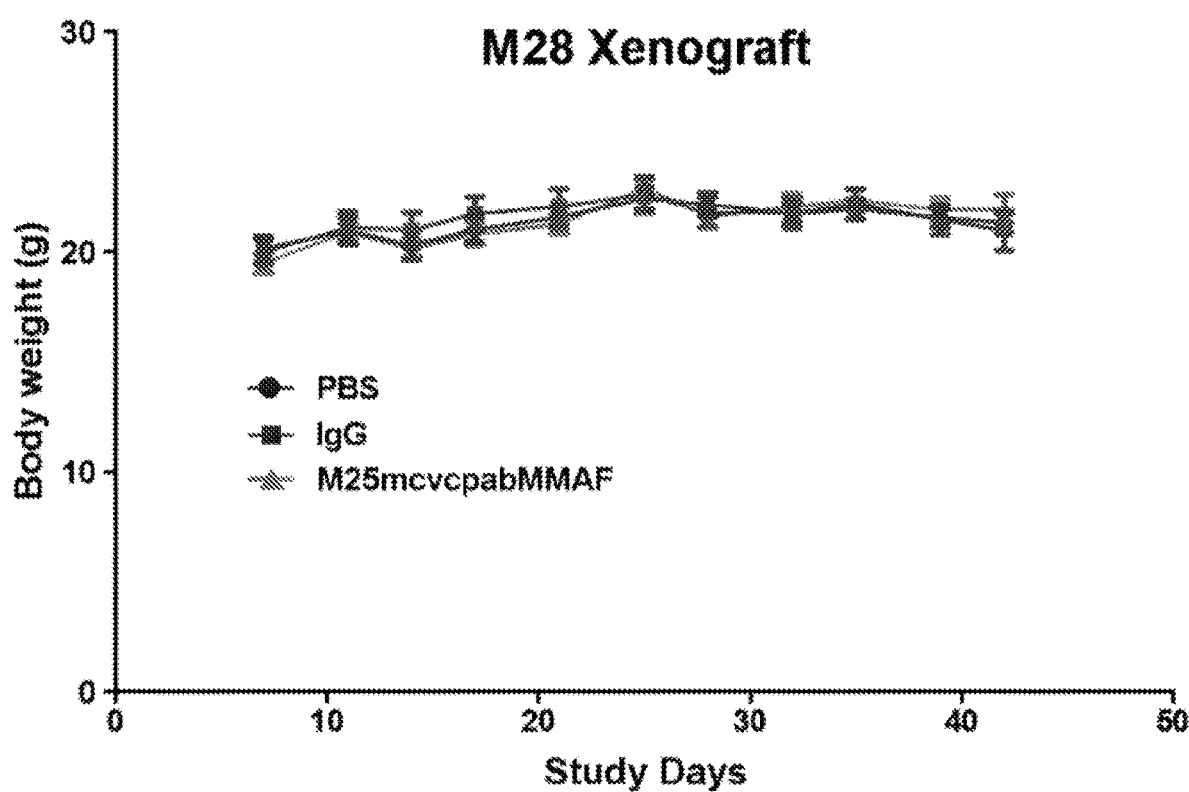
Figure 4:
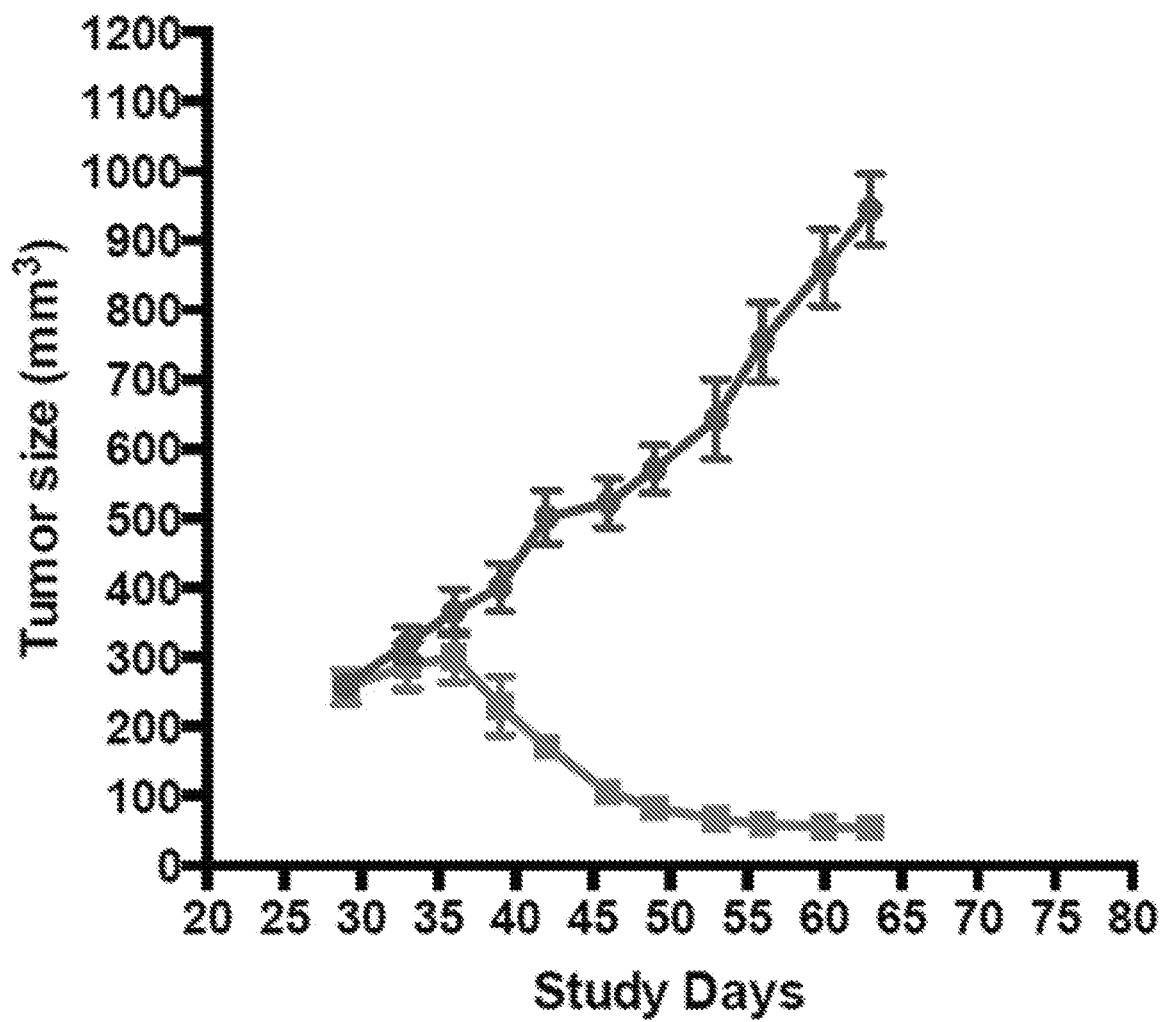
FIG. 4 illustrates the evaluation of MMAE-based ADC in mesothelioma xenograft model. M25AD-mcvcpab-MMAE was injected at 3 mg/kg every 3-4 days for 5 times. A non-binding IgG1-mcvcpab-MMAE was used as the control.

It is believed that the exquisite tumor specificity of the target antigen and our antibody permits development of novel targeted therapy and immunotherapy. We have already developed an ADC by conjugating monomethyl auristatin F (MMAF) to the M25AD IgG1 and demonstrated anti-tumor activity in vitro (FIG. 2) and in vivo (FIG. 3). We also constructed an M25AD ADC using monomethyl auristatin E (MMAE) and obtained potent inhibition of mesothelioma xenografts in vivo at a dose of 3 mg/kg (FIG. 4).

Figure 5:
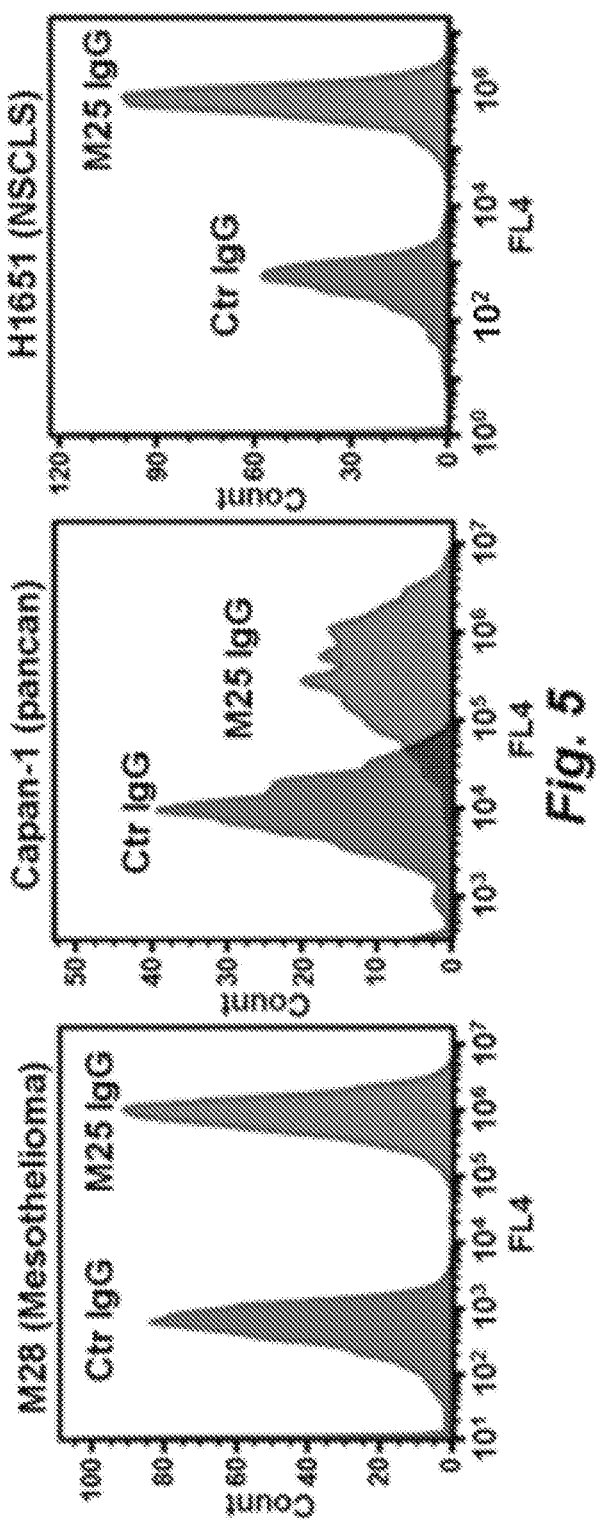
FIG. 5 shows FACS of our anti-ALPPL2 antibody M25 on mesothelioma, pancreatic and non-small cell lung cancer lines.
Figure 6:
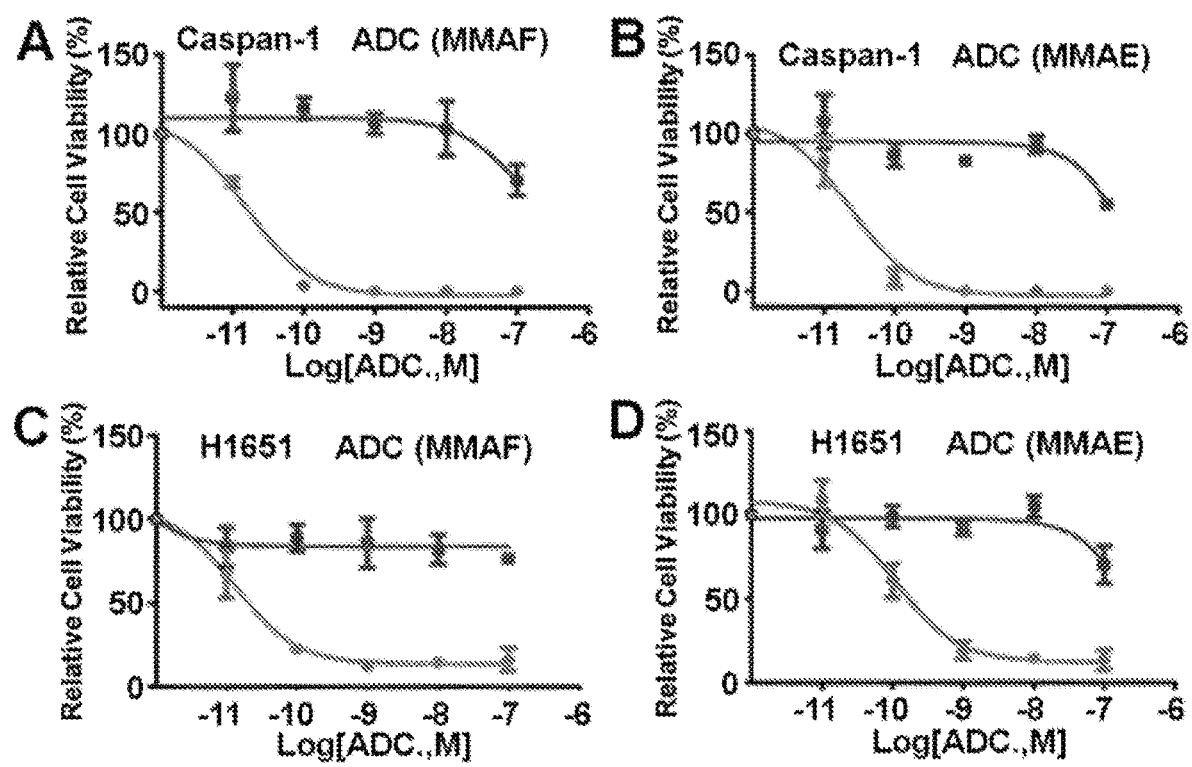
FIG. 6 shows kill curves of M25AD-MMAF and -MMAE on pancreatic (Capan-1, panels A and B) and non-small cell lung cancer (H1651, panels C and D) lines. All conjugates are IgG1-mcvcpab-MMAF (panels A and C) or MMAE (panels B and D).
Figure 7:
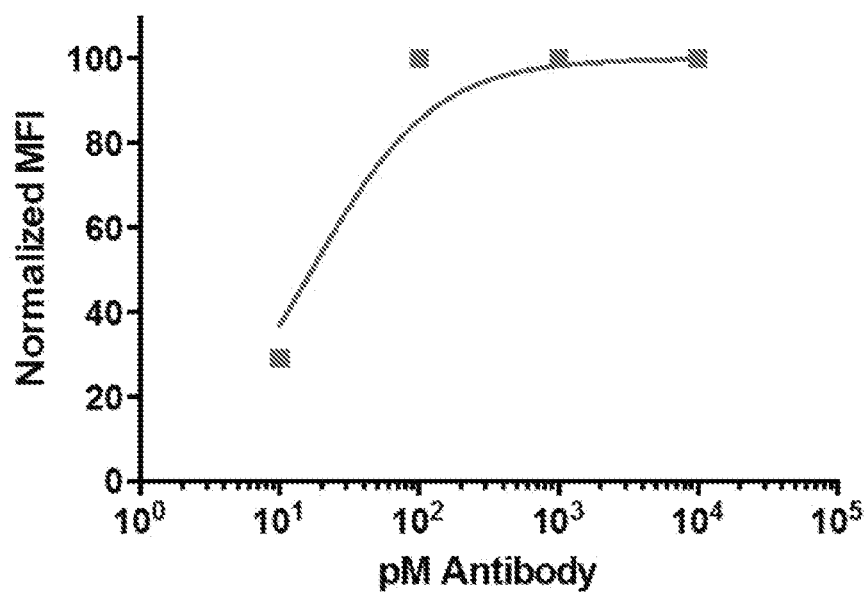
FIG. 7 shows FACS analysis of M25ADLF IgG1 binding to live HEK293 cells transfected with ALPPL2-expressing plasmid, along with a plasmid expressing the green fluorescence protein (GFP). Cells were incubated with antibody at room temperature for 1 h in PBS/0.2% fetal calf serum, washed three times and further incubated with ALEXA-FLOU®-647-labled anti-human secondary antibody. GFP+ cells were gated and analyzed for mean fluorescence intensity (MFI). Normalized MFI was used to curve fit using Prism (GraphPad) to derive the apparent KD value of 17.04+/−6.18 pM. Similar binding results were obtained on ALPP-transfected cells. There is no binding to ALPL-transfected cells. Binding to APLI-transfected cells has an apparent KD value >5 µM.
Figure 8:
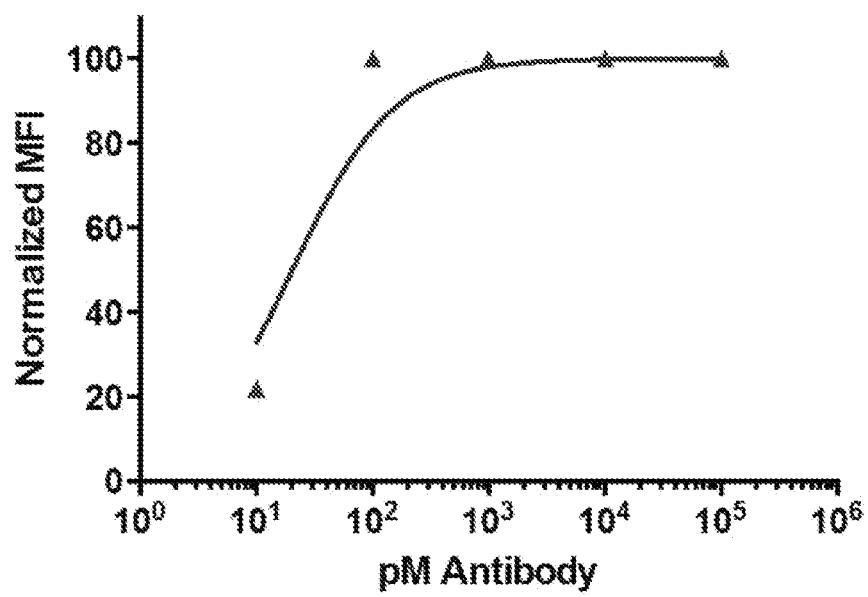
FIG. 8 shows FACS analysis of M25FYIA IgG1 binding to live HEK293 cells transfected with ALPPL2-expressing plasmid, along with a plasmid expressing the green fluorescence protein (GFP). Cells were incubated with antibody at room temperature for 1 h in PBS/0.2% fetal calf serum, washed three times and further incubated with ALEXA-FLOU®-647-labled anti-human secondary antibody. GFP+ cells were gated and analyzed for mean fluorescence intensity (MFI). Normalized MFI was used to curve fit using Prism (GraphPad) to derive the apparent KD value of 20.36+/−7.85 pM. Similar binding results were obtained on ALPP-transfected cells. T here is no binding to ALPL-transfected cells. Binding to ALPI-transfected cells has an apparent KD value >3.3 µM.
Figure 9:
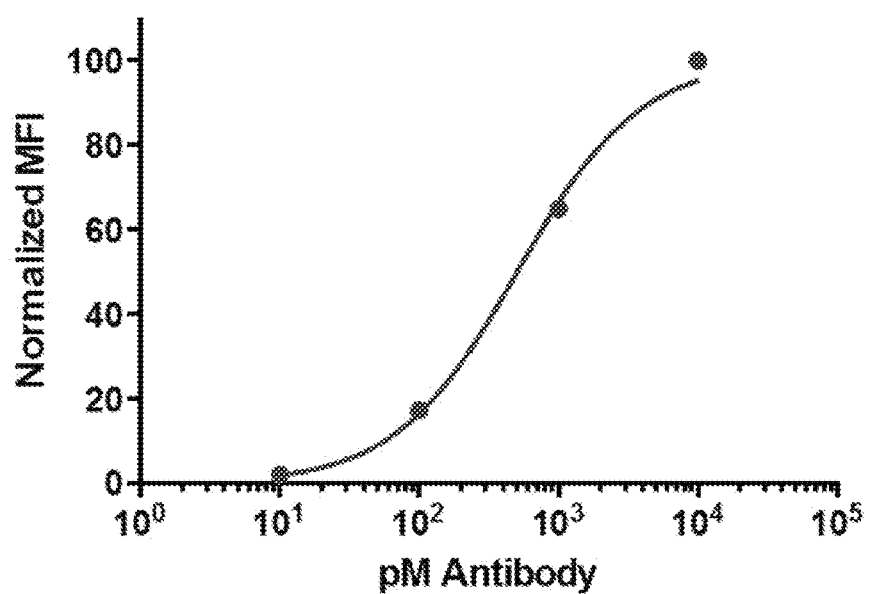
FIG. 9 shows FACS analysis of M25 IgG1 binding to live HEK293 cells transfected with ALPPL2-expressing plasmid, along with a plasmid expressing the green fluorescence protein (GFP). Cells were incubated with antibody at room temperature for 1 h in PBS/0.2% fetal calf serum, washed three times and further incubated with ALEXAFLOU®-647-labled anti-human secondary antibody. GFP+ cells were gated and analyzed for mean fluorescence intensity (MFI). Normalized MFI was used to curve fit using Prism (GraphPad) to derive the apparent KD value of 506.1+/−55.95 pM. Similar binding results were obtained on ALPP-transfected cells. There is no binding to either ALPL or ALPI-transfected cells.

In addition to mesothelioma cells, we found cell surface ALPPL2 expression in a few other tumor cell lines, including pancreatic cancer line Capan-1, and non small cell lung cancer line H1661 (FIG. 5), with the study on ovarian cancer lines ongoing. Both M25AD-MMAF and M25AD-MMAE potently inhibit growth of pancreatic and non small cell lung cancer cell lines in vitro (FIG. 6). Pending further in vivo confirmation, it is believed that the novel anti-ALPPL2 ADC and our ALPPL2-targeting strategy in general is be applicable to multiple incurable cancers with dire clinical needs.

In addition to ADC, the high tumor specificity of the tumor antigen allows the development of various forms of targeted immunotherapy, e.g., a bispecific antibody that recruits and activates T cells at tumor sites, as well as other platforms such as chimeric antigen receptor engineered T cell (CAR-T) and immunocytokines.

In one illustrative, but non-liming embodiment, a novel ALPPL2/CD3 bispecific antibody is produced. Due to the highly restricted expression pattern of the target antigen, on-target toxicity is expected to be minimal. Combined with high level antigen expression on the tumor cell surface, a wide therapeutic window is expected. The bispecific agent is a pure biologic, presenting a relatively simple form for development and manufacturing.

In various embodiments two biotherapeutic drug candidates are contemplated: (1) An ADC, for which we have preformed preliminary studies and demonstrated in vitro and in vivo anti-tumor activity. Additional payloads including DNA chelating agents and linkers can be tested to optimize the therapeutic index and the best candidate can be advanced to IND-enabling studies. (2) Targeted immunotherapy in the form of a bispecific human antibody against the tumor-specific antigen ALPPL2 and the T cell receptor CD3.

The exquisite tumor specificity of ALPPL2 presents an excellent opportunity to develop a novel ADC with the potential of achieving durable responses in the clinic as a single agent. In addition to auristatin derivatives that we have already obtained promising preclinical results with, more potent warheads such as PBD (or drugs with similar potency) can be used to construct novel ADCs. Dosing studies can be performed in vivo using xenografts of mesothelioma, pancreatic cancer, non small cell lung cancer, and ovarian cancer.

Additionally a bispecific anti-ALPPL2/CD3 is contemplated for tumor-specific immune activation. An anti-ALPPL2/CD3 bispecific using DART or BiTE platforms can be created. Blinatumomab is an FDA approved BiTE therapeutic and its anti-CD3 scFv sequence is available and can be used as a reference to the current standard. Anti-CD3 scFvs isolated from additional selection and screening can be benchmarked against this current standard.

Additionally in certain embodiments an IHC-based biomarker is contemplated that enables assessment of antigen expression levels for patient stratification. For example, an ELISA-based biomarker assay can enables assessment of tumor status by a serum-based test.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent application cited herein are hereby incorporated by reference in their entirety for all purposes.

What is claimed is:

1. An isolated antibody that binds human placentally expressed ALPP and/or ALPPL2, but not ALPL and ALPI that are expressed outside the placenta wherein:
said antibody comprises a heavy chain variable region (VH) and a light chain variable region (VL), where:
said heavy chain variable region comprises a variable heavy M25FYIA antibody CDR1 comprising the amino acid sequence GFTFSSYA (residues 26-33 of SEQ ID NO:6), a variable heavy M25FYIA antibody CDR2 comprising the amino acid sequence ISYDGSNK (residues 51-58 of SEQ ID NO:6, and a variable heavy M25FYIA antibody CDR3 comprising the amino acid sequence AKEGDSSRWSYDL (residues 97-109 of SEQ ID NO:6); and
said light chain variable region comprises a variable light M25FYIA antibody CDR1 comprising the amino acid sequence SSDVGGYNY (residues 161-169 of SEQ ID NO:6), a variable light M25FYIA antibody CDR2 comprising the amino acid sequence DVT (residues 187-189 of SEQ ID NO:6), and a variable light M25FYIA antibody CDR3 consisting of the amino acid sequence SSYTIASTLVV (residues 226-236 of SEQ ID NO:6).

2. The antibody of claim 1, wherein said antibody preferentially binds the cell surface form of ALPPL2 as compared to the shed form of ALPPL2.

3. The antibody of claim 1, wherein:
said antibody binds a cell expressing ALPPL2 with an affinity of better than about 5 nM; and/or
said antibody binds a cell expressing ALPPL2 with an affinity of better than about 50 pM in its IgG1 form.

4. The antibody of claim 1, wherein:
said antibody comprises a heavy chain variable region (VH) of an M25FYIA antibody comprising the amino acid sequence QVQLQQSGGGLVKPGGSLRLSCAASGFTFSSYAMHWVRQAPGKGLEWVAVISYDGSN KYYADSVKGRFTISRDNSKNTLYLQMDSLRAEDTAVYYCAKEGDSSRWSYDLWGRGT LVTVSS (residues 1-120 of SEQ ID NO:6); and
said antibody comprises a light chain variable region (VL) of an M25FYIA antibody comprising the amino acid sequence QSALTQPASVSGSPGQSITISCTGTSSDVGGYNYVSWYQQHPGKAPKVMIYDVTNRPSG VSNRFSGSKSGNTASLTISGLQAEDEADYYCSSYTIASTLVVFGGGTKLTVL (residues 136-246 of SEQ ID NO:6).

5. The antibody of claim 1, wherein said antibody is selected from the group consisting of an intact immunoglobulin, an Fv, a Fab, a (Fab')₂, a (Fab')₃, an IgGΔCH2, and a single-chain antibody.

6. An immunoconjugate comprising the antibody of claim 1 attached to an effector wherein said effector is selected from the group consisting of a second antibody, a detectable label, a cytotoxin or cytostatic agent, a liposome containing a drug, a radionuclide, a drug, a prodrug, an immune modulator, a viral particle, a cytokine, and a chelate.

7. The immunoconjugate of claim 6, wherein said effector is a second antibody.

8. The immunoconjugate of claim 7, wherein said second antibody is an antibody that binds to CD3.

9. The immunoconjugate of claim 6, wherein:
said antibody comprises a heavy chain variable region (VH) of an M25FYIA antibody comprising the amino acid sequence QVQLQQSGGGLVKPGGSLRLSCAASGFTFSSYAMHWVRQAPGKGLEWVAVISYDGSN KYYADSVKGRFTISRDNSKNTLYLQMDSLRAEDTAVYYCAKEGDSSRWSYDLWGRGT LVTVSS (residues 1-120 of SEQ ID NO:6); and
said antibody comprises a light chain variable region (VL) of an M25FYIA antibody comprising the amino acid sequence QSALTQPASVSGSPGQSITISCTGTSSDVGGYNYVSWYQQHPGKAPKVMIYDVTNRPSG VSNRFSGSKSGNTASLTISGLQAEDEADYYCSSYTIASTLVVFGGGTKLTVL (residues 136-246 of SEQ ID NO:6).

10. The immunoconjugate of claim 6, wherein said antibody is an intact immunoglobulin.

11. A pharmaceutical formulation said formulation comprising:
a pharmaceutically acceptable carrier and the antibody of claim 1.

* * * * *

SEQUENCE LISTING

```
<160> NUMBER OF SEQ ID NOS: 83

<210> SEQ ID NO 1
<211> LENGTH: 535
<212> TYPE: PRT
<213> ORGANISM: Homo sapiens

<400> SEQUENCE: 1

Met Leu Gly Pro Cys Met Leu Leu Leu Leu Leu Leu Gly Leu Arg
1               5                   10                  15

Leu Gln Leu Ser Leu Gly Ile Ile Pro Val Glu Glu Asn Pro Asp
                20                  25                  30

Phe Trp Asn Arg Glu Ala Ala Glu Ala Leu Gly Ala Ala Lys Lys Leu
            35                  40                  45

Gln Pro Ala Gln Thr Ala Ala Lys Asn Leu Ile Ile Phe Leu Gly Asp
        50                  55                  60

Gly Met Gly Val Ser Thr Val Thr Ala Ala Arg Ile Leu Lys Gly Gln
65                  70                  75                  80

Lys Lys Asp Lys Leu Gly Pro Glu Ile Pro Leu Ala Met Asp Arg Phe
                85                  90                  95

Pro Tyr Val Ala Leu Ser Lys Thr Tyr Asn Val Asp Lys His Val Pro
                100                 105                 110

Asp Ser Gly Ala Thr Ala Thr Ala Tyr Leu Cys Gly Val Lys Gly Asn
            115                 120                 125

Phe Gln Thr Ile Gly Leu Ser Ala Ala Ala Arg Phe Asn Gln Cys Asn
        130                 135                 140

Thr Thr Arg Gly Asn Glu Val Ile Ser Val Met Asn Arg Ala Lys Lys
145                 150                 155                 160

Ala Gly Lys Ser Val Gly Val Val Thr Thr Thr Arg Val Gln His Ala
                165                 170                 175

Ser Pro Ala Gly Thr Tyr Ala His Thr Val Asn Arg Asn Trp Tyr Ser
            180                 185                 190

Asp Ala Asp Val Pro Ala Ser Ala Arg Gln Glu Gly Cys Gln Asp Ile
        195                 200                 205

Ala Thr Gln Leu Ile Ser Asn Met Asp Ile Asp Val Ile Leu Gly Gly
    210                 215                 220

Gly Arg Lys Tyr Met Phe Arg Met Gly Thr Pro Asp Pro Glu Tyr Pro
225                 230                 235                 240

Asp Asp Tyr Ser Gln Gly Gly Thr Arg Leu Asp Gly Lys Asn Leu Val
                245                 250                 255

Gln Glu Trp Leu Ala Lys Arg Gln Gly Ala Arg Tyr Val Trp Asn Arg
            260                 265                 270

Thr Glu Leu Met Gln Ala Ser Leu Asp Pro Ser Val Thr His Leu Met
        275                 280                 285

Gly Leu Phe Glu Pro Gly Asp Met Lys Tyr Glu Ile His Arg Asp Ser
    290                 295                 300

Thr Leu Asp Pro Ser Leu Met Glu Met Thr Glu Ala Ala Leu Arg Leu
```

```
            305                 310                 315                 320

Leu Ser Arg Asn Pro Arg Gly Phe Phe Leu Phe Val Glu Gly Gly Arg
                325                 330                 335

Ile Asp His Gly His His Glu Ser Arg Ala Tyr Arg Ala Leu Thr Glu
                340                 345                 350

Thr Ile Met Phe Asp Asp Ala Ile Glu Arg Ala Gly Gln Leu Thr Ser
                355                 360                 365

Glu Glu Asp Thr Leu Ser Leu Val Thr Ala Asp His Ser His Val Phe
370                 375                 380

Ser Phe Gly Gly Tyr Pro Leu Arg Gly Ser Ser Ile Phe Gly Leu Ala
385                 390                 395                 400

Pro Gly Lys Ala Arg Asp Arg Lys Ala Tyr Thr Val Leu Leu Tyr Gly
                405                 410                 415

Asn Gly Pro Gly Tyr Val Leu Lys Asp Gly Ala Arg Pro Asp Val Thr
                420                 425                 430

Glu Ser Glu Ser Gly Ser Pro Glu Tyr Arg Gln Gln Ser Ala Val Pro
                435                 440                 445

Leu Asp Glu Glu Thr His Ala Gly Glu Asp Val Ala Val Phe Ala Arg
                450                 455                 460

Gly Pro Gln Ala His Leu Val His Gly Val Gln Glu Gln Thr Phe Ile
465                 470                 475                 480

Ala His Val Met Ala Phe Ala Ala Cys Leu Glu Pro Tyr Thr Ala Cys
                485                 490                 495

Asp Leu Ala Pro Pro Ala Gly Thr Thr Asp Ala Ala His Pro Gly Arg
                500                 505                 510

Ser Val Val Pro Ala Leu Leu Pro Leu Leu Ala Gly Thr Leu Leu Leu
                515                 520                 525

Leu Glu Thr Ala Thr Ala Pro
                530                 535

<210> SEQ ID NO 2
<211> LENGTH: 532
<212> TYPE: PRT
<213> ORGANISM: Homo sapiens

<400> SEQUENCE: 2

Met Gln Gly Pro Trp Val Leu Leu Leu Leu Gly Leu Arg Leu Gln Leu
1               5                   10                  15

Ser Leu Gly Ile Ile Pro Val Glu Glu Glu Asn Pro Asp Phe Trp Asn
                20                  25                  30

Arg Gln Ala Ala Glu Ala Leu Gly Ala Ala Lys Lys Leu Gln Pro Ala
            35                  40                  45

Gln Thr Ala Ala Lys Asn Leu Ile Ile Phe Leu Gly Asp Gly Met Gly
        50                  55                  60

Val Ser Thr Val Thr Ala Ala Arg Ile Leu Lys Gly Gln Lys Lys Asp
65                  70                  75                  80

Lys Leu Gly Pro Glu Thr Phe Leu Ala Met Asp Arg Phe Pro Tyr Val
                85                  90                  95

Ala Leu Ser Lys Thr Tyr Ser Val Asp Lys His Val Pro Asp Ser Gly
                100                 105                 110

Ala Thr Ala Thr Ala Tyr Leu Cys Gly Val Lys Gly Asn Phe Gln Thr
            115                 120                 125

Ile Gly Leu Ser Ala Ala Ala Arg Phe Asn Gln Cys Asn Thr Thr Arg
        130                 135                 140
```

-continued

```
Gly Asn Glu Val Ile Ser Val Met Asn Arg Ala Lys Lys Ala Gly Lys
145                 150                 155                 160

Ser Val Gly Val Val Thr Thr Thr Arg Val Gln His Ala Ser Pro Ala
            165                 170                 175

Gly Ala Tyr Ala His Thr Val Asn Arg Asn Trp Tyr Ser Asp Ala Asp
        180                 185                 190

Val Pro Ala Ser Ala Arg Gln Glu Gly Cys Gln Asp Ile Ala Thr Gln
    195                 200                 205

Leu Ile Ser Asn Met Asp Ile Asp Val Ile Leu Gly Gly Arg Lys
210                 215                 220

Tyr Met Phe Pro Met Gly Thr Pro Asp Pro Glu Tyr Pro Asp Asp Tyr
225                 230                 235                 240

Ser Gln Gly Gly Thr Arg Leu Asp Gly Lys Asn Leu Val Gln Glu Trp
            245                 250                 255

Leu Ala Lys His Gln Gly Ala Arg Tyr Val Trp Asn Arg Thr Glu Leu
        260                 265                 270

Leu Gln Ala Ser Leu Asp Pro Ser Val Thr His Leu Met Gly Leu Phe
    275                 280                 285

Glu Pro Gly Asp Met Lys Tyr Glu Ile His Arg Asp Ser Thr Leu Asp
290                 295                 300

Pro Ser Leu Met Glu Met Thr Glu Ala Ala Leu Leu Leu Ser Arg
305                 310                 315                 320

Asn Pro Arg Gly Phe Phe Leu Phe Val Glu Gly Gly Arg Ile Asp His
            325                 330                 335

Gly His His Glu Ser Arg Ala Tyr Arg Ala Leu Thr Glu Thr Ile Met
        340                 345                 350

Phe Asp Asp Ala Ile Glu Arg Ala Gly Gln Leu Thr Ser Glu Glu Asp
    355                 360                 365

Thr Leu Ser Leu Val Thr Ala Asp His Ser His Val Phe Ser Phe Gly
370                 375                 380

Gly Tyr Pro Leu Arg Gly Ser Ser Ile Phe Gly Leu Ala Pro Gly Lys
385                 390                 395                 400

Ala Arg Asp Arg Lys Ala Tyr Thr Val Leu Leu Tyr Gly Asn Gly Pro
            405                 410                 415

Gly Tyr Val Leu Lys Asp Gly Ala Arg Pro Asp Val Thr Glu Ser Glu
        420                 425                 430

Ser Gly Ser Pro Glu Tyr Arg Gln Gln Ser Ala Val Pro Leu Asp Gly
    435                 440                 445

Glu Thr His Ala Gly Glu Asp Val Ala Val Phe Ala Arg Gly Pro Gln
450                 455                 460

Ala His Leu Val His Gly Val Gln Glu Gln Thr Phe Ile Ala His Val
465                 470                 475                 480

Met Ala Phe Ala Ala Cys Leu Glu Pro Tyr Thr Ala Cys Asp Leu Ala
            485                 490                 495

Pro Arg Ala Gly Thr Thr Asp Ala Ala His Pro Gly Pro Ser Val Val
        500                 505                 510

Pro Ala Leu Leu Pro Leu Leu Ala Gly Thr Leu Leu Leu Leu Gly Thr
    515                 520                 525

Ala Thr Ala Pro
    530
```

<210> SEQ ID NO 3
<211> LENGTH: 247
<212> TYPE: PRT

```
<213> ORGANISM: Artificial
<220> FEATURE:
<223> OTHER INFORMATION: Synthetic antibody

<400> SEQUENCE: 3

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
                85                  90                  95

Ala Lys Glu Gly Asp Ser Ser Arg Trp Ser Tyr Asp Leu Trp Gly Arg
            100                 105                 110

Gly Thr Leu Val Thr Val Ser Ser Gly Gly Gly Ser Gly Gly Gly Gly
        115                 120                 125

Gly Ser Gly Gly Gly Gly Ser Gln Ser Ala Leu Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Ser Ser Tyr Thr Ser Thr Ser Thr Phe Val Val Phe Gly Gly Gly
225                 230                 235                 240

Thr Lys Leu Thr Val Leu Gly
                245

<210> SEQ ID NO 4
<211> LENGTH: 247
<212> TYPE: PRT
<213> ORGANISM: Artificial
<220> FEATURE:
<223> OTHER INFORMATION: Synthetic antibody

<400> SEQUENCE: 4

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Ser Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asp Ser Leu Arg Ala Glu Asp Thr Ala Val Tyr Phe Cys
                85                  90                  95

Ala Lys Glu Gly Asp Ser Ser Arg Trp Ser Tyr Asp Leu Trp Gly Arg
            100                 105                 110

Gly Thr Leu Val Thr Val Ser Ser Gly Gly Gly Gly Ser Gly Gly Gly
        115                 120                 125

Gly Ser Gly Gly Gly Gly Ser Gln Ser Ala Leu Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
            180                 185                 190

Ser Gly Val Ser Asn Arg Phe Ser Gly Ser Lys Ser Gly Asn Thr Ala
                195                 200                 205

Ser Leu Thr Ile Ser Gly Leu Gln Ala Glu Asp Glu Ala Asp Tyr Tyr
        210                 215                 220

Cys Ser Ser Tyr Thr Ser Thr Ser Thr Phe Val Val Phe Gly Gly Gly
225                 230                 235                 240

Thr Lys Leu Thr Val Leu Gly
                245

<210> SEQ ID NO 5
<211> LENGTH: 247
<212> TYPE: PRT
<213> ORGANISM: Artificial
<220> FEATURE:
<223> OTHER INFORMATION: Synthetic antibody

<400> SEQUENCE: 5

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Ser Tyr Asp Ser Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
                85                  90                  95

Ala Lys Glu Gly Asp Ser Ser Arg Trp Ser Tyr Asp Leu Trp Gly Arg
            100                 105                 110

Gly Thr Leu Val Thr Val Ser Ser Gly Gly Gly Gly Ser Gly Gly Gly
        115                 120                 125

Gly Ser Gly Gly Gly Gly Ser Gln Ser Ala Leu Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
            180                 185                 190
```

```
Ser Gly Val Ser Asn Arg Phe Ser Gly Ser Lys Ser Gly Asn Thr Ala
            195                 200                 205

Ser Leu Thr Ile Ser Gly Leu Gln Ala Glu Asp Glu Ala Asp Tyr Tyr
            210                 215                 220

Cys Ser Ser Tyr Thr Ser Thr Ser Thr Phe Val Val Phe Gly Gly Gly
225                 230                 235                 240

Thr Lys Leu Thr Val Leu Gly
                245

<210> SEQ ID NO 6
<211> LENGTH: 246
<212> TYPE: PRT
<213> ORGANISM: Artificial
<220> FEATURE:
<223> OTHER INFORMATION: Synthetic antibody

<400> SEQUENCE: 6

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Lys Glu Gly Asp Ser Ser Arg Trp Ser Tyr Asp Leu Trp Gly Arg
            100                 105                 110

Gly Thr Leu Val Thr Val Ser Ser Gly Gly Gly Gly Ser Gly Gly Gly
        115                 120                 125

Gly Ser Gly Gly Gly Gly Ser Gln Ser Ala Leu Thr Gln Pro Ala Ser
        130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
            180                 185                 190

Ser Gly Val Ser Asn Arg Phe Ser Gly Ser Lys Ser Gly Asn Thr Ala
            195                 200                 205

Ser Leu Thr Ile Ser Gly Leu Gln Ala Glu Asp Glu Ala Asp Tyr Tyr
            210                 215                 220

Cys Ser Ser Tyr Thr Ile Ala Ser Thr Leu Val Val Phe Gly Gly Gly
225                 230                 235                 240

Thr Lys Leu Thr Val Leu
                245

<210> SEQ ID NO 7
<211> LENGTH: 246
<212> TYPE: PRT
<213> ORGANISM: Artificial
<220> FEATURE:
<223> OTHER INFORMATION: Synthetic antibody

<400> SEQUENCE: 7
```

```
Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Lys Glu Gly Asp Ser Ser Arg Trp Ser Tyr Asp Leu Trp Gly Arg
            100                 105                 110

Gly Thr Leu Val Thr Val Ser Gly Gly Gly Ser Gly Gly Gly
        115                 120                 125

Gly Ser Gly Gly Gly Ser Gln Ser Ala Leu Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
            180                 185                 190

Ser Gly Val Ser Asn Arg Phe Ser Gly Ser Lys Ser Gly Asn Thr Ala
            195                 200                 205

Ser Leu Thr Ile Ser Gly Leu Gln Ala Glu Asp Glu Ala Asp Tyr Tyr
        210                 215                 220

Cys Ser Ser Tyr Thr Ile Ala Ser Thr Leu Val Val Phe Gly Gly Gly
225                 230                 235                 240

Thr Lys Leu Thr Val Leu
                245

<210> SEQ ID NO 8
<211> LENGTH: 246
<212> TYPE: PRT
<213> ORGANISM: Artificial
<220> FEATURE:
<223> OTHER INFORMATION: Synthetic antibody

<400> SEQUENCE: 8

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Ser Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Lys Glu Gly Asp Ser Ser Arg Trp Ser Tyr Asp Leu Trp Gly Arg
            100                 105                 110
```

```
Gly Thr Leu Val Thr Val Ser Ser Gly Gly Gly Ser Gly Gly Gly
            115                 120                 125

Gly Ser Gly Gly Gly Ser Gln Ser Ala Leu Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Ser Ser Tyr Thr Ile Ala Ser Thr Leu Val Val Phe Gly Gly Gly
225                 230                 235                 240

Thr Lys Leu Thr Val Leu
                245

<210> SEQ ID NO 9
<211> LENGTH: 246
<212> TYPE: PRT
<213> ORGANISM: Artificial
<220> FEATURE:
<223> OTHER INFORMATION: Synthetic antibody

<400> SEQUENCE: 9

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
                85                  90                  95

Ala Lys Glu Gly Asp Ser Ser Arg Trp Ser Tyr Asp Leu Trp Gly Arg
            100                 105                 110

Gly Thr Leu Val Thr Val Ser Ser Gly Gly Gly Ser Gly Gly Gly
            115                 120                 125

Gly Ser Gly Gly Gly Ser Gln Ser Ala Leu Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220
```

```
Cys Ser Ser Tyr Thr Ser Thr Ser Thr Leu Val Val Phe Gly Gly Gly
225                 230                 235                 240

Thr Lys Leu Thr Val Leu
                245

<210> SEQ ID NO 10
<211> LENGTH: 246
<212> TYPE: PRT
<213> ORGANISM: Artificial
<220> FEATURE:
<223> OTHER INFORMATION: Synthetic antibody

<400> SEQUENCE: 10

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
                85                  90                  95

Ala Lys Glu Gly Asp Ser Ser Arg Trp Ser Tyr Asp Leu Trp Gly Arg
            100                 105                 110

Gly Thr Leu Val Thr Val Ser Gly Gly Gly Gly Ser Gly Gly Gly
        115                 120                 125

Gly Ser Gly Gly Gly Gly Ser Gln Ser Ala Leu Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Ser Ser Tyr Thr Ser Thr Ser Thr Leu Val Val Phe Gly Gly Gly
225                 230                 235                 240

Thr Lys Leu Thr Val Leu
                245

<210> SEQ ID NO 11
<211> LENGTH: 246
<212> TYPE: PRT
<213> ORGANISM: Artificial
<220> FEATURE:
<223> OTHER INFORMATION: Synthetic antibody

<400> SEQUENCE: 11

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
```

```
                 20                  25                  30
Ala Met His Trp Val Arg Gln Ala Pro Gly Lys Gly Leu Glu Trp Val
             35                  40                  45

Ala Val Ile Ser Tyr Asp Ser Asn Lys Tyr Tyr Ala Asp Ser Val
         50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
                 85                  90                  95

Ala Lys Glu Gly Asp Ser Ser Arg Trp Ser Tyr Asp Leu Trp Gly Arg
             100                 105                 110

Gly Thr Leu Val Thr Val Ser Ser Gly Gly Gly Ser Gly Gly Gly
             115                 120                 125

Gly Ser Gly Gly Gly Gly Ser Gln Ser Ala Leu Thr Gln Pro Ala Ser
             130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                 165                 170                 175

Pro Gly Lys Ala Pro Lys Val Met Ile Tyr Asp Val Thr Asn Arg Pro
             180                 185                 190

Ser Gly Val Ser Asn Arg Phe Ser Gly Ser Lys Ser Gly Asn Thr Ala
             195                 200                 205

Ser Leu Thr Ile Ser Gly Leu Gln Ala Glu Asp Glu Ala Asp Tyr Tyr
             210                 215                 220

Cys Ser Ser Tyr Thr Ser Thr Ser Thr Leu Val Val Phe Gly Gly Gly
225                 230                 235                 240

Thr Lys Leu Thr Val Leu
             245

<210> SEQ ID NO 12
<211> LENGTH: 247
<212> TYPE: PRT
<213> ORGANISM: Artificial
<220> FEATURE:
<223> OTHER INFORMATION: Synthetic antibody

<400> SEQUENCE: 12

Gln Val Gln Leu Gln Gln Ser Gly Gly Gly Leu Val Lys Pro Gly Gly
1               5                  10                  15

Ser Leu Arg Leu Ser Cys Ala Ala Ser Gly Phe Thr Phe Ser Ser Tyr
             20                  25                  30

Glu Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
                 85                  90                  95

Ala Lys Glu Gly Asp Ser Ser Arg Trp Ser Tyr Asp Leu Trp Gly Arg
             100                 105                 110

Gly Thr Leu Val Thr Val Ser Ser Gly Gly Gly Ser Gly Gly Gly
             115                 120                 125

Gly Ser Gly Gly Gly Gly Ser Gln Ser Ala Leu Thr Gln Pro Ala Ser
```

```
Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Ser Ser Tyr Thr Ser Thr Ser Thr Phe Val Val Phe Gly Gly Gly
225                 230                 235                 240

Thr Lys Leu Thr Val Leu Gly
                245

<210> SEQ ID NO 13
<211> LENGTH: 247
<212> TYPE: PRT
<213> ORGANISM: Artificial
<220> FEATURE:
<223> OTHER INFORMATION: Synthetic antibody

<400> SEQUENCE: 13

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Glu Met His Trp Val Arg Gln Ala Pro Gly Lys Gly Leu Glu Trp Val
        35                  40                  45

Ala Val Ile Ser Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
                85                  90                  95

Ala Lys Glu Gly Asp Ser Ser Arg Trp Ser Tyr Asp Leu Trp Gly Arg
            100                 105                 110

Gly Thr Leu Val Thr Val Ser Ser Gly Gly Gly Gly Ser Gly Gly Gly
        115                 120                 125

Gly Ser Gly Gly Gly Gly Ser Gln Ser Ala Leu Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Ser Ser Tyr Thr Ser Thr Ser Thr Phe Val Val Phe Gly Gly Gly
225                 230                 235                 240

Thr Lys Leu Thr Val Leu Gly
```

<210> SEQ ID NO 14
<211> LENGTH: 247
<212> TYPE: PRT
<213> ORGANISM: Artificial
<220> FEATURE:
<223> OTHER INFORMATION: Synthetic antibody

<400> SEQUENCE: 14

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Glu Met His Trp Val Arg Gln Ala Pro Gly Lys Gly Leu Glu Trp Val
        35                  40                  45

Ala Val Ile Ser Tyr Asp Ser Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
                85                  90                  95

Ala Lys Glu Gly Asp Ser Ser Arg Trp Ser Tyr Asp Leu Trp Gly Arg
            100                 105                 110

Gly Thr Leu Val Thr Val Ser Gly Gly Gly Gly Ser Gly Gly Gly
        115                 120                 125

Gly Ser Gly Gly Gly Gly Ser Gln Ser Ala Leu Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Ser Ser Tyr Thr Ser Thr Ser Thr Phe Val Phe Gly Gly Gly
225                 230                 235                 240

Thr Lys Leu Thr Val Leu Gly
            245

<210> SEQ ID NO 15
<211> LENGTH: 246
<212> TYPE: PRT
<213> ORGANISM: Artificial
<220> FEATURE:
<223> OTHER INFORMATION: Synthetic antibody

<400> SEQUENCE: 15

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

```
Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asp Ser Leu Arg Ala Glu Asp Thr Ala Val Tyr Phe Cys
                 85                  90                  95

Ala Lys Glu Gly Asp Ser Ser Arg Trp Ser Tyr Asp Leu Trp Gly Arg
                100                 105                 110

Gly Thr Leu Val Thr Val Ser Gly Gly Gly Ser Gly Gly
                115                 120                 125         Gly

Gly Ser Gly Gly Gly Ser Gln Ser Ala Leu Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
                180                 185                 190

Ser Gly Val Ser Asn Arg Phe Ser Gly Ser Lys Ser Gly Asn Thr Ala
                195                 200                 205

Ser Leu Thr Ile Ser Gly Leu Gln Ala Glu Asp Glu Ala Asp Tyr Tyr
                210                 215                 220

Cys Ser Ser Tyr Thr Ser Thr Ser Thr Pro Val Val Phe Gly Gly Gly
225                 230                 235                 240

Thr Lys Leu Thr Val Leu
                245

<210> SEQ ID NO 16
<211> LENGTH: 246
<212> TYPE: PRT
<213> ORGANISM: Artificial
<220> FEATURE:
<223> OTHER INFORMATION: Synthetic antibody

<400> SEQUENCE: 16

Gln Val Gln Leu Gln Gln Ser Gly Gly Gly Leu Val Lys Pro Gly Gly
 1                   5                  10                  15

Ser Leu Arg Leu Ser Cys Ala Ala Ser Gly Phe Thr Phe Ser Ser Tyr
                 20                  25                  30

Asp Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asp Ser Leu Arg Ala Glu Asp Thr Ala Val Tyr Phe Cys
                 85                  90                  95

Ala Lys Glu Gly Asp Ser Ser Arg Trp Ser Tyr Asp Leu Trp Gly Arg
                100                 105                 110

Gly Thr Leu Val Thr Val Ser Ser Gly Gly Gly Ser Gly Gly Gly
                115                 120                 125

Gly Ser Gly Gly Gly Ser Gln Ser Ala Leu Thr Gln Pro Ala Ser
    130                 135                 140

Val Ser Gly Ser Pro Gly Gln Ser Ile Thr Ile Ser Cys Thr Gly Thr
145                 150                 155                 160
```

```
Ser Ser Asp Val Gly Gly Tyr Asn Tyr Val Ser Trp Tyr Gln Gln His
            165                 170                 175
Pro Gly Lys Ala Pro Lys Val Met Ile Tyr Asp Val Thr Asn Arg Pro
            180                 185                 190
Ser Gly Val Ser Asn Arg Phe Ser Gly Ser Lys Ser Gly Asn Thr Ala
            195                 200                 205
Ser Leu Thr Ile Ser Gly Leu Gln Ala Glu Asp Glu Ala Asp Tyr Tyr
            210                 215                 220
Cys Ser Ser Tyr Thr Ser Thr Ser Thr Gly Val Val Phe Gly Gly Gly
225                 230                 235                 240
Thr Lys Leu Thr Val Leu
            245

<210> SEQ ID NO 17
<211> LENGTH: 246
<212> TYPE: PRT
<213> ORGANISM: Artificial
<220> FEATURE:
<223> OTHER INFORMATION: Synthetic antibody

<400> SEQUENCE: 17

Gln Val Gln Leu Gln Gln Ser Gly Gly Gly Leu Val Lys Pro Gly Gly
1               5                   10                  15
Ser Leu Arg Leu Ser Cys Ala Ala Ser Gly Phe Thr Phe Ser Ser Tyr
            20                  25                  30
Asp Met His Trp Val Arg Gln Ala Pro Gly Lys Gly Leu Glu Trp Val
            35                  40                  45
Ala Val Ile Ser Tyr Asp Gly Ser Asn Lys Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asp Ser Leu Arg Ala Glu Asp Thr Ala Val Tyr Phe Cys
                85                  90                  95
Ala Lys Glu Gly Asp Ser Ser Arg Trp Ser Tyr Asp Leu Trp Gly Arg
            100                 105                 110
Gly Thr Leu Val Thr Val Ser Ser Gly Gly Gly Ser Gly Gly Gly
            115                 120                 125
Gly Ser Gly Gly Gly Gly Ser Gln Ser Ala Leu Thr Gln Pro Ala Ser
        130                 135                 140
Val Ser Gly Ser Pro Gly Gln Ser Ile Thr Ile Ser Cys Thr Gly Thr
145                 150                 155                 160
Ser Ser Asp Val Gly Gly Tyr Asn Tyr Val Ser Trp Tyr Gln Gln His
                165                 170                 175
Pro Gly Lys Ala Pro Lys Val Met Ile Tyr Asp Val Thr Asn Arg Pro
            180                 185                 190
Ser Gly Val Ser Asn Arg Phe Ser Gly Ser Lys Ser Gly Asn Thr Ala
            195                 200                 205
Ser Leu Thr Ile Ser Gly Leu Gln Ala Glu Asp Glu Ala Asp Tyr Tyr
            210                 215                 220
Cys Ser Ser Tyr Thr Arg Thr Ser Thr Leu Val Val Phe Gly Gly Gly
225                 230                 235                 240
Thr Lys Leu Thr Val Leu
            245

<210> SEQ ID NO 18
<211> LENGTH: 246
```

```
<212> TYPE: PRT
<213> ORGANISM: Artificial
<220> FEATURE:
<223> OTHER INFORMATION: Synthetic antibody

<400> SEQUENCE: 18

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
                85                  90                  95

Ala Lys Glu Gly Asp Ser Ser Arg Trp Ser Tyr Asp Leu Trp Gly Arg
            100                 105                 110

Gly Thr Leu Val Thr Val Ser Ser Gly Gly Gly Gly Ser Gly Gly Gly
        115                 120                 125

Gly Ser Gly Gly Gly Gly Ser Gln Ser Ala Leu Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Gly Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Ser Ser Tyr Thr Ser Thr Ser Thr Leu Val Val Phe Gly Gly Gly
225                 230                 235                 240

Thr Lys Leu Thr Val Leu
                245

<210> SEQ ID NO 19
<211> LENGTH: 246
<212> TYPE: PRT
<213> ORGANISM: Artificial
<220> FEATURE:
<223> OTHER INFORMATION: Synthetic antibody

<400> SEQUENCE: 19

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asp Ser Leu Arg Ala Glu Asp Thr Ala Val Tyr Phe Cys
                85                  90                  95

Ala Lys Glu Gly Asp Ser Ser Arg Trp Ser Tyr Asp Leu Trp Gly Arg
            100                 105                 110

Gly Thr Leu Val Thr Val Ser Ser Gly Gly Gly Ser Gly Gly Gly
        115                 120                 125

Gly Ser Gly Gly Gly Ser Gln Ser Ala Leu Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
            180                 185                 190

Ser Gly Val Ser Asn Arg Phe Ser Gly Ser Lys Ser Gly Asn Thr Ala
                195                 200                 205

Ser Leu Thr Ile Ser Gly Leu Gln Ala Glu Asp Glu Ala Asp Tyr Tyr
            210                 215                 220

Cys Gly Ser Tyr Thr Ser Thr Ser Thr Leu Val Val Phe Gly Gly Gly
225                 230                 235                 240

Thr Lys Leu Thr Val Leu
                245

<210> SEQ ID NO 20
<211> LENGTH: 246
<212> TYPE: PRT
<213> ORGANISM: Artificial
<220> FEATURE:
<223> OTHER INFORMATION: Synthetic antibody

<400> SEQUENCE: 20

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
                85                  90                  95

Ala Lys Glu Gly Asp Ser Ser Arg Trp Ser Tyr Asp Leu Trp Gly Arg
            100                 105                 110

Gly Thr Leu Val Thr Val Ser Ser Gly Gly Gly Ser Gly Gly Gly
        115                 120                 125

Gly Ser Gly Gly Gly Ser Gln Ser Ala Leu Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
            180                 185                 190
```

```
Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Ser Ser His Thr Ser Thr Ser Thr Leu Val Val Phe Gly Gly Gly
225                 230                 235                 240

Thr Lys Leu Thr Val Leu
                245

<210> SEQ ID NO 21
<211> LENGTH: 246
<212> TYPE: PRT
<213> ORGANISM: Artificial
<220> FEATURE:
<223> OTHER INFORMATION: Synthetic antibody

<400> SEQUENCE: 21

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
                85                  90                  95

Ala Lys Glu Gly Asp Ser Ser Arg Trp Ser Tyr Asp Leu Trp Gly Arg
            100                 105                 110

Gly Thr Leu Val Thr Val Ser Ser Gly Gly Gly Ser Gly Gly Gly
        115                 120                 125

Gly Ser Gly Gly Gly Gly Ser Ser Ala Leu Thr Gln Pro Ala Ser Val
    130                 135                 140

Ser Gly Ser Pro Gly Gln Ser Ile Thr Ile Ser Cys Thr Gly Thr Ser
145                 150                 155                 160

Ser Asp Val Gly Gly Tyr Asn Tyr Val Ser Trp Tyr Gln Gln His Pro
                165                 170                 175

Gly Lys Ala Pro Lys Val Met Ile Tyr Asp Val Thr Asn Arg Pro Ser
            180                 185                 190

Gly Val Ser Asn Arg Phe Ser Gly Ser Lys Ser Gly Asn Thr Ala Ser
        195                 200                 205

Leu Thr Ile Ser Gly Leu Gln Ala Glu Asp Glu Ala Asp Tyr Tyr Cys
    210                 215                 220

Ser Ser His Thr Arg Thr Ser Thr Phe Val Val Phe Gly Gly Gly Thr
225                 230                 235                 240

Lys Leu Thr Val Leu Gly
                245

<210> SEQ ID NO 22
<211> LENGTH: 246
<212> TYPE: PRT
<213> ORGANISM: Artificial
<220> FEATURE:
<223> OTHER INFORMATION: Synthetic antibody
```

<400> SEQUENCE: 22

```
Gln Val Gln Leu Gln Gln Ser Gly Gly Gly Leu Val Lys Pro Gly Gly
1               5                   10                  15

Ser Leu Arg Leu Ser Cys Ala Ala Ser Arg Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Thr Ser Arg Asp Asn Ser Lys Asn Thr Leu Tyr
65                  70                  75                  80

Leu Gln Met Asp Gly Leu Arg Ala Glu Asp Thr Ala Val Tyr Tyr Cys
                85                  90                  95

Ala Lys Glu Asp Asp Ser Ser Arg Trp Ser Tyr Asp Leu Trp Gly Arg
            100                 105                 110

Gly Thr Leu Val Thr Val Ser Ser Gly Gly Gly Ser Gly Gly Gly
        115                 120                 125

Gly Ser Gly Gly Gly Gly Ser Gln Ser Ala Leu Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Ser Ser Tyr Thr Ser Thr Ser Thr Leu Val Val Phe Gly Gly Gly
225                 230                 235                 240

Thr Lys Leu Thr Val Leu
                245
```

<210> SEQ ID NO 23
<211> LENGTH: 246
<212> TYPE: PRT
<213> ORGANISM: Artificial
<220> FEATURE:
<223> OTHER INFORMATION: Synthetic antibody

<400> SEQUENCE: 23

```
Gln Val Gln Leu Gln Gln Ser Gly Gly Gly Leu Val Lys Pro Gly Gly
1               5                   10                  15

Ser Leu Arg Leu Ser Cys Ala Ala Ser Gly Ser Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Thr Ser Arg Asp Asn Ser Lys Asn Thr Leu Tyr
65                  70                  75                  80

Leu Gln Met Asp Gly Leu Arg Ala Glu Asp Thr Ala Val Tyr Tyr Cys
                85                  90                  95

Ala Lys Glu Asp Asp Ser Ser Arg Trp Ser Tyr Asp Leu Trp Gly Arg
```

```
                100               105                 110
Gly Thr Leu Val Thr Val Ser Ser Gly Gly Gly Ser Gly Gly Gly
            115                 120                 125

Gly Ser Gly Gly Gly Ser Gln Ser Ala Leu Thr Gln Pro Ala Ser
            130                 135             140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Ser Ser Tyr Thr Ser Thr Ser Thr Leu Val Val Phe Gly Gly Gly
225                 230                 235                 240

Thr Lys Leu Thr Val Leu
                245

<210> SEQ ID NO 24
<211> LENGTH: 246
<212> TYPE: PRT
<213> ORGANISM: Artificial
<220> FEATURE:
<223> OTHER INFORMATION: Synthetic antibody

<400> SEQUENCE: 24

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Asp Ser Ser Arg Trp Ser Tyr Asp Leu Trp Gly Arg
            100                 105                 110

Gly Thr Leu Val Thr Val Ser Ser Gly Gly Gly Ser Gly Gly Gly
            115                 120                 125

Gly Ser Gly Gly Gly Ser Gln Ser Ala Leu Thr Gln Pro Ala Ser
            130                 135             140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
```

-continued

```
                210                 215                 220

Cys Ser Ser Tyr Thr Ile Ala Ser Thr Leu Val Val Phe Gly Gly Gly
225                 230                 235                 240

Thr Lys Leu Thr Val Leu
                245

<210> SEQ ID NO 25
<211> LENGTH: 247
<212> TYPE: PRT
<213> ORGANISM: Artificial
<220> FEATURE:
<223> OTHER INFORMATION: Synthetic antibody

<400> SEQUENCE: 25

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Asp Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Asp Ser Ser Arg Trp Ser Tyr Asp Leu Trp Gly Arg
            100                 105                 110

Gly Thr Leu Val Thr Val Ser Ser Gly Gly Gly Gly Ser Gly Gly Gly
        115                 120                 125

Gly Ser Gly Gly Gly Gly Ser Gln Ser Ala Leu Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Ser Ser Tyr Thr Ser Thr Ser Thr Phe Val Val Phe Gly Gly Gly
225                 230                 235                 240

Thr Lys Leu Thr Val Leu Gly
                245

<210> SEQ ID NO 26
<211> LENGTH: 246
<212> TYPE: PRT
<213> ORGANISM: Artificial
<220> FEATURE:
<223> OTHER INFORMATION: Synthetic antibody

<400> SEQUENCE: 26

Gln Val Gln Leu Gln Gln Ser Gly Gly Gly Leu Val Lys Pro Gly Gly
1               5                   10                  15
```

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
            85                  90                  95

Ala Lys Glu Gly Asp Ser Ser Arg Trp Ser Tyr Asp Leu Trp Gly Arg
            100                 105                 110

Gly Thr Leu Val Thr Val Ser Ser Gly Gly Gly Gly Ser Gly Gly Gly
            115                 120                 125

Gly Ser Gly Gly Gly Gly Ser Gln Ser Ala Leu Thr Gln Pro Ala Ser
            130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
            165                 170                 175

Pro Gly Lys Ala Pro Lys Val Met Ile Tyr Asp Val Thr Asn Arg Pro
            180                 185                 190

Ser Gly Val Ser Asn Arg Phe Ser Gly Ser Lys Ser Gly Asn Thr Ala
            195                 200                 205

Ser Leu Thr Ile Ser Gly Leu Gln Ala Glu Asp Glu Ala Asp Tyr Tyr
    210                 215                 220

Cys Ser Ser Tyr Thr Ser Thr Ser Thr Leu Val Val Phe Gly Gly Gly
225                 230                 235                 240

Thr Lys Leu Thr Val Leu
            245

<210> SEQ ID NO 27
<211> LENGTH: 247
<212> TYPE: PRT
<213> ORGANISM: Artificial
<220> FEATURE:
<223> OTHER INFORMATION: Synthetic antibody

<400> SEQUENCE: 27

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Arg Asn Thr Leu Ser
65                  70                  75                  80

Leu Gln Met Ser Ser Leu Arg Ala Glu Asp Thr Ala Leu Tyr Tyr Cys
            85                  90                  95

Val Lys Glu Gly Asp Ser Ser Arg Trp Ser Tyr Asp Pro Trp Gly Arg
            100                 105                 110

Gly Thr Leu Val Thr Val Ser Ser Gly Gly Gly Ser Gly Gly Gly
            115                 120                 125

```
Gly Ser Gly Gly Gly Ser Gln Ser Ala Leu Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Ser Ser Tyr Thr Ser Thr Ser Thr Leu Val Val Phe Gly Gly Gly
225                 230                 235                 240

Thr Lys Leu Thr Val Leu Gly
                245

<210> SEQ ID NO 28
<211> LENGTH: 246
<212> TYPE: PRT
<213> ORGANISM: Artificial
<220> FEATURE:
<223> OTHER INFORMATION: Synthetic antibody

<400> SEQUENCE: 28

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
                85                  90                  95

Ala Lys Glu Gly Asp Ser Ser Arg Trp Ser Tyr Asp Leu Trp Gly Arg
            100                 105                 110

Gly Thr Leu Val Thr Val Ser Ser Gly Gly Gly Ser Gly Gly Gly
        115                 120                 125

Gly Ser Gly Gly Gly Gly Ser Gln Ser Ala Leu Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Val Gly Gly Tyr Lys Tyr Val Ser Trp Tyr Gln Gln His
                165                 170                 175

Pro Gly Lys Ala Pro Lys Leu Met Ile Tyr Glu Val Ser Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Ala Tyr Phe
    210                 215                 220

Cys Ser Ala Tyr Ser Pro Pro Gly Ile Met Met Phe Gly Gly Gly Thr
225                 230                 235                 240
```

Lys Leu Thr Val Leu Gly
            245

<210> SEQ ID NO 29
<211> LENGTH: 246
<212> TYPE: PRT
<213> ORGANISM: Artificial
<220> FEATURE:
<223> OTHER INFORMATION: Synthetic antibody

<400> SEQUENCE: 29

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
                85                  90                  95

Ala Lys Glu Gly Asp Ser Ser Arg Trp Ser Tyr Asp Leu Trp Gly Arg
            100                 105                 110

Gly Thr Leu Val Thr Val Ser Ser Gly Gly Gly Gly Ser Gly Gly Gly
        115                 120                 125

Gly Ser Gly Gly Gly Gly Ser Gln Ser Ala Leu Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Val Gly Gly Tyr Lys Tyr Val Ser Trp Tyr Gln Gln His
                165                 170                 175

Pro Gly Lys Ala Pro Lys Leu Met Ile Tyr Glu Val Ser Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Ala Tyr Phe
    210                 215                 220

Cys Ser Ala Tyr Ser Pro Pro Gly Ile Met Met Phe Gly Gly Gly Thr
225                 230                 235                 240

Lys Leu Thr Val Leu Gly
            245

<210> SEQ ID NO 30
<211> LENGTH: 246
<212> TYPE: PRT
<213> ORGANISM: Artificial
<220> FEATURE:
<223> OTHER INFORMATION: Synthetic antibody

<400> SEQUENCE: 30

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asp Ser Leu Arg Ala Glu Asp Thr Ala Val Tyr Phe Cys
                    85                  90                  95

Ala Lys Glu Gly Asp Ser Ser Arg Trp Ser Tyr Asp Leu Trp Gly Arg
            100                 105                 110

Gly Thr Leu Val Thr Val Ser Gly Gly Gly Ser Gly Gly
            115                 120                 125

Gly Ser Gly Gly Gly Ser Gln Ser Ala Leu Thr Gln Pro Ala Ser
        130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                    165                 170                 175

Pro Gly Lys Ala Pro Lys Val Met Ile Tyr Asp Val Thr Asn Arg Pro
            180                 185                 190

Ser Gly Val Ser Asn Arg Phe Ser Gly Ser Lys Ser Gly Asn Thr Ala
                195                 200                 205

Ser Leu Thr Ile Ser Gly Leu Gln Ala Glu Asp Glu Ala Asp Tyr Tyr
            210                 215                 220

Cys Ser Ser Tyr Thr Ile Ala Ser Thr Leu Val Val Phe Gly Gly Gly
225                 230                 235                 240

Thr Lys Leu Thr Val Leu
                245

<210> SEQ ID NO 31
<211> LENGTH: 247
<212> TYPE: PRT
<213> ORGANISM: Artificial
<220> FEATURE:
<223> OTHER INFORMATION: Synthetic antibody

<400> SEQUENCE: 31

Gln Val Gln Leu Gln Gln Ser Gly Gly Gly Leu Val Lys Pro Gly Gly
 1                5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asp Ser Leu Arg Ala Glu Asp Thr Ala Val Tyr Phe Cys
                    85                  90                  95

Ala Lys Glu Gly Asp Ser Ser Arg Trp Ser Tyr Asp Leu Trp Gly Arg
            100                 105                 110

Gly Thr Leu Val Thr Val Ser Gly Gly Gly Ser Gly Gly
            115                 120                 125

Gly Ser Gly Gly Gly Ser Gln Ser Ala Leu Thr Gln Pro Ala Ser
        130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
            165                 170                 175

Pro Gly Lys Ala Pro Lys Val Met Ile Tyr Asp Val Thr Asn Arg Pro
        180                 185                 190

Ser Gly Val Ser Asn Arg Phe Ser Gly Ser Lys Ser Gly Asn Thr Ala
            195                 200                 205

Ser Leu Thr Ile Ser Gly Leu Gln Ala Glu Asp Glu Ala Asp Tyr Tyr
    210                 215                 220

Cys Ser Ser Tyr Thr Ser Thr Ser Thr Phe Val Val Phe Gly Gly Gly
225                 230                 235                 240

Thr Lys Leu Thr Val Leu Gly
            245

<210> SEQ ID NO 32
<211> LENGTH: 246
<212> TYPE: PRT
<213> ORGANISM: Artificial
<220> FEATURE:
<223> OTHER INFORMATION: Synthetic antibody

<400> SEQUENCE: 32

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
            85                  90                  95

Ala Lys Glu Gly Asp Ser Ser Arg Trp Ser Tyr Asp Leu Trp Gly Arg
        100                 105                 110

Gly Thr Leu Val Thr Val Ser Ser Gly Gly Gly Ser Gly Gly Gly Gly
    115                 120                 125

Gly Ser Gly Gly Gly Ser Gln Ser Ala Leu Thr Gln Pro Ala Ser
        130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
            165                 170                 175

Pro Gly Lys Ala Pro Lys Val Met Ile Tyr Asp Val Thr Asn Arg Pro
        180                 185                 190

Ser Gly Val Ser Asn Arg Phe Ser Gly Ser Lys Ser Gly Asn Thr Ala
            195                 200                 205

Ser Leu Thr Ile Ser Gly Leu Gln Ala Glu Asp Glu Ala Asp Tyr Tyr
    210                 215                 220

Cys Ser Ser Tyr Thr Ile Ala Ser Thr Leu Val Val Phe Gly Gly Gly
225                 230                 235                 240

Thr Lys Leu Thr Val Leu
            245

<210> SEQ ID NO 33

```
<211> LENGTH: 247
<212> TYPE: PRT
<213> ORGANISM: Artificial
<220> FEATURE:
<223> OTHER INFORMATION: Synthetic antibody

<400> SEQUENCE: 33

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
                85                  90                  95

Ala Lys Glu Gly Asp Ser Ser Arg Trp Ser Tyr Asp Leu Trp Gly Arg
            100                 105                 110

Gly Thr Leu Val Thr Val Ser Ser Gly Gly Gly Ser Gly Gly Gly
        115                 120                 125

Gly Ser Gly Gly Gly Ser Gln Ser Ala Leu Thr Gln Pro Ala Ser
130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Ser Ser Tyr Thr Ser Thr Ser Thr Phe Val Phe Gly Gly Gly
225                 230                 235                 240

Thr Lys Leu Thr Val Leu Gly
            245

<210> SEQ ID NO 34
<211> LENGTH: 246
<212> TYPE: PRT
<213> ORGANISM: Artificial
<220> FEATURE:
<223> OTHER INFORMATION: Synthetic antibody

<400> SEQUENCE: 34

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Met Asp Ser Leu Arg Ala Glu Asp Thr Ala Val Tyr Phe Cys
                    85                  90                  95

Ala Lys Glu Gly Asp Ser Ser Arg Trp Ser Tyr Asp Leu Trp Gly Arg
                100                 105                 110

Gly Thr Leu Val Thr Val Ser Gly Gly Gly Ser Gly Gly Gly
                115                 120                 125

Gly Ser Gly Gly Gly Ser Gln Ser Ala Leu Thr Gln Pro Ala Ser
            130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                    165                 170                 175

Pro Gly Lys Ala Pro Lys Val Met Ile Tyr Asp Val Thr Asn Arg Pro
                180                 185                 190

Ser Gly Val Ser Asn Arg Phe Ser Gly Ser Lys Ser Gly Asn Thr Ala
                195                 200                 205

Ser Leu Thr Ile Ser Gly Leu Gln Ala Glu Asp Glu Ala Asp Tyr Tyr
    210                 215                 220

Cys Ser Ser Tyr Thr Ser Thr Ser Thr Leu Val Val Phe Gly Gly Gly
225                 230                 235                 240

Thr Lys Leu Thr Val Leu
                245

<210> SEQ ID NO 35
<211> LENGTH: 246
<212> TYPE: PRT
<213> ORGANISM: Artificial
<220> FEATURE:
<223> OTHER INFORMATION: Synthetic antibody

<400> SEQUENCE: 35

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Val Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
                    85                  90                  95

Ala Lys Glu Gly Asp Ser Ser Arg Trp Ser Tyr Asp Leu Trp Gly Arg
                100                 105                 110

Gly Thr Leu Val Thr Val Ser Ser Gly Gly Gly Ser Gly Gly Gly
                115                 120                 125

Gly Ser Gly Gly Gly Ser Gln Ser Ala Leu Thr Gln Pro Ala Ser
            130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                    165                 170                 175

Pro Gly Lys Ala Pro Lys Val Met Ile Tyr Asp Val Thr Asn Arg Pro
```

```
                180                 185                 190
Ser Gly Val Ser Asn Arg Phe Ser Gly Ser Lys Ser Gly Asn Thr Ala
            195                 200                 205

Ser Leu Thr Ile Ser Gly Leu Gln Ala Glu Asp Glu Ala Asp Tyr Tyr
            210                 215                 220

Cys Ser Ser Tyr Thr Ile Ala Ser Thr Leu Val Val Phe Gly Gly Gly
225                 230                 235                 240

Thr Lys Leu Thr Val Leu
                245

<210> SEQ ID NO 36
<211> LENGTH: 247
<212> TYPE: PRT
<213> ORGANISM: Artificial
<220> FEATURE:
<223> OTHER INFORMATION: Synthetic antibody

<400> SEQUENCE: 36

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Val Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
                85                  90                  95

Ala Lys Glu Gly Asp Ser Ser Arg Trp Ser Tyr Asp Leu Trp Gly Arg
            100                 105                 110

Gly Thr Leu Val Thr Val Ser Ser Gly Gly Gly Ser Gly Gly Gly
            115                 120                 125

Gly Ser Gly Gly Gly Gly Ser Gln Ser Ala Leu Thr Gln Pro Ala Ser
130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
            180                 185                 190

Ser Gly Val Ser Asn Arg Phe Ser Gly Ser Lys Ser Gly Asn Thr Ala
            195                 200                 205

Ser Leu Thr Ile Ser Gly Leu Gln Ala Glu Asp Glu Ala Asp Tyr Tyr
            210                 215                 220

Cys Ser Ser Tyr Thr Ser Thr Ser Thr Phe Val Val Phe Gly Gly Gly
225                 230                 235                 240

Thr Lys Leu Thr Val Leu Gly
                245

<210> SEQ ID NO 37
<211> LENGTH: 246
<212> TYPE: PRT
<213> ORGANISM: Artificial
<220> FEATURE:
<223> OTHER INFORMATION: Synthetic antibody
```

```
<400> SEQUENCE: 37

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Leu Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
            85                  90                  95

Ala Lys Glu Gly Asp Ser Ser Arg Trp Ser Tyr Asp Leu Trp Gly Arg
            100                 105                 110

Gly Thr Leu Val Thr Val Ser Ser Gly Gly Gly Ser Gly Gly Gly
        115                 120                 125

Gly Ser Gly Gly Gly Gly Ser Gln Ser Ala Leu Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Ser Ser Tyr Thr Ile Ala Ser Thr Leu Val Val Phe Gly Gly Gly
225                 230                 235                 240

Thr Lys Leu Thr Val Leu
                245

<210> SEQ ID NO 38
<211> LENGTH: 247
<212> TYPE: PRT
<213> ORGANISM: Artificial
<220> FEATURE:
<223> OTHER INFORMATION: Synthetic antibody

<400> SEQUENCE: 38

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Leu Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
            85                  90                  95
```

```
Ala Lys Glu Gly Asp Ser Ser Arg Trp Ser Tyr Asp Leu Trp Gly Arg
            100                 105                 110

Gly Thr Leu Val Thr Val Ser Ser Gly Gly Gly Ser Gly Gly Gly
            115                 120                 125

Gly Ser Gly Gly Gly Ser Gln Ser Ala Leu Thr Gln Pro Ala Ser
            130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
                180                 185                 190

Ser Gly Val Ser Asn Arg Phe Ser Gly Ser Lys Ser Gly Asn Thr Ala
                195                 200                 205

Ser Leu Thr Ile Ser Gly Leu Gln Ala Glu Asp Glu Ala Asp Tyr Tyr
                210                 215                 220

Cys Ser Ser Tyr Thr Ser Thr Ser Thr Phe Val Val Phe Gly Gly Gly
225                 230                 235                 240

Thr Lys Leu Thr Val Leu Gly
                245
```

<210> SEQ ID NO 39
<211> LENGTH: 246
<212> TYPE: PRT
<213> ORGANISM: Artificial
<220> FEATURE:
<223> OTHER INFORMATION: Synthetic antibody

<400> SEQUENCE: 39

```
Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
                85                  90                  95

Ala Lys Glu Gly Asp Ser Ser Arg Trp Ser Tyr Asp Leu Trp Gly Arg
            100                 105                 110

Gly Thr Leu Val Thr Val Ser Ser Gly Gly Gly Ser Gly Gly Gly
            115                 120                 125

Gly Ser Gly Gly Gly Ser Gln Ser Ala Leu Thr Gln Pro Ala Ser
            130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
                180                 185                 190

Ser Gly Val Ser Asn Arg Phe Ser Gly Ser Lys Ser Gly Asn Thr Ala
                195                 200                 205
```

Ser Leu Thr Ile Ser Gly Leu Gln Ala Glu Asp Glu Ala Asp Tyr Tyr
            210                 215                 220

Cys Ser Ser Tyr Thr Ile Ala Ser Thr Leu Val Val Phe Gly Gly Gly
225                 230                 235                 240

Thr Lys Leu Thr Val Leu
            245

<210> SEQ ID NO 40
<211> LENGTH: 247
<212> TYPE: PRT
<213> ORGANISM: Artificial
<220> FEATURE:
<223> OTHER INFORMATION: Synthetic antibody

<400> SEQUENCE: 40

Gln Val Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Phe Cys
                85                  90                  95

Ala Lys Glu Gly Asp Ser Ser Arg Trp Ser Tyr Asp Leu Trp Gly Arg
            100                 105                 110

Gly Thr Leu Val Thr Val Ser Ser Gly Gly Gly Gly Ser Gly Gly Gly
        115                 120                 125

Gly Ser Gly Gly Gly Gly Ser Gln Ser Ala Leu Thr Gln Pro Ala Ser
    130                 135                 140

Val Ser Gly Ser Pro Gly Gln Ser Ile Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Val Met Ile Tyr Asp Val Thr Asn Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Gln Ala Glu Asp Glu Ala Asp Tyr Tyr
    210                 215                 220

Cys Ser Ser Tyr Thr Ser Thr Ser Thr Phe Val Val Phe Gly Gly Gly
225                 230                 235                 240

Thr Lys Leu Thr Val Leu Gly
            245

<210> SEQ ID NO 41
<211> LENGTH: 15
<212> TYPE: PRT
<213> ORGANISM: Artificial
<220> FEATURE:
<223> OTHER INFORMATION: Peptide linker

<400> SEQUENCE: 41

Gly Gly Gly Gly Ser Gly Gly Gly Gly Ser Gly Gly Gly Gly Ser
1               5                   10                  15

<210> SEQ ID NO 42
<211> LENGTH: 10
<212> TYPE: PRT
<213> ORGANISM: Artificial
<220> FEATURE:
<223> OTHER INFORMATION: Peptide linker

<400> SEQUENCE: 42

Gly Gly Gly Gly Ser Gly Gly Gly Gly Ser
1               5                   10

<210> SEQ ID NO 43
<211> LENGTH: 5
<212> TYPE: PRT
<213> ORGANISM: Artificial
<220> FEATURE:
<223> OTHER INFORMATION: Peptide linker

<400> SEQUENCE: 43

Gly Gly Gly Gly Ser
1               5

<210> SEQ ID NO 44
<211> LENGTH: 20
<212> TYPE: PRT
<213> ORGANISM: Artificial
<220> FEATURE:
<223> OTHER INFORMATION: Peptide linker

<400> SEQUENCE: 44

Gly Ser Gly Gly Gly Gly Ser Gly Gly Gly Ser Gly Gly Ser Gly
1               5                   10                  15

Gly Gly Gly Ser
            20

<210> SEQ ID NO 45
<211> LENGTH: 6
<212> TYPE: PRT
<213> ORGANISM: Artificial
<220> FEATURE:
<223> OTHER INFORMATION: Peptide linker

<400> SEQUENCE: 45

Ser Gly Gly Gly Gly Ser
1               5

<210> SEQ ID NO 46
<211> LENGTH: 4
<212> TYPE: PRT
<213> ORGANISM: Artificial
<220> FEATURE:
<223> OTHER INFORMATION: Peptide linker

<400> SEQUENCE: 46

Gly Gly Gly Ser
1

<210> SEQ ID NO 47
<211> LENGTH: 4
<212> TYPE: PRT
<213> ORGANISM: Artificial
<220> FEATURE:
<223> OTHER INFORMATION: Peptide linker

<400> SEQUENCE: 47

```
Val Pro Gly Val
1

<210> SEQ ID NO 48
<211> LENGTH: 5
<212> TYPE: PRT
<213> ORGANISM: Artificial
<220> FEATURE:
<223> OTHER INFORMATION: Peptide linker

<400> SEQUENCE: 48

Val Pro Gly Val Gly
1               5

<210> SEQ ID NO 49
<211> LENGTH: 6
<212> TYPE: PRT
<213> ORGANISM: Artificial
<220> FEATURE:
<223> OTHER INFORMATION: Peptide linker

<400> SEQUENCE: 49

Gly Val Pro Gly Val Gly
1               5

<210> SEQ ID NO 50
<211> LENGTH: 8
<212> TYPE: PRT
<213> ORGANISM: Artificial
<220> FEATURE:
<223> OTHER INFORMATION: Peptide linker

<400> SEQUENCE: 50

Gly Val Gly Val Pro Gly Val Gly
1               5

<210> SEQ ID NO 51
<211> LENGTH: 10
<212> TYPE: PRT
<213> ORGANISM: Artificial
<220> FEATURE:
<223> OTHER INFORMATION: Peptide linker

<400> SEQUENCE: 51

Val Pro Gly Val Gly Val Pro Gly Val Gly
1               5                   10

<210> SEQ ID NO 52
<211> LENGTH: 7
<212> TYPE: PRT
<213> ORGANISM: Artificial
<220> FEATURE:
<223> OTHER INFORMATION: Peptide linker

<400> SEQUENCE: 52

Gly Gly Ser Ser Arg Ser Ser
1               5

<210> SEQ ID NO 53
<211> LENGTH: 18
<212> TYPE: PRT
<213> ORGANISM: Artificial
<220> FEATURE:
<223> OTHER INFORMATION: Peptide linker

<400> SEQUENCE: 53

Gly Gly Ser Ser Arg Ser Ser Ser Ser Gly Gly Gly Gly Ser Gly Gly
```

Gly Gly

<210> SEQ ID NO 54
<211> LENGTH: 44
<212> TYPE: DNA
<213> ORGANISM: Artificial
<220> FEATURE:
<223> OTHER INFORMATION: PCR primer

<400> SEQUENCE: 54
gatcggtacc gatcggcgcg cccaaatctt gtgacaaaac tcac    44

<210> SEQ ID NO 55
<211> LENGTH: 42
<212> TYPE: DNA
<213> ORGANISM: Artificial
<220> FEATURE:
<223> OTHER INFORMATION: PCR primer

<400> SEQUENCE: 55
gatcggcgcg ccttccacca agggcccatc cgtcttcccc ct    42

<210> SEQ ID NO 56
<211> LENGTH: 48
<212> TYPE: DNA
<213> ORGANISM: Artificial
<220> FEATURE:
<223> OTHER INFORMATION: PCR primer

<400> SEQUENCE: 56
gatcggccca gccggcctca tttacccgga gacagggaga ggctcttc    48

<210> SEQ ID NO 57
<211> LENGTH: 38
<212> TYPE: DNA
<213> ORGANISM: Artificial
<220> FEATURE:
<223> OTHER INFORMATION: PCR primer

<400> SEQUENCE: 57
gatcggccca gccggcctca tttacccaga gacaggga    38

<210> SEQ ID NO 58
<211> LENGTH: 41
<212> TYPE: DNA
<213> ORGANISM: Artificial
<220> FEATURE:
<223> OTHER INFORMATION: PCR primer

<400> SEQUENCE: 58
gatctctaga tcatttaccc ggagacaggg agaggctctt c    41

<210> SEQ ID NO 59
<211> LENGTH: 32
<212> TYPE: DNA
<213> ORGANISM: Artificial
<220> FEATURE:
<223> OTHER INFORMATION: PCR primer

<400> SEQUENCE: 59
gatcggcgcg cccagcaaca ccaaggtgga ca    32

<210> SEQ ID NO 60
<211> LENGTH: 32

-continued

<212> TYPE: DNA
<213> ORGANISM: Artificial
<220> FEATURE:
<223> OTHER INFORMATION: PCR primer

<400> SEQUENCE: 60
gatcggcgcg ccagcctcca ccaagggccc at                          32

<210> SEQ ID NO 61
<211> LENGTH: 30
<212> TYPE: DNA
<213> ORGANISM: Artificial
<220> FEATURE:
<223> OTHER INFORMATION: PCR primer

<400> SEQUENCE: 61
gatcggcgcg cccatccgtc ttccccttga                             30

<210> SEQ ID NO 62
<211> LENGTH: 41
<212> TYPE: DNA
<213> ORGANISM: Artificial
<220> FEATURE:
<223> OTHER INFORMATION: PCR primer

<400> SEQUENCE: 62
gatcggccca gccggcctca tttaccggga tttacagaca c                41

<210> SEQ ID NO 63
<211> LENGTH: 29
<212> TYPE: DNA
<213> ORGANISM: Artificial
<220> FEATURE:
<223> OTHER INFORMATION: PCR primer

<400> SEQUENCE: 63
gatcggcgcg cccaccgtga agatcttac                              29

<210> SEQ ID NO 64
<211> LENGTH: 48
<212> TYPE: DNA
<213> ORGANISM: Artificial
<220> FEATURE:
<223> OTHER INFORMATION: PCR primer

<400> SEQUENCE: 64
gatctctaga tcaatggtgg tgatgtttac cgggatttac agacaccg         48

<210> SEQ ID NO 65
<211> LENGTH: 60
<212> TYPE: DNA
<213> ORGANISM: Artificial
<220> FEATURE:
<223> OTHER INFORMATION: PCR primer

<400> SEQUENCE: 65
gtacgctagc aagatggaat cacagaccca ggtcctcatg tccctgctgc tctggatttc   60

<210> SEQ ID NO 66
<211> LENGTH: 60
<212> TYPE: DNA
<213> ORGANISM: Artificial
<220> FEATURE:
<223> OTHER INFORMATION: PCR primer

<400> SEQUENCE: 66

```
catgtccctg ctgctctgga tttctggtac ctgtggggtg agtccttaca acgcgtgtac    60
```

<210> SEQ ID NO 67
<211> LENGTH: 33
<212> TYPE: DNA
<213> ORGANISM: Artificial
<220> FEATURE:
<223> OTHER INFORMATION: PCR primer

<400> SEQUENCE: 67

```
gatctctaga ctaacactct ccctgttga agc                                  33
```

<210> SEQ ID NO 68
<211> LENGTH: 37
<212> TYPE: DNA
<213> ORGANISM: Artificial
<220> FEATURE:
<223> OTHER INFORMATION: PCR primer

<400> SEQUENCE: 68

```
gatcgcgatc gcacgaactg tggctgcacc atctgtc                             37
```

<210> SEQ ID NO 69
<211> LENGTH: 71
<212> TYPE: DNA
<213> ORGANISM: Artificial
<220> FEATURE:
<223> OTHER INFORMATION: PCR primer

<400> SEQUENCE: 69

```
agaatgcggc cgctatggaa ttggggctga gctgggtttt ccttgttgct atatttaaat    60
gtgtccagtg t                                                         71
```

<210> SEQ ID NO 70
<211> LENGTH: 76
<212> TYPE: DNA
<213> ORGANISM: Artificial
<220> FEATURE:
<223> OTHER INFORMATION: PCR primer

<400> SEQUENCE: 70

```
gatcgtcgac atggacatga gggtccccgc tcagctcctg ggctcctgc tactctgcct     60 gcagggtgcc agatgt                                                    76
```

<210> SEQ ID NO 71
<211> LENGTH: 4
<212> TYPE: DNA
<213> ORGANISM: Artificial
<220> FEATURE:
<223> OTHER INFORMATION: Nucleic acid linker

<400> SEQUENCE: 71

```
gggg                                                                  4
```

<210> SEQ ID NO 72
<211> LENGTH: 5
<212> TYPE: DNA
<213> ORGANISM: Artificial
<220> FEATURE:
<223> OTHER INFORMATION: Nucleic acid linker

<400> SEQUENCE: 72

```
ggggs                                                                 5
```

```
<210> SEQ ID NO 73
<211> LENGTH: 15
<212> TYPE: DNA
<213> ORGANISM: Artificial
<220> FEATURE:
<223> OTHER INFORMATION: Nucleic acid linker

<400> SEQUENCE: 73
ggggsggggs ggggs                                                      15

<210> SEQ ID NO 74
<211> LENGTH: 22
<212> TYPE: PRT
<213> ORGANISM: Homo sapiens

<400> SEQUENCE: 74

Ile Trp Ala Pro Leu Ala Gly Thr Cys Gly Val Leu Leu Leu Ser Leu
1               5                   10                  15

Val Ile Thr Leu Tyr Cys
            20

<210> SEQ ID NO 75
<211> LENGTH: 72
<212> TYPE: DNA
<213> ORGANISM: Homo sapiens

<400> SEQUENCE: 75
atctacatct gggcgccctt ggccgggact tgtggggtcc ttctcctgtc actggttatc    60 acccttact gc                                                         72

<210> SEQ ID NO 76
<211> LENGTH: 47
<212> TYPE: PRT
<213> ORGANISM: Homo sapiens

<400> SEQUENCE: 76

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45

<210> SEQ ID NO 77
<211> LENGTH: 135
<212> TYPE: DNA
<213> ORGANISM: Homo sapiens

<400> SEQUENCE: 77
accacgacgc cagcgccgcg accaccaaca ccggcgccca ccatcgcgtc gcagcccctg    60
tccctgcgcc cagaggcgtg ccggccagcg gcggggggcg cagtgcacac gagggggctg   120
gacttcgcct gtgat                                                    135

<210> SEQ ID NO 78
<211> LENGTH: 42
<212> TYPE: PRT
<213> ORGANISM: Homo sapiens

<400> SEQUENCE: 78

Lys Arg Gly Arg Lys Lys Leu Leu Tyr Ile Phe Lys Gln Pro Phe Met
1               5                   10                  15
```

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 79
<211> LENGTH: 112
<212> TYPE: PRT
<213> ORGANISM: Homo sapiens

<400> SEQUENCE: 79

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 80
<211> LENGTH: 126
<212> TYPE: DNA
<213> ORGANISM: Homo sapiens

<400> SEQUENCE: 80
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126

<210> SEQ ID NO 81
<211> LENGTH: 240
<212> TYPE: DNA
<213> ORGANISM: Homo sapiens

<400> SEQUENCE: 81
agagtgaagt tcagcaggag cgcagacgcc cccgcgtaca gcagggcca gaaccagctc      60 tataacgagc tcaatctagg acgaagagag gagtacgatg ttttggacaa gagacgtggc    120
cgggaccctg agatgggggg aaagccgaga aggaagaacc ctcaggaagg cctgtacaat    180
gaactgcaga agataagat ggcggaggcc tacagtgaga ttgggatgaa aggcgagcgc     240

<210> SEQ ID NO 82
<211> LENGTH: 15
<212> TYPE: DNA
<213> ORGANISM: Artificial
<220> FEATURE:
<223> OTHER INFORMATION: Nucleic acid linker

<400> SEQUENCE: 82
ggggsggggs gggs                                                       15

<210> SEQ ID NO 83

```
<211> LENGTH: 31
<212> TYPE: DNA
<213> ORGANISM: Artificial
<220> FEATURE:
<223> OTHER INFORMATION: Synthetic antibody

<400> SEQUENCE: 83
gatctctaga tcatttaccc agagacaggg a                              31
```